(12) United States Patent
Weetall et al.

(10) Patent No.: US 9,873,677 B2
(45) Date of Patent: Jan. 23, 2018

(54) PHARMACEUTICAL COMPOSITIONS AND SALTS OF A 1,2,4-OXADIAZOLE BENZOIC ACID

(71) Applicant: PTC Therapeutics, Inc., South Plainfield, NJ (US)

(72) Inventors: Marla L. Weetall, Morristown, NJ (US); Ellen Welch, Califon, NJ (US); Mandar V. Dali, Bridgewater, NJ (US); James Takasugi, Lawrenceville, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 15/123,309

(22) PCT Filed: Mar. 5, 2015

(86) PCT No.: PCT/US2015/018889
§ 371 (c)(1),
(2) Date: Sep. 2, 2016

(87) PCT Pub. No.: WO2015/134711
PCT Pub. Date: Sep. 11, 2015

(65) Prior Publication Data
US 2017/0066730 A1 Mar. 9, 2017

Related U.S. Application Data

(60) Provisional application No. 62/009,111, filed on Jun. 6, 2014, provisional application No. 61/949,052, filed on Mar. 6, 2014.

(51) Int. Cl.
C07D 271/06 (2006.01)
A61K 31/4245 (2006.01)
A61K 9/00 (2006.01)

(52) U.S. Cl.
CPC .......... *C07D 271/06* (2013.01); *A61K 9/0048* (2013.01); *A61K 31/4245* (2013.01)

(58) Field of Classification Search
CPC ..................................................... C07D 271/06
See application file for complete search history.

(56) References Cited

U.S. PATENT DOCUMENTS 3,192,103 A 6/1965 Sousa et al.
4,016,170 A 4/1977 Nadelson
(Continued)

FOREIGN PATENT DOCUMENTS

CA 2342432 A1 3/2001
EP 675122 A2 10/1995
(Continued)

OTHER PUBLICATIONS

Stahl et al. Handbook of Pharmaceutical Salts, Wiley & Sons, 2008, p. 215.*

(Continued)

*Primary Examiner* — Matthew Coughlin
(74) *Attorney, Agent, or Firm* — Jones Day

(57) ABSTRACT

Provided herein are pharmaceutical compositions, which comprise a 1,2,4-oxadiazole benzoic acid or a pharmaceutically acceptable salt thereof. Further provided herein are certain pharmaceutically acceptable salts of a 1,2,4-oxadiazole benzoic acid and methods for making the same. Further provided herein are methods of treating or preventing a disease associated with a nonsense mutation or a premature stop codon, comprising administering such pharmaceutical compositions or pharmaceutically acceptable salts to a patient having a disease associated with a nonsense mutation or a premature stop codon.

21 Claims, 37 Drawing Sheets

(56) References Cited

U.S. PATENT DOCUMENTS

| | | | |
|---|---|---|---|
| 4,022,901 A | 5/1977 | Venkatachala et al. | |
| 4,135,910 A | 9/1979 | Howe | |
| 4,166,732 A | 9/1979 | Howe | |
| 4,210,762 A | 7/1980 | Howe | |
| 4,268,299 A | 5/1981 | Howe | |
| 5,484,944 A | 1/1996 | Albaugh et al. | |
| 5,972,050 A | 10/1999 | Wiesenfeldt et al. | |
| 6,034,106 A | 3/2000 | Biftu et al. | |
| 6,071,700 A | 6/2000 | Feng | |
| 6,180,648 B1 | 1/2001 | Kozikowski et al. | |
| 6,472,422 B2 | 10/2002 | Kozikowski et al. | |
| 6,498,151 B2 | 12/2002 | Li et al. | |
| 6,620,828 B2 | 9/2003 | Chu et al. | |
| 6,660,753 B2 | 12/2003 | Van Wagenen et al. | |
| 6,759,538 B2 | 7/2004 | Singh et al. | |
| 6,992,096 B2 * | 1/2006 | Karp | A61K 31/4245 514/364 |
| 7,041,685 B2 | 5/2006 | Cai et al. | |
| 7,112,595 B2 | 9/2006 | Van Wagenen et al. | |
| 7,153,880 B2 | 12/2006 | Singh et al. | |
| 7,202,262 B2 * | 4/2007 | Karp | A61K 31/4245 514/364 |
| 7,304,080 B2 | 12/2007 | Karp et al. | |
| 7,419,991 B2 * | 9/2008 | Karp | A61K 31/4245 514/361 |
| 7,435,750 B2 | 10/2008 | Cai et al. | |
| 7,678,922 B2 * | 3/2010 | Almstead | C07D 271/06 548/125 |
| 7,683,082 B2 * | 3/2010 | Karp | A61K 31/4245 514/364 |
| 7,745,630 B2 | 6/2010 | Bryans et al. | |
| 7,772,259 B2 * | 8/2010 | Karp | A61K 31/4245 514/364 |
| 7,863,456 B2 | 1/2011 | Almstead et al. | |
| 8,017,636 B2 * | 9/2011 | Karp | A61K 31/4245 514/364 |
| 8,101,641 B2 | 1/2012 | Almstead et al. | |
| 8,129,540 B2 | 3/2012 | Karp et al. | |
| 8,163,782 B2 * | 4/2012 | Karp | A61K 31/4245 514/364 |
| 8,227,494 B2 * | 7/2012 | Karp | A61K 31/4245 514/364 |
| 8,299,105 B2 * | 10/2012 | Karp | C07D 285/14 514/364 |
| 8,367,841 B2 * | 2/2013 | Almstead | C07D 271/06 548/125 |
| 8,394,966 B2 | 3/2013 | Almstead et al. | |
| 8,486,982 B2 * | 7/2013 | Karp | A61K 31/4245 514/364 |
| 8,691,511 B2 | 4/2014 | Almstead et al. | |
| 8,716,321 B2 * | 5/2014 | Hirawat | A61K 9/145 514/364 |
| 8,748,625 B2 | 6/2014 | Almstead et al. | |
| 8,796,322 B2 * | 8/2014 | Karp | A61K 31/4245 514/364 |
| 8,815,838 B2 | 8/2014 | Griffith et al. | |
| 8,975,287 B2 * | 3/2015 | Karp | A61K 31/4245 514/364 |
| 9,205,088 B2 * | 12/2015 | Karp | A61K 31/4245 |
| 9,226,919 B2 * | 1/2016 | Hirawat | A61K 31/4245 |
| 9,289,398 B2 * | 3/2016 | Almstead | A61K 31/00 |
| 9,309,206 B2 | 4/2016 | Almstead et al. | |
| 9,474,743 B2 * | 10/2016 | Hirawat | A61K 9/145 |
| 9,522,137 B2 * | 12/2016 | Hirawat | A61K 31/4245 |
| 2002/0147188 A1 | 10/2002 | Marquis et al. | |
| 2004/0204461 A1 * | 10/2004 | Karp | A61K 31/4245 514/364 |
| 2008/0114039 A1 * | 5/2008 | Hirawat | A61K 31/4245 514/364 |
| 2012/0277234 A1 * | 11/2012 | Karp | A61K 31/4245 514/236.2 |
| 2014/0221436 A1 | 8/2014 | Hirawat et al. | |
| 2014/0343009 A1 | 11/2014 | Barth et al. | |
| 2016/0081988 A1 | 3/2016 | Karp et al. | |
| 2016/0101087 A1 | 4/2016 | Hirawat et al. | |

FOREIGN PATENT DOCUMENTS

| | | |
|---|---|---|
| JP | 2001-247569 | 9/2001 |
| JP | 2002-105073 | 4/2002 |
| JP | 2003-81832 | 3/2003 |
| RU | 2398770 C1 | 9/2010 |
| WO | WO 95/11885 | 5/1995 |
| WO | WO 97/09335 | 3/1997 |
| WO | WO 97/41105 | 11/1997 |
| WO | WO 97/44333 | 11/1997 |
| WO | WO 97/46556 | 12/1997 |
| WO | WO 98/00465 | 1/1998 |
| WO | WO 98/33927 | 8/1998 |
| WO | WO 98/45263 | 10/1998 |
| WO | WO 98/49190 | 11/1998 |
| WO | WO 99/21852 | 5/1999 |
| WO | WO 99/54317 | 10/1999 |
| WO | WO 2000/021951 A1 | 4/2000 |
| WO | WO 2000/021959 | 4/2000 |
| WO | WO 2000/025768 | 5/2000 |
| WO | WO 2000/038687 | 7/2000 |
| WO | WO 2000/058278 | 10/2000 |
| WO | WO 2000/058280 | 10/2000 |
| WO | WO 2000/058304 | 10/2000 |
| WO | WO 2000/069810 | 11/2000 |
| WO | WO 2000/075120 | 12/2000 |
| WO | WO 2001/066534 | 9/2001 |
| WO | WO 2001/083464 | 11/2001 |
| WO | WO 2001/085723 | 11/2001 |
| WO | WO 2001/090101 | 11/2001 |
| WO | WO 2002/100826 | 1/2002 |
| WO | WO 2002/072621 | 9/2002 |
| WO | WO 2002/079200 | 10/2002 |
| WO | WO 2002/085869 | 10/2002 |
| WO | WO 2003/002559 | 1/2003 |
| WO | WO 2004/014370 | 2/2004 |
| WO | WO 2004/014902 | 2/2004 |
| WO | WO 2004/072050 | 8/2004 |
| WO | WO 2004/085401 | 10/2004 |
| WO | WO 2004/110351 | 12/2004 |
| WO | WO 2005/060961 | 7/2005 |
| WO | WO 2005/077373 | 8/2005 |
| WO | WO 2006/044682 A1 | 4/2006 |
| WO | WO 2006/110483 A1 | 10/2006 |
| WO | WO 2007/117438 A2 | 10/2007 |
| WO | WO 2007/123848 A2 | 11/2007 |
| WO | WO 2008/030570 A1 | 3/2008 |
| WO | WO 2008/039431 A2 | 4/2008 |
| WO | WO 2008/045566 A1 | 4/2008 |
| WO | WO 2008/127364 A2 | 10/2008 |
| WO | WO 2009/023509 A2 | 2/2009 |
| WO | WO 2009/043889 A2 | 4/2009 |
| WO | WO 2009/054725 A2 | 4/2009 |
| WO | WO 2009/079562 A2 | 6/2009 |
| WO | WO 2010/008831 A2 | 1/2010 |
| WO | WO 2015/188037 | 12/2015 |

OTHER PUBLICATIONS

U.S. Appl. No. 60/149,464, filed Aug. 19, 1999, Van Wagenen et al.
U.S. Appl. No. 60/269,847, filed Feb. 21, 2001, Van Wagenen et al.
U.S. Appl. No. 60/350,107, filed Nov. 2, 2001, Singh et al.
U.S. Appl. No. 60/405,472, filed Aug. 23, 2002, Singh et al.
Announcement by PTC Therapeutics, Inc. and Genzyme Corporation dated Mar. 3, 2010.
Au et al., 1998, "Germ-Line Mutational Analysis of the TSC2 Gene in 90 Tuberouse-Sclerosis Patients," Am. J. Hum. Genet. 62:286-294.
Auld et al., 2009, "Mechanism of PTC124 activity in cell-based luciferase assays of nonsense codon suppression", Proc Natl Acad Sci USA; 106(9):3585-3590.
Auld et al., 2010, "Molecular basis for the high-affinity binding and stabilization of firefly luciferase by PTC124", Proc Natl Acad Sci USA; 107(11):4878-7883.

(56) References Cited

OTHER PUBLICATIONS

Aurino et al., 2006, "Readthrough strategies for stop codons in Duchenne muscular dystrophy", Acta Myologica; 25(1):5-12.
Davies et al., 2008, "Ataluren nonsense mutation suppressor treatment of cystic fibrosis treatment of muscular dystrophy", Drugs of the Future; 33(9):733-736.
Du et al., 2008, "PTC124 is an orally bioavailable compound that promotes suppression of the human CFTR-G542X nonsense allele in a CF mouse model", Proc Natl Acad Sci USA; 105(6):2064-2069.
Gite et al., 2003, "A high-throughput nonisotopic protein truncation test" *Nature Biotechnology* 21:194-197.
Guillonneau et al., 1999, "A nonsense mutation in a novel gene is associated with retinities pigmentosa in a family linked to the RP1 locus" *Human Molecular Genetics* 8:1541-1546.
Hamed et al., 2006, "Drug evaluation: PTC-124—a potential treatment for cystic fibrosis and Duchenne muscular dystrophy", IDrugs; 9(11):783-789.
Hirawat et al., 2007, "Safety, Tolerability, and Pharmacokinetics of PTC124, a Nonaminoglycoside Nonsense Mutation Suppressor, Following Single- and Multiple-Dose Administration to Healthy Male and Female Adult Volunteers," *Journal of Clinical Pharmacology* 47(4):430-444.
Hu et al., 2008, "New approaches to treatment of primary immunodeficiencies: fixing mutations with chemicals"; Curr Opin Allergy Clin Immunol; 8(6):540-546.
Jones et al., 1999, "Comprehensive Mutation Analysis of TSC1 and TSC2—and Phenotypic Correlations in 150 Families with Tuberous Sclerosis," *Am. J. Hum. Genet.* 64:1305-1315.
Jones et al., 2009, "Emerging treatments in cystic fibrosis", Drugs; 69(14):1903-1910.
Kerem et al., 2008, "Effectiveness of PTC124 treatment of cystic fibrosis caused by nonsense mutations: a prospective phase II trial", Lancet; 372(9640):719-727.
Koeberl et al.,1990, "Recurrent nonsense mutations at arginine residues cause severe hemophilia B in unrelated hemophiles" *Hum. Genet.* 84:387-390.
Laake et al., 2000, "Characterization of ATM Mutations in 41 Nordic Families With Ataxia Telangiectasia" *Human Mutation* 16:232-246.
Litjens et al., 2001, "Mucopolysaccharidosis Type VI: Structural and Clinical Implications of Mutations in N-Acetylgalactosamine-4-Sulfatase" *Human Mutation* 18:282-295.
MacDonald et al., 2003, "Design and synthesis of trans-3-(2-(4-((3-(5-methyl1-1,2,4-oxadiazolyl))-phenyl)carboxamido)cycolhexyl)ethyl)-7-methylsulfonyl-2,3,4,5-tetrahydro-1H-3-benzazepine (SB-414796):a potent and selective dopamine D3 receptor antagonist", J Med Chem; 46(23):4952-4964.
Matsuda et al., 2008, "Recent development of read through therapy for muscular dystrophy", Igaku no Ayumi; 226(5):397-401.
Mueller, G., *Chem. Ber.*, 19:1497 (1886).
Ogami et al., 2010, "Research on mRNA degradation and drug discovery", Nihon Yakurigaku Zasshi; 136(3):150-154 (with English Abstract).
Rowe et al., 2009, "Pharmaceuticals targeting nonsense mutations in genetic diseases: progress in development", BioDrugs; 23(3):165-174.
Sands et al., 1993, "A single-base-pair deletion in the β-glucuronidase gene accounts for the phenotype of murine mucopolysaccharidosis type VIII" *Proc. Natl. Acad. Sci. USA* 90:6567-6571.
Schrijver et al., 2002, "Premature Termination Mutations in FBN1: Distinct Effects on Differential Allelic Expression and on Protein and Clinical Phenotypes" *Am. J. Hum. Genet.* 71:223-237.
Sokolenko et al., 1972, Voprosy Khimii I Khimicheskoi Tekhnolugii No. 27:107-112 (with English language abstract).
Strizheva et al., 2001, "The Spectrum of Mutations in TSC1 and TSC2 in Women with Tuberous Sclerosis and Lymphangiomyomatosis," *Am. J. Respir. Crit. Care Med.* 163:253-258.
Supplemental Information from Auld et al., 2009, "Mechanism of PTC124 activity in cell based luciferase assays of nonsense codon suppression," *PNAS Early Edition*:1-6 (pp. 1-17).
Supplementary Information from Welch et al., 2007, "PTC124 Targets Genetic Disorders Caused by Nonsense Mutations," *Nature* 447:87-91 (pp. 1-23).
Sweeney, 2009, "Suppression of premature atop codons for the treatment of a subset of patients with genetic disorders", J Med Sci; 2(1):1-4.
Wakamatsu et al., 1999, "Mutations producing premature termination of translation and an amino acid substitution in the sterol 27-hydroxylase gene cause cerebrotendinous xanthomatosis associated with parkinsonism" *J. Neurol. Neurosurg. Psychiaatry* 67:195-198.
Wang et al., 2010, "Membrane blebbing as an assessment of functional rescue of dysferlin-deficient human myotubes via nonsense suppression", J Appl Physiol; 109(3):901-905.
Welch et al., 2007, "PTC124 Targets Genetic Disorders Caused by Nonsense Mutations," *Nature* 447:87-91.
Wolf et al., 2008, "Don't stop me now! A new active substance with the abbreviation PTC124 targets genetic disorders caused by nonsense mutations", Pharmazie in Unaerer Zeit; 37(5):356-357.
Yogalingam et al., 2001, "Molecular Genetics of Mucopolysaccharidosis Type IIIA and IIIB: Diagnostic, Clinical, and Biological Implications" *Human Mutation* 18:264-281.

\* cited by examiner

Figures 36A-D

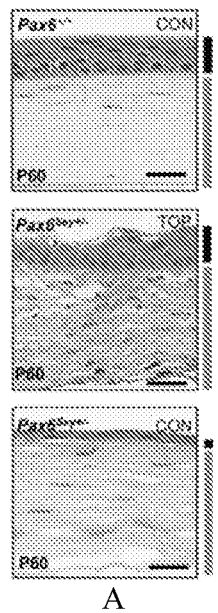
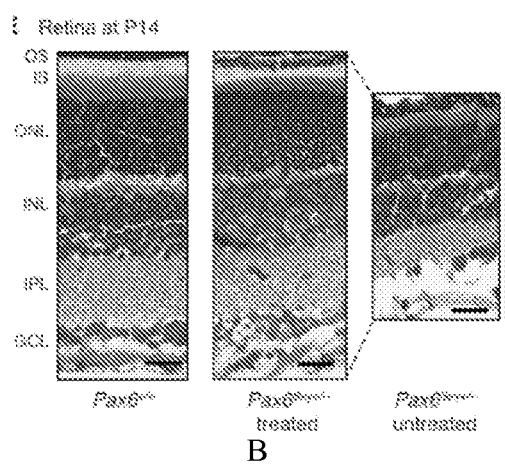
Figures 37

US 9,873,677 B2

PHARMACEUTICAL COMPOSITIONS AND SALTS OF A 1,2,4-OXADIAZOLE BENZOIC ACID

This application is a U.S. national stage application of International Patent Application No. PCT/US2015/018889, filed Mar. 5, 2015, which claims the benefit of priority to U.S. Provisional Application Ser. No. 61/949,052, filed Mar. 6, 2014 and U.S. Provisional Application Ser. No. 62/009,111, filed Jun. 6, 2014, each of which is incorporated herein by reference in its entirety and for all purposes.

1. FIELD

Provided herein are pharmaceutical compositions, which comprise a 1,2,4-oxadiazole benzoic acid or a pharmaceutically acceptable salt thereof. Further provided herein are certain pharmaceutical compositions of a 1,2,4-oxadiazole benzoic acid and methods for making the same. Further provided herein are certain pharmaceutically acceptable salts of a 1,2,4-oxadiazole benzoic acid and methods for making the same. Further provided herein are certain pharmaceutical compositions comprising a 1,2,4-oxadiazole benzoic acid salt and methods for making the same. Further provided herein are methods of treating or preventing an ocular disease associated with a nonsense mutation or a premature stop codon, comprising administering such pharmaceutical compositions or pharmaceutically acceptable salts to a patient having an ocular disease associated with a nonsense mutation or a premature stop codon. Further provided herein are methods of prenatally treating or preventing an ocular disease associated with a nonsense mutation or a premature stop codon, comprising administering such pharmaceutical compositions of a 1,2,4-oxadiazole benzoic acid or pharmaceutical compositions of a pharmaceutically acceptable salt of a 1,2,4-oxadiazole benzoic acid to a patient having an ocular disease associated with a nonsense mutation or a premature stop codon. Further provided herein are methods of postnatally treating or preventing an ocular disease associated with a nonsense mutation or a premature stop codon, comprising administering such pharmaceutical compositions of a 1,2,4-oxadiazole benzoic acid or pharmaceutical compositions of a pharmaceutically acceptable salt of a 1,2,4-oxadiazole benzoic acid to a patient having an ocular disease associated with a nonsense mutation or a premature stop codon.

2. BACKGROUND

U.S. Pat. No. 6,992,096 describes 1,2,4-oxadiazole compounds that are useful for treating, preventing, or managing diseases ameliorated by modulation of premature translation termination or nonsense-mediated mRNA decay, the disclosure of which is incorporated herein by reference in its entirety. One of such compounds is 3-[5-(2-fluoro-phenyl)-[1,2,4]oxadiazol-3-yl]benzoic acid, having the generic name ataluren, or a pharmaceutically acceptable salt thereof, referred to herein as Compound 1. Certain physical properties of Compound 1 can affect the processing, manufacture and pharmaceutical acceptability of an ophthalmic dosage form. The particle size, solubility and flow properties may also affect the efficiency of manufacturing an ophthalmic dosage form of 3-[5-(2-fluoro-phenyl)-[1,2,4]oxadiazol-3-yl]benzoic acid. See, Prescott et al., *Pharm. Tech.* 2000, October, 60-85. Certain formulations of an ophthalmic dosage form of 3-[5-(2-fluoro-phenyl)-[1,2,4]oxadiazol-3-yl]benzoic acid known in the art may remain irritating to the eye. Therefore, there is a need for new pharmaceutical formulations comprising 3-[5-(2-fluoro-phenyl)-[1,2,4]oxadiazol-3-yl]benzoic acid having improved physical and pharmaceutical properties. Furthermore, there is a need for new pharmaceutical formulations comprising salt forms of 3-[5-(2-fluoro-phenyl)-[1,2,4]oxadiazol-3-yl]benzoic acid which have improved physical and pharmaceutical properties.

3. SUMMARY OF THE DISCLOSURE

Provided herein are pharmaceutical compositions comprising 3-[5-(2-fluoro-phenyl)-[1,2,4]oxadiazol-3-yl]benzoic acid in a buffering system, wherein the buffering system solubilizes 3-[5-(2-fluoro-phenyl)-[1,2,4]oxadiazol-3-yl]benzoic acid at a pharmaceutically acceptable pH to provide an improved solution suitable for ocular use. Provided herein are salt forms of 3-[5-(2-fluoro-phenyl)-[1,2,4]oxadiazol-3-yl]benzoic acid, wherein 3-[5-(2-fluoro-phenyl)-[1,2,4]oxadiazol-3-yl]benzoic acid is conjugated with a cationic modifier to provide an ionized salt form of 3-[5-(2-fluoro-phenyl)-[1,2,4]oxadiazol-3-yl]benzoic acid with increased permeability and reduced irritability, wherein the ionized salt form includes a magnesium salt, a potassium salt, a sodium salt, a tromethamine salt, an L-lysine salt, an L-arginine salt, an N-methyl glucamine salt and an L-histidine salt of Compound 1. Further provided herein are pharmaceutical compositions comprising a salt form of 3-[5-(2-fluoro-phenyl)-[1,2,4]oxadiazol-3-yl]benzoic acid in a buffering system, wherein the buffering system solubilizes the salt form of 3-[5-(2-fluoro-phenyl)-[1,2,4]oxadiazol-3-yl]benzoic acid to provide an improved solution of Compound 1 suitable for ocular use.

Further provided herein are pharmaceutical compositions, which comprise 3-[5-(2-fluoro-phenyl)-[1,2,4]oxadiazol-3-yl]benzoic acid, or a pharmaceutically acceptable salt thereof; and one or more additional pharmaceutically acceptable excipients to provide an improved solution suitable for ocular use.

In one aspect, the present disclosure provides a method for preventing, treating, or ameliorating an ocular disease in a mammalian subject in need thereof, the method comprising administering to the subject a therapeutically effective amount of a 3-[5-(2-fluoro-phenyl)-[1,2,4]oxadiazol-3-yl]benzoic acid or a pharmaceutically acceptable salt thereof. In certain embodiments, the method comprises prenatal or postnatal administration, wherein prenatal administration is orally or parenterally and postnatal administration is ocular. In another aspect, the present disclosure provides a method for preventing, treating, or ameliorating an ocular disease in a mammalian subject in need thereof, the method comprising administering to the subject a therapeutically effective amount of a pharmaceutical composition, which comprises 3-[5-(2-fluoro-phenyl)-[1,2,4]oxadiazol-3-yl]benzoic acid or a pharmaceutically acceptable salt thereof and one or more additional pharmaceutically acceptable excipients. In certain embodiments, the method comprises prenatal or postnatal administration, wherein prenatal administration is orally or parenterally and postnatal administration is ocular.

In some embodiments, the therapeutically effective amount of 3-[5-(2-fluoro-phenyl)-[1,2,4]oxadiazol-3-yl]benzoic acid or a pharmaceutically acceptable salt thereof is administered ocularly to one or more regions of the eye. In some embodiments, the therapeutically effective amount of the pharmaceutical composition, which comprises 3-[5-(2-fluoro-phenyl)-[1,2,4]oxadiazol-3-yl]benzoic acid or a pharmaceutically acceptable salt thereof and one or more additional pharmaceutically acceptable excipients, is administered ocularly to one or more regions of the eye.

In some embodiments, the one or more regions of the eye is selected from the group consisting of the posterior chamber, ora serrata, ciliary muscle, ciliary zonules, canal of Schlemm, pupil, anterior chamber, cornea, iris, lens cortex, lens nucleus, ciliary process, conjunctiva, inferior oblique muscle, inferior rectus muscle, medial rectus muscle, retinal arteries and veins, optic disc, dura mater, central retinal artery, central retinal vein, optic nerve, vorticose vein, bulbar sheath, macula, fovea, sclera, choroid, superior rectus muscle, and retina. In some embodiments, the region of the eye is the cornea. In some embodiments, the region of the eye is the fovea. In some embodiments, the region of the eye is the choroid. In some embodiments, the region of the eye is the retina. In some embodiments, the mammal is a human.

In some embodiments, the subject is at risk of having, suspected of having, or diagnosed as having one or more of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

In some embodiments, 3-[5-(2-fluoro-phenyl)-[1,2,4]oxadiazol-3-yl]benzoic acid or a pharmaceutically acceptable salt thereof is administered in combination with at least one additional therapeutic agent. In some embodiments, the additional therapeutic agent is administered before administration of 3-[5-(2-fluoro-phenyl)-[1,2,4]oxadiazol-3-yl] benzoic acid or a pharmaceutically acceptable salt thereof, after administration of 3-[5-(2-fluoro-phenyl)-[1,2,4]oxadiazol-3-yl]benzoic acid or a pharmaceutically acceptable salt thereof, simultaneously with administration of 3-[5-(2-fluoro-phenyl)-[1,2,4]oxadiazol-3-yl]benzoic acid or a pharmaceutically acceptable salt thereof, or a combination thereof.

In some embodiments, the pharmaceutical composition, which comprises 3-[5-(2-fluoro-phenyl)-[1,2,4]oxadiazol-3-yl]benzoic acid or a pharmaceutically acceptable salt thereof and one or more additional pharmaceutically acceptable excipients, is administered in combination with at least one additional therapeutic agent. In some embodiments, the additional therapeutic agent is administered before administration of the pharmaceutical composition, after administration of the pharmaceutical composition, simultaneously with administration of the pharmaceutical composition, or a combination thereof.

Further provided herein are methods for treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

Further provided herein are methods for treating, preventing, or managing an ocular disease associated with a nonsense mutation, comprising administering to a patient having an ocular disease with a nonsense mutation an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

Further provided herein are methods for treating, preventing, or managing an ocular disease associated with a premature stop codon, comprising administering to a patient having an ocular disease associated with a premature stop codon an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

4. BRIEF DESCRIPTION OF THE DRAWINGS

FIGS. 36A-D depict the effects of Compound 1 treatment in PAX6 mutant mice.

Figure 36:
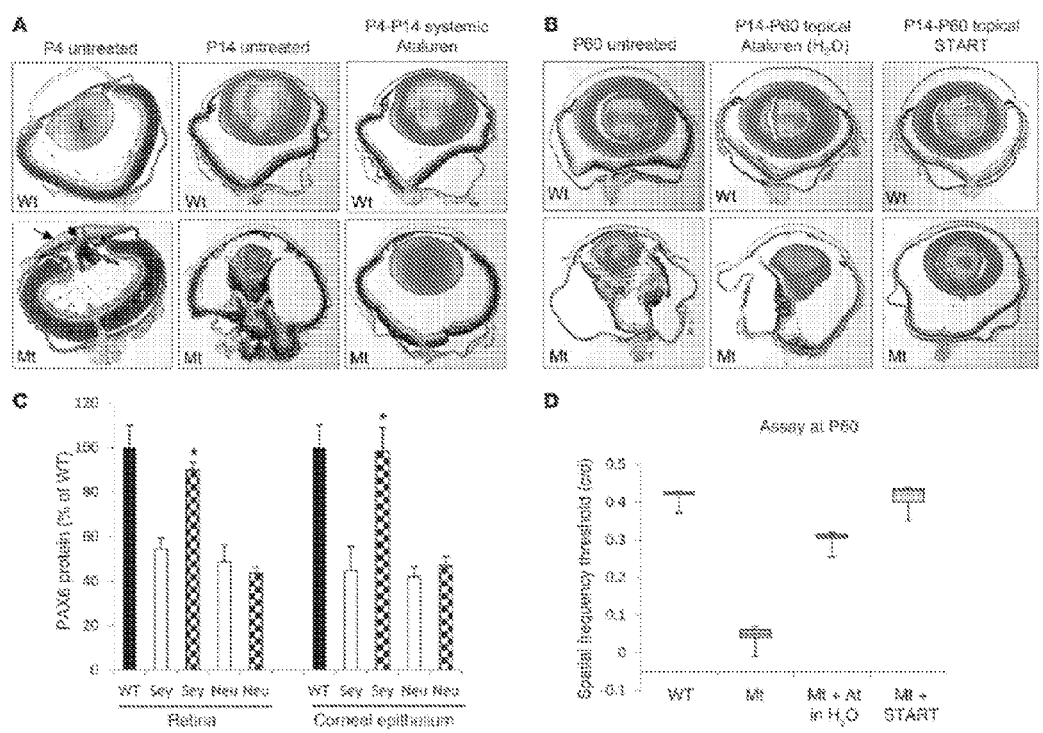

FIG. 36A depicts the effect of systemic Compound 1 treatment in mice with the PAX6 phenotype. The arrowhead indicates the lenticular stalk; the arrow indicates the cornea; and the asterisk indicates the ciliary margin. WT=wild type; Mt=mutant; L=lens; R=retina; P=Postnatal day. FIG. 36B depicts the histological comparison of 1% Compound 1 suspension formulation instilled topically in PAX6 mutant eyes. FIG. 36C depicts PAX6 protein measurements in the retina and corneal epithelia from PAX6 wild type (WT) and PAX6 mutant (SEY and NEU) mice. Black bars depict the wild type mice; white bars depict untreated mice; and checkered bars depict mice after administration of a suspension formulation. * $P<0.001$ (n=6). FIG. 36D provides box-and-whisker plots comparing maximum spatial frequency threshold of topical Compound 1 in water and a suspension formulation. Box-and-whisker plots were prepared showing the 5% and 95% quantiles (whiskers), 25% and 75% quartiles (box) and the median marked by the horizontal line.

FIGS. 37A-B depict the retinal and corneal histology in nmPAX6 (nonsense mutation PAX6) mutant mice. FIG. 37A depicts the results of topical (TOP) treatment with a suspension formulation at Postnatal Day 60 in PAX6 mutant eyes. Untreated PAX6 mutant control (CON) corneal epithelium remains thin at Postnatal Day 60. P refers to postnatal day. FIG. 37B provides an image of retinal sections from wild-type systemically-treated PAX6 mutant mice and untreated mice, showing the photoreceptor inner segments (IS) and outer segments (OS) are shorter in treated mice (n=6). The outer nuclear layers (ONL) are more densely packed in the treated mice compared with those in the wild-type mice. All the retinal layers in the untreated mice are thinner than normal. INL refers to inner nuclear layer; IPL refers to inner plexiform layer; GCL=ganglion cell layer.

5. DETAILED DESCRIPTION

5.1. Definitions

As used herein, the term "premature translation termination" refers to the result of a mutation that changes a codon corresponding to an amino acid to a stop codon.

As used herein, the term "nonsense-mediated mRNA decay" refers to any mechanism that mediates the decay of mRNAs containing a premature translation termination codon. In one embodiment, the nonsense-mediated mRNA decay results from a nonsense mutation of DNA.

As used herein, the term "premature termination codon" or "premature stop codon" refers to the occurrence of a stop codon where a codon corresponding to an amino acid should be.

As used herein, the term "nonsense mutation" refers to a point mutation changing a codon corresponding to an amino acid to a stop codon. In one embodiment, the nonsense mutation is a mutation that occurs in DNA and is then transcribed into mRNA.

As used herein, the term "nonsense suppression" refers to the inhibition or suppression of premature translation termination and/or nonsense-mediated mRNA decay. In one embodiment, the mRNA decay results from a nonsense mutation of DNA.

As used herein, the term "modulation of premature translation termination and/or nonsense-mediated mRNA decay" refers to the upregulation of gene expression in the presence of a nonsense suppression agent. For example, if it is desirable to increase production of a defective protein encoded by a gene with a premature stop codon, i.e., to permit read through of the premature stop codon of the disease gene so translation of the mRNA can occur, then modulation of premature translation termination and/or nonsense-mediated mRNA decay requires the use of a nonsense suppression agent.

As used herein, the terms "adverse effect(s)" and "side effect(s)" include, but are not limited to, nausea, vomiting, diarrhea, headache, dizziness, eye pain, eye swelling, eye burning.

As used herein, the terms "active agent," "drug," and "drug substance" refer to 3-[5-(2-fluoro-phenyl)-[1,2,4]oxadiazol-3-yl]-benzoic acid or a pharmaceutically acceptable salt thereof provided herein (collectively referred to herein as "Compound 1").

As used herein, the term "dose(s)" means a quantity of active agent to be administered at one time.

As used herein, the term "unit dosage form(s)" includes solid dosage forms such as tablets, caplets, capsules, lozenges, dispersions, powders, granules or gels and the like or liquid dosage forms such as solutions suspensions, emulsions or elixirs and the like and solid forms that can be reconstituted to provide such liquid dosage forms, wherein such unit dosage form(s) are suitable for topical (e.g., ocular), oral or parenteral administration to a patient.

As used herein, the terms "dosing regimen" and "dosage(s)" mean the amount of an active agent given per time unit and the duration of administration.

As used herein, the terms "subject" and "patient" are used interchangeably to refer to an animal or any living organism having sensation and the power of voluntary movement, and which requires oxygen and organic food to sustain existence. Non-limiting examples include members of the human, primate, equine, porcine, bovine, leporine, rattus, murine, canine and feline species. In some embodiments, the subject is a mammal or a warm-blooded vertebrate animal. In certain embodiments, the subject is a non-human animal. In specific embodiments, the subject is a human. In certain embodiments, the subject is a fetus, embryo, infant, child, adolescent or adult. In one embodiment, genetic pre-screening has determined that the subject possesses a nonsense mutation. In another embodiment, genetic pre-screening has determined which premature stop codon the patient has (i.e., UAA, UGA, or UAG).

As used herein, the term "effective amount" in the context of a functional read-through protein refers to the amount of the functional read-through protein(s) that has a prophylactic and/or therapeutic benefit to a subject. In specific embodiments, an effective amount of a functional read-through protein is the amount of protein that has in one, two or more of the following effects: (1) prevent the onset, development and/or progression of an ocular condition associated with a nonsense mutation(s), (2) prevent the onset, development and/or progression of one or more symptoms associated with an ocular condition associated with a nonsense mutation(s), (3) reduce the duration and/or severity of an ocular condition associated with a nonsense mutation(s), (4) reduce the number of symptoms associated with an ocular condition associated with a nonsense mutation(s), (5) reduce the duration of one or more symptoms associated with an ocular condition associated with a nonsense mutation(s), (6) reduce the severity of one or more symptoms associated with an ocular condition associated with a nonsense mutation(s) and (7) improve the quality of life of a subject. In a particular embodiment, an effective amount of a functional read-through protein prevents blindness or loss of vision.

As used herein, the term "effective amount" in the context of the administration of a compound described herein refers to the amount of the compound that has a prophylactic and/or therapeutic benefit to a subject. In specific embodiments, an effective amount of a compound described herein that has in one, two or more of the following effects: (1) prevents the onset, development and/or progression of an ocular condition associated with a nonsense mutation(s), (2) prevents the onset, development and/or progression of one or more symptoms associated with an ocular condition associated with a nonsense mutation(s), (3) reduces the duration and/or severity of an ocular condition associated with a nonsense mutation(s), (4) reduces the number of symptoms associated with an ocular condition associated with a nonsense mutation(s), (5) reduces the duration of one or more symptoms associated with an ocular condition associated with a nonsense mutation(s), (6) reduces the severity of one or more symptoms associated with an ocular condition associated with a nonsense mutation(s) and/or (7) improves the quality of life of a subject. In a particular embodiment, an effective amount of a compound described herein prevents blindness or loss of vision. Examples of effective amounts of a compound described herein are provided in Section 5.4, infra.

As used herein, the term "functional" in the context of a functional read-through protein refers to a protein that has enough of the functions of the corresponding wild-type protein to have a beneficial effect in a cell or subject which does not produce or produces insufficient amounts of the wild-type protein as a result of a mutation (e.g., a nonsense mutation) in the nucleic acid sequence (e.g., gene) encoding the protein. In a specific embodiment, the functional read-through protein(s) has one, two, three or more functions of the full-length wild-type protein(s). In certain embodiments, the functional read-through protein(s) produced is a functional non-wild-type protein(s). In certain embodiments, the functional read-through protein(s) produced is a functional wild-type protein(s). In some embodiments, the functional non-wild-type protein produced is full-length. In some embodiments, the functional wild-type protein produced is full-length. In other embodiments, the functional non-wild-type protein(s) is not full-length. In other embodiments, the functional wild-type protein(s) produced is not full-length.

As used herein, the term "ocular disease" or "ocular condition associated with a nonsense mutation in a gene(s)" refers to a disease or condition resulting either directly or indirectly from a nonsense mutation(s) in a gene(s), where the nonsense mutation(s) prevents production of a wild-type protein in an affected cell. Ocular conditions associated with a nonsense mutation encompass diseases in which a single gene contains one, two, three or more nonsense mutations as well as ocular diseases in which two, three or more (multiple) genes contain one, two, three or more nonsense mutations.

As used herein, "in combination" in the context of the administration of therapies refers to the use of more than one therapy. The use of the term "in combination" does not restrict the order in which therapies are administered to a subject with a disease. A first therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to a disease. The therapies are administered to a subject in a sequence and within a time interval such that ophthalmic dosage form(s) described herein can act together with another therapy to provide an increased benefit than if the therapies were administered alone. In certain other embodiments, another therapy may include a co-administered oral or parenteral dosage form.

As used herein, the terms "manage," "managing" and "management" refer to the beneficial effects that a patient derives from the administration of a pharmaceutical composition provided herein comprising 3-[5-(2-fluoro-phenyl)-[1,2,4]oxadiazol-3-yl]benzoic acid or a salt thereof provided herein, which does not result in treating or preventing the disease.

As used herein, the terms "prevent," "preventing" and "prevention" refer to the prevention of the onset, recurrence, spread or worsening of the disease or a symptom thereof in a patient from the administration of a pharmaceutical composition provided herein comprising 3-[5-(2-fluoro-phenyl)-[1,2,4]oxadiazol-3-yl]benzoic acid or a salt thereof provided herein to a patient with such a disease. Since diseases associated with a nonsense mutation have a genetic basis, a patient can be screened for the presence of a nonsense mutation. When it is determined through screening that a patient has a nonsense mutation, an effective amount of a pharmaceutical composition comprising an effective amount of 3-[5-(2-fluoro-phenyl)-[1,2,4]oxadiazol-3-yl]benzoic acid or a salt thereof provided herein can be administered to the patient to prevent the onset, recurrence, spread or worsening of the disease or a symptom thereof.

As used herein, the terms "treat," "treating" and "treatment" refer to the eradication or amelioration of the disease or symptoms associated with the disease. In certain embodiments, such terms refer to minimizing the spread or worsening of the disease in a patient from the administration of a pharmaceutical composition provided herein comprising 3-[5-(2-fluoro-phenyl)-[1,2,4]oxadiazol-3-yl]benzoic acid or a salt thereof provided herein to a patient with such a disease. When it is determined that a patient has a disease associated with a nonsense mutation, an effective amount of a pharmaceutical composition comprising an effective amount of 3-[5-(2-fluoro-phenyl)-[1,2,4]oxadiazol-3-yl]benzoic acid or a salt thereof provided herein can be administered to the patient to eradicate, ameliorate, minimize the spread or worsening of the disease or a symptom thereof.

As used herein, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

5.2. The Compound

A compound for use in the preparation of the pharmaceutical compositions and salts provided herein is 3-[5-(2-fluoro-phenyl)-[1,2,4]oxadiazol-3-yl]-benzoic acid, also referred to by the generic name ataluren, having the structure of Formula (I):

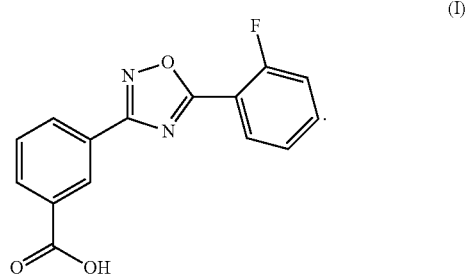 [SMILES: O=C(O)c1cccc(-c2noc(-c3ccccc3F)n2)c1]

(I)

A compound of Formula (I) can be prepared according to the methods described in U.S. Pat. Nos. 6,992,096, 7,678, 922 and 8,367,841, the disclosure of each of which is incorporated by reference herein in its entirety. Alternatively, a salt form of the compound of Formula (I) can be also prepared based upon the teaching herein. The compound of Formula (I) and salts provided herein are collectively referred to as "Compound 1."

In one embodiment, Compound 1 used in the pharmaceutical compositions, processes, and methods provided herein is a free acid. In one embodiment, the free acid is a solid. In another embodiment, the solid free acid is amorphous. In yet another embodiment, the solid free acid is a crystalline form described in U.S. Pat. Nos. 7,863,456, 8,394,966 and 8,748,625 the disclosure of each of which is incorporated by reference herein in its entirety. In yet another embodiment, the solid free acid is a crystalline Form A. In yet another embodiment, the solid free acid is a crystalline Form B. These solid forms of the compound of Formula (I) can also be prepared according to the methods described in U.S. Pat. Nos. 7,863,456, 8,394,966 and 8,748,625 the disclosure of each of which is incorporated by reference herein in its entirety. Alternatively, the solid forms of the compound of Formula (I) can be also prepared according to other methods apparent to those of skill in the art based upon the teaching herein.

In another embodiment, the free acid of the compound of Formula (I) is a pharmaceutically acceptable solvate. In one embodiment, the free acid is a hydrate. In another embodiment, the compound of Formula (I) is a pharmaceutically acceptable anhydrous form. In another embodiment, the free acid of the compound of Formula (I) is a pharmaceutically acceptable cocrystal form such as a chelate, clathrate or a complex with DEAE-C (diethylaminoethyl-cellulose), DEAE-D (diethylaminoethyl-dextran) or a cyclodextrin. In certain embodiments, the cyclodextrin is selected from α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin.

In yet another embodiment, Compound 1 used in the pharmaceutical compositions, processes, and methods provided herein is a pharmaceutically acceptable free acid of the compound of Formula (I). In another embodiment, Compound 1 used in the pharmaceutical compositions, processes, and methods provided herein is a pharmaceutically acceptable salt of the compound of Formula (I). In another embodiment, Compound 1 used in the pharmaceutical compositions, processes, and methods provided herein is a pharmaceutically acceptable anhydrous free acid or salt of the compound of Formula (I).

5.3. Salt Forms and Preparation Thereof

Provided herein are salt forms of Compound 1, comprising a salt selected from L-arginine, L-histidine, L-lysine, magnesium methoxide, potassium hydroxide, sodium hydroxide or tromethamine. More particularly, salt forms of Compound 1 comprise a salt selected from L-lysine, sodium or tromethamine. Also provided herein are evaporation methods for preparing in situ salt forms of Compound 1, comprising the steps of (1) mixing a solution of a salt and a solution of Compound 1; (2) evaporating the mixed solution under a gas flow with a certain flow rate at a particular temperature to yield a salt form; and (3) collecting the salt form.

In one embodiment, the solvent used to prepare the solution of the salt is selected from acetone, ethanol, THF, methanol, water, dichloromethane or mixtures thereof. In one embodiment, the salt is selected from a L-arginine, L-histidine, L-lysine, magnesium, potassium, sodium or tromethamine salt. In certain embodiments, the salt is selected from a L-lysine, sodium or tromethamine salt. In certain embodiments, the Compound 1 free acid may be found to be irritating. When conjugated with a cationic modifier selected from L-arginine, L-histidine, L-lysine, magnesium, potassium, sodium or tromethamine; or, with a complexing agent selected from DEAE-C, DEAE-D or a cyclodextrin, the resulting ion-neutral form of 3-[5-(2-fluoro-phenyl)-[1,2,4]oxadiazol-3-yl]benzoic acid has increased permeability to ocular membranes and provides reduced irritability to the eye surface. The conjugated or complexed carboxylic acid of Compound 1 is unable to bind to ionic sites on the surface of the eye and, thus, irritability is reduced and permeability is increased. Other embodiments include a cyclodextrin selected from α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin. In certain embodiments, the cationic modifier is present in a range of from about 0.01% to about 5.0% w/v, about 0.5% to about 5.0% w/v, about 0.1% to about 5.0% w/v, about 0.01% to about 2.0% w/v, about 0.5% to about 2.0% w/v or about 0.1% to about 2.0% w/v. In certain embodiments, the complexing agent is present in a range of from about 0.01% to about 10.0% w/v, about 0.5% to about 10.0% w/v, about 0.1% to about 10.0% w/v, about 0.01% to about 2.0% w/v, about 0.5% to about 2.0% w/v or about 0.1% to about 2.0% w/v.

In one embodiment, the solvent used to prepare the solution of Compound 1 is selected from acetone, ethanol, THF, methanol, water, dichloromethane or mixtures thereof. In one embodiment, the gas is nitrogen. In one embodiment, the flow rate of the gas used for evaporation is about 0.4 L/minute. In one embodiment, the particular temperature is about 25° C. In one embodiment, the volume of each mixed solution is about 200 μL. In one embodiment, the salt solution concentration is in a range of from about 0.005 mol/L to about 0.250 mol/L; or, more particularly, about 0.008 mol/L, about 0.028 mol/L, about 0.050 mol/L or about 0.230 mol/L.

In one embodiment, the salt solution concentration for use with Compound 1 is in a range of from about 0.0025 mol/L to about 0.075 mol/L; or, more particularly, about 0.004 mol/L, about 0.011 mol/L, or about 0.050 mol/L. In one embodiment, the stoichiometric equivalence of Compound 1:salt is about 1:1, about 1:1.15, about 1:1.25, about 1:1.5, about 1:1.66, about 1:2, about 1:2.5, about 1:3, about 1:4 or about 1:5.

In one embodiment, the mass ratio between the salt and Compound 1 is about 1.25, about 1.5, about 1.66, about 2, about 2.5, about 3, about 4 or about 5. In one embodiment, the total mass of the salt and Compound 1 in a 200 μL mixed solution is about 0.001 mg, about 0.0015 mg, about 0.002 mg, about 0.0025 mg, about 0.003 mg, about 0.004 mg, about 0.005 mg, about 0.006 mg, about 0.007 mg, about 0.008 mg, about 0.009 mg, about 0.01 mg, about 0.015 mg, about 0.02 mg, about 0.025 mg, about 0.03 mg, about 0.04 mg, about 0.05 mg, about 0.06 mg, about 0.07 mg, about 0.08 mg, about 0.09 mg, about 0.1 mg, about 0.15 mg, about 0.2 mg, about 0.25 mg, about 0.3 mg, about 0.4 mg, about 0.5 mg, about 0.6 mg, about 0.7 mg, about 0.8 mg, about 0.9 mg or about 1.0 mg.

Provided herein is a salt form comprising 3-[5-(2-fluoro-phenyl)-[1,2,4]oxadiazol-3-yl]benzoic acid and a salt selected from the group consisting of a magnesium salt, a potassium salt, a sodium salt, a tromethamine salt, an L-lysine salt, an L-arginine salt, an N-methyl glucamine salt and an L-histidine salt. Provided herein is a salt form comprising 3-[5-(2-fluoro-phenyl)-[1,2,4]oxadiazol-3-yl]benzoic acid and a salt selected from the group consisting of a tromethamine salt and an L-lysine salt.

Further provided herein are slurry methods for preparing salt forms of Compound 1, comprising the steps of (1) mixing a salt and Compound 1 in a solvent; (2) evaporating the mixture under a gas flow with a certain flow rate at a particular temperature for a period of time to yield a salt form; and (3) collecting the salt form. In one embodiment, the solvent used to prepare the mixture is selected from ethyl acetate, 2-propanol, t-butyl methyl ether, toluene or mixtures thereof. In one embodiment, the gas is nitrogen. In one embodiment, the gas flow rate is about 0.4 L/minute. In one embodiment, the particular temperature is about 25° C. In one embodiment, the period of time is about 2 days.

Further provided herein are precipitation methods for preparing salt forms of Compound 1, comprising the steps of (1) adding a solution of a salt into a solution of Compound 1; (2) evaporating the mixture under a gas flow with a certain flow rate at a particular temperature for a period of time to yield a salt form; and (3) collecting the salt. In one embodiment, the solvent used to prepare the solution of the salt is water. In one embodiment, the solvent used to obtain the solution of Compound 1 is THF. In one embodiment, the gas is nitrogen. In one embodiment, the gas flow rate is about 80 mL/minute. In one embodiment, the particular temperature is about 25° C. In one embodiment, the period of time is about 2 days.

5.3.1. Compound 1 Magnesium Salt

In one embodiment, provided herein is a magnesium salt of Compound 1.

In one embodiment, the magnesium salt of Compound 1 is a solid form of Compound 1. In another embodiment, the magnesium salt is amorphous. In another embodiment, the magnesium salt is crystalline.

In certain embodiments, the magnesium salt provided herein is obtained by evaporation methods. In certain embodiments, the magnesium salt is obtained from certain solvent systems including a mixture of MeOH and $CH_2Cl_2$ (such as about 1:3 v/v). In one embodiment, the magnesium salt obtained from a mixture of MeOH and $CH_2Cl_2$ is amorphous.

In certain embodiments, the magnesium salt provided herein is obtained by precipitation methods. In one embodiment, the solvent of the solution of the salt former is water. In one embodiment, the solvent of the solution of Compound 1 is THF. In one embodiment, the magnesium salt obtained from a mixture of THF and water is crystalline.

In one embodiment, the magnesium salt is a 4 molar water solvate.

In one embodiment, the stoichiometric ratio of the magnesium salt for Compound 1:Magnesium is about 1:0.5.

Figure 2:
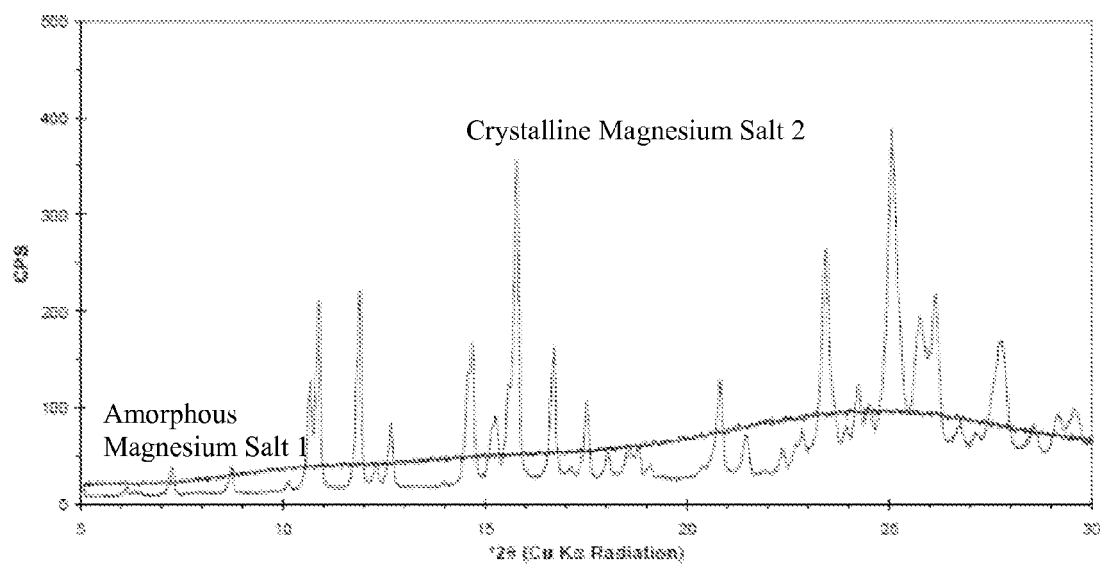
FIG. 2 depicts a Powder X-Ray Diffraction (PXRD) pattern of a Compound 1 magnesium salt 1 as an amorphous form compared to formation of a crystalline magnesium salt 2.

In certain embodiments, a solid form provided herein, e.g., a magnesium salt, is substantially crystalline, as indicated by, e.g., X-ray powder diffraction measurements. In one embodiment, the magnesium salt has an X-ray powder diffraction pattern substantially as shown in FIG. 2.

Figure 1:
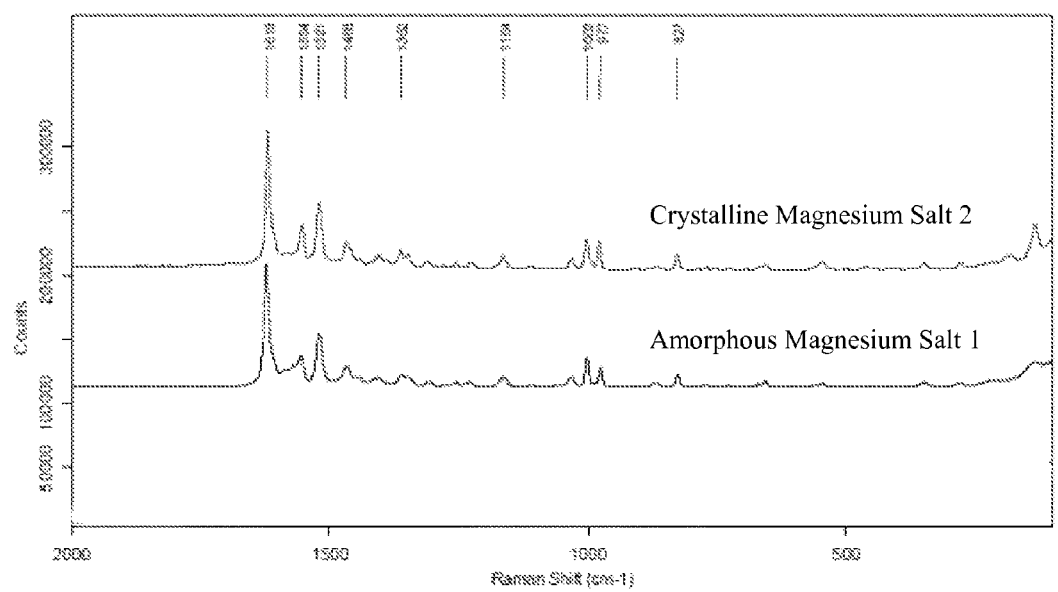
FIG. 1 depicts Raman spectra of a Compound 1 magnesium salt 1 as an amorphous form compared to formation of a crystalline magnesium salt 2.

In one embodiment, provided herein is a magnesium salt having Raman spectra substantially as depicted in FIG. 1.

5.3.2. Compound 1 Potassium Salt

In one embodiment, provided herein is a potassium salt of Compound 1.

In one embodiment, the potassium salt of Compound 1 is a solid form of Compound 1. In another embodiment, the potassium salt is crystalline.

In certain embodiments, the potassium salt provided herein is obtained by evaporation methods. In certain embodiments, the potassium salt is obtained from certain solvent systems including a mixture of THF and water (such as about 5:1 v/v).

Figure 4:
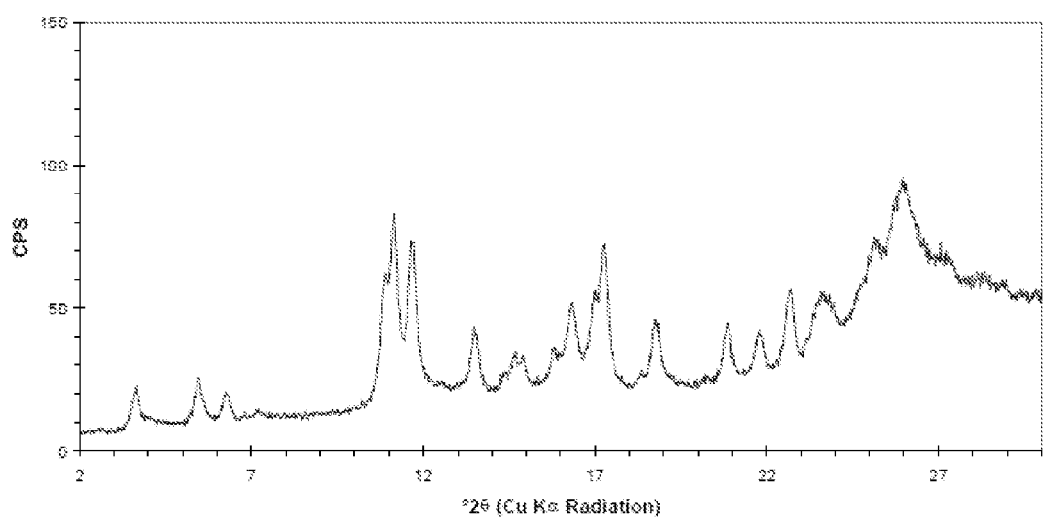
FIG. 4 depicts a PXRD pattern of a Compound 1 potassium salt 1.

In certain embodiments, a solid form provided herein, e.g., a potassium salt, is substantially crystalline, as indicated by, e.g., X-ray powder diffraction measurements. In one embodiment, the potassium salt has an X-ray powder diffraction pattern substantially as shown in FIG. 4.

Figure 3:
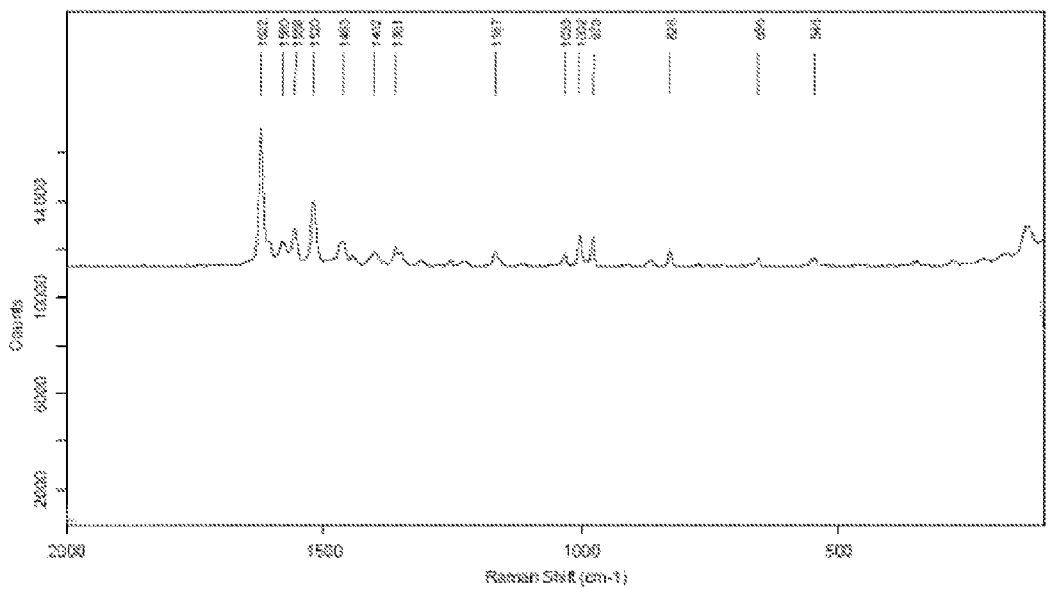
FIG. 3 depicts Raman spectra of a Compound 1 potassium salt 1.

In one embodiment, provided herein is a potassium salt having Raman spectra substantially as depicted in FIG. 3.

5.3.3. Compound 1 Sodium Salt

In one embodiment, provided herein is a sodium salt of Compound 1.

In one embodiment, the sodium salt of Compound 1 is a solid form of Compound 1. In another embodiment, the sodium salt is crystalline.

In certain embodiments, the sodium salt provided herein is obtained by evaporation methods. In certain embodiments, the sodium salt is obtained from certain solvent systems including a mixture of ethanol and water (such as about 8:1 v/v).

In one embodiment, the sodium salt is a 1.5 molar water solvate.

In one embodiment, the stoichiometric ratio of the sodium salt for Compound 1:sodium is about 1:1.

Figure 6:
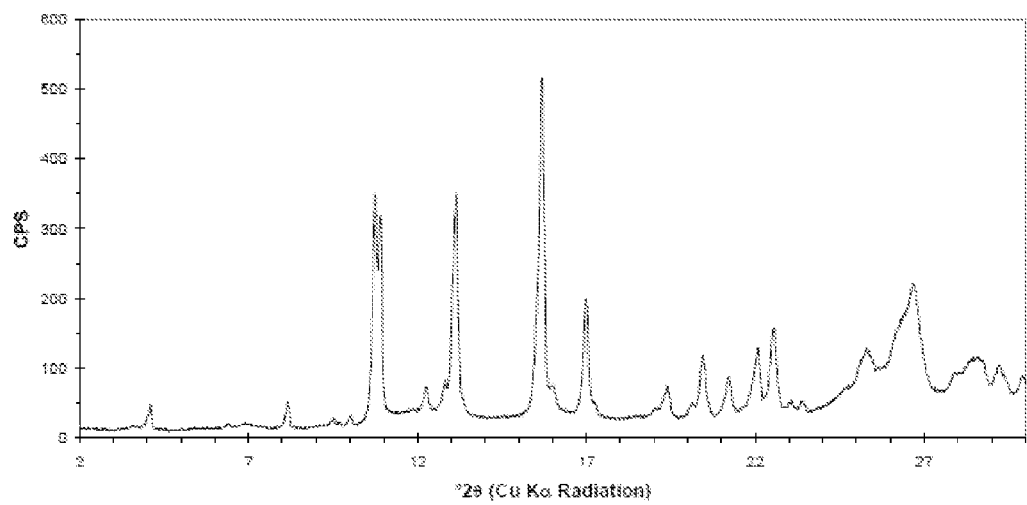
FIG. 6 depicts a PXRD pattern of a Compound 1 sodium salt 1.

In certain embodiments, a solid form provided herein, e.g., a sodium salt, is substantially crystalline, as indicated by, e.g., X-ray powder diffraction measurements. In one embodiment, the sodium salt has an X-ray powder diffraction pattern substantially as shown in FIG. 6.

Figure 5:
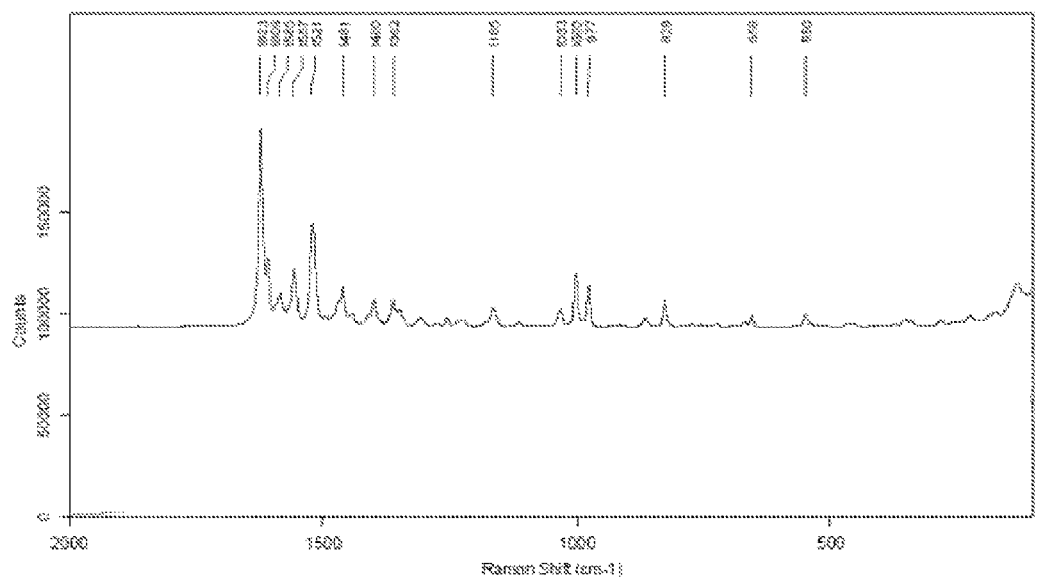
FIG. 5 depicts Raman spectra of a Compound 1 sodium salt 1.

In one embodiment, provided herein is a sodium salt having Raman spectra substantially as depicted in FIG. 5.

5.3.4. Compound 1 Tromethamine Salt

In one embodiment, provided herein is a tromethamine salt of Compound 1.

In one embodiment, the tromethamine salt of Compound 1 is a solid form of Compound 1. In another embodiment, the tromethamine salt is crystalline.

In certain embodiments, the tromethamine salt provided herein is obtained by evaporation methods. In certain embodiments, the tromethamine salt is obtained from certain solvent systems including a mixture of acetone and methanol (such as about 10:1 v/v) or a mixture of water and methanol (such as about 1:1 v/v).

In one embodiment, the stoichiometric ratio of the tromethamine salt for Compound 1:tromethamine is about 1:0.5 in a 0.5:0.5 methanol:water mixture.

Figure 8:
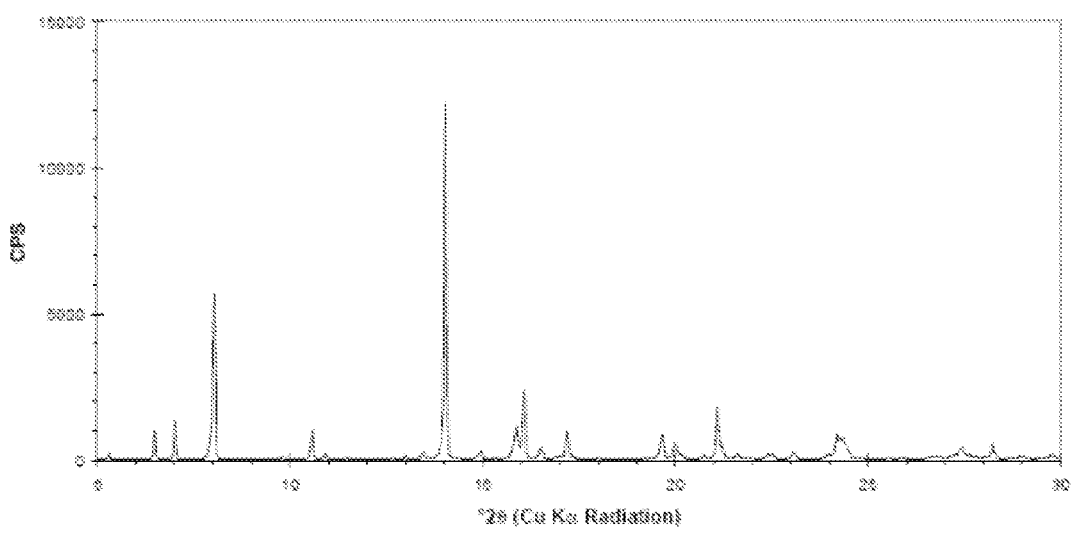
FIG. 8 depicts a PXRD pattern of a Compound 1 tromethamine salt 1.

In certain embodiments, a solid form provided herein, e.g., a tromethamine salt, is substantially crystalline, as indicated by, e.g., X-ray powder diffraction measurements. In one embodiment, the tromethamine salt has an X-ray powder diffraction pattern substantially as shown in FIG. 8.

Figure 7:
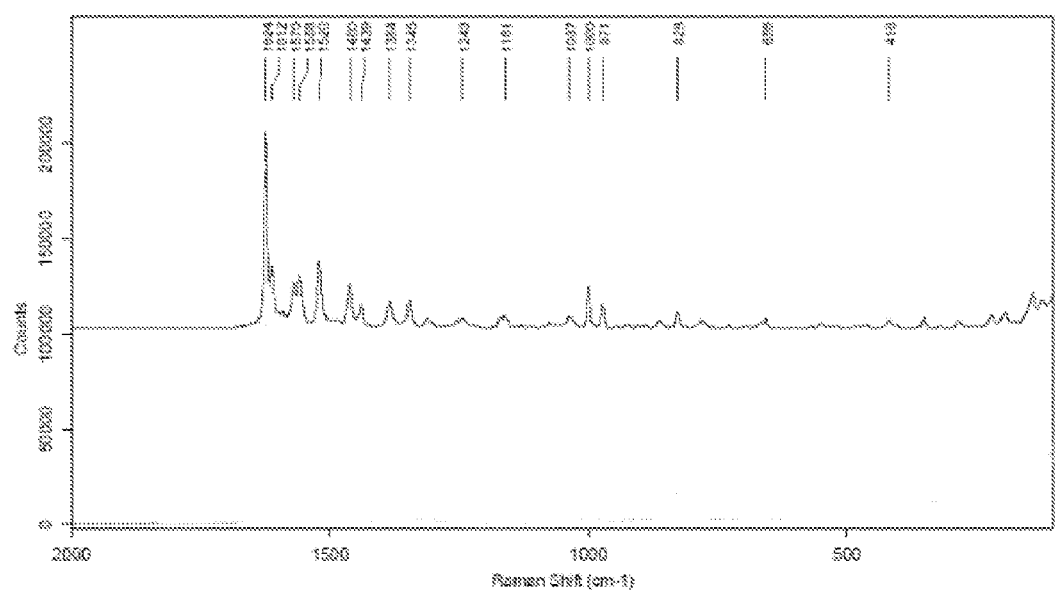
FIG. 7 depicts Raman spectra of a Compound 1 tromethamine salt 1.

In one embodiment, provided herein is a tromethamine salt having Raman spectra substantially as depicted in FIG. 7.

Figure 9:
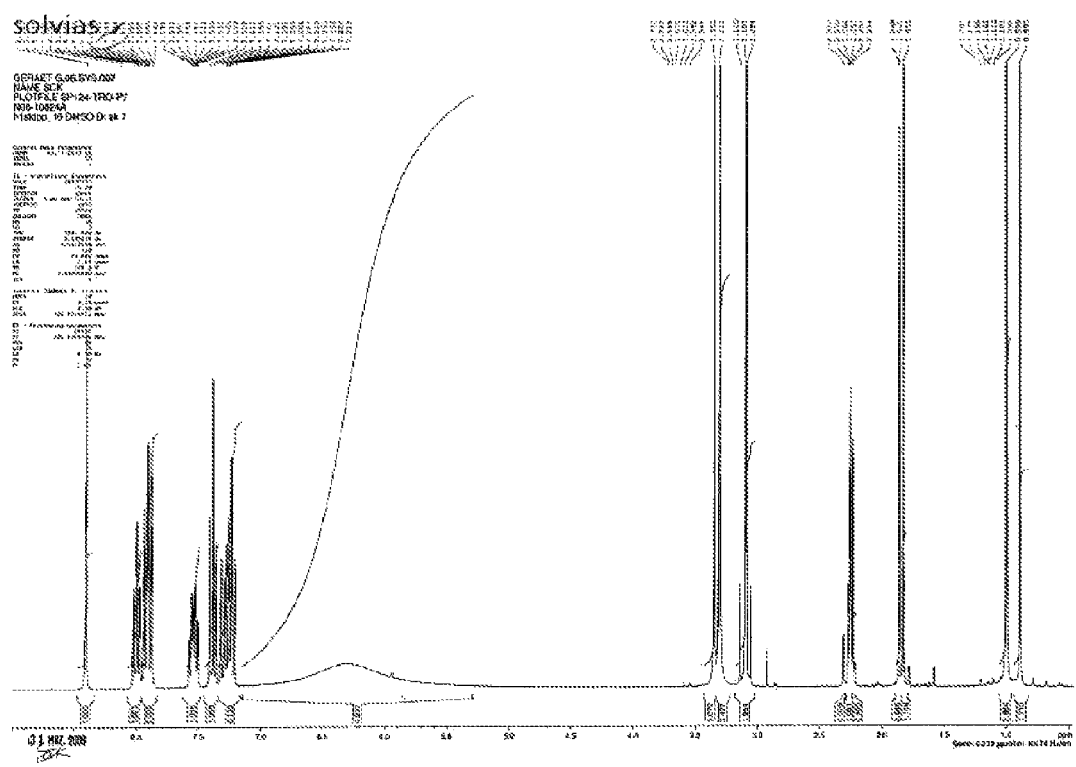
FIG. 9 depicts a $^1$H-NMR spectrum of a Compound 1 tromethamine salt 1.

In one embodiment, provided herein is a tromethamine salt having $^1$H NMR substantially as depicted in FIG. 9.

Figure 19:
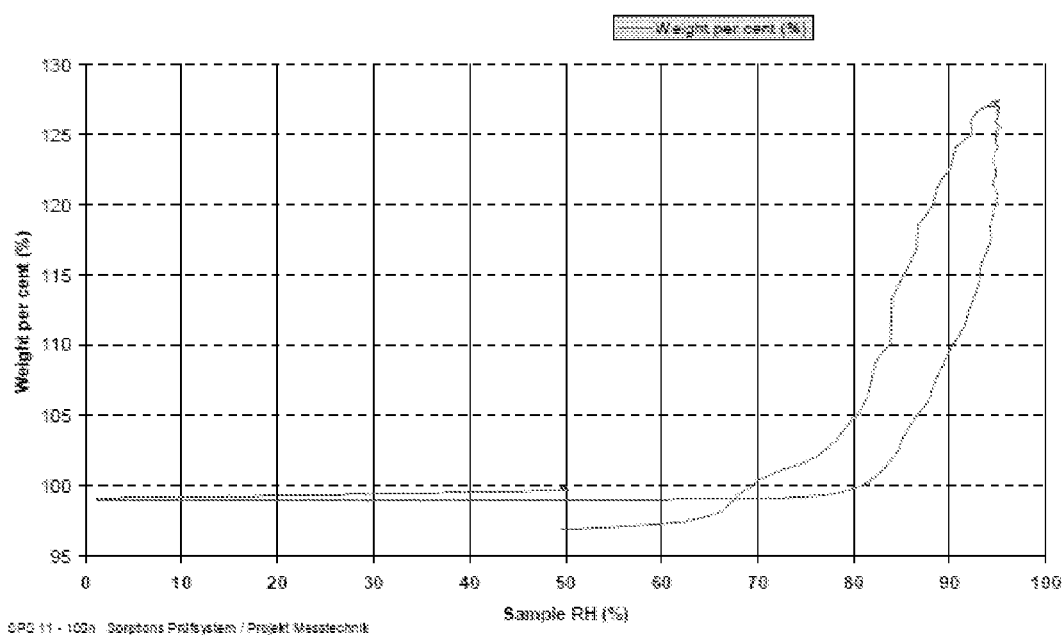
FIG. 19 depicts a DVS of a Compound 1 tromethane salt 1 that shows a large reversible water uptake with hysteresis arriving at lower mass than originally.

In one embodiment, provided herein is a tromethamine salt having DVS substantially as depicted in FIG. 19. In one embodiment, the DVS result shows about 2% overall weight loss. In one embodiment, the DVS result shows about 3% overall weight loss. In one embodiment, the DVS result shows about 4% overall weight loss.

5.3.5. Compound 1 L-Lysine Salt

In one embodiment, provided herein is an L-lysine salt of Compound 1.

In one embodiment, the L-lysine salt of Compound 1 is a solid form of Compound 1. In another embodiment, the L-lysine salt is crystalline.

In certain embodiments, the L-lysine salt provided herein is obtained by evaporation methods. In certain embodiments, the L-lysine salt is obtained from certain solvent systems including a mixture of THF and water (such as about 5:1 v/v).

In one embodiment, the stoichiometric ratio of the L-lysine salt for Compound 1:L-lysine is about 1:1.

Figure 12:
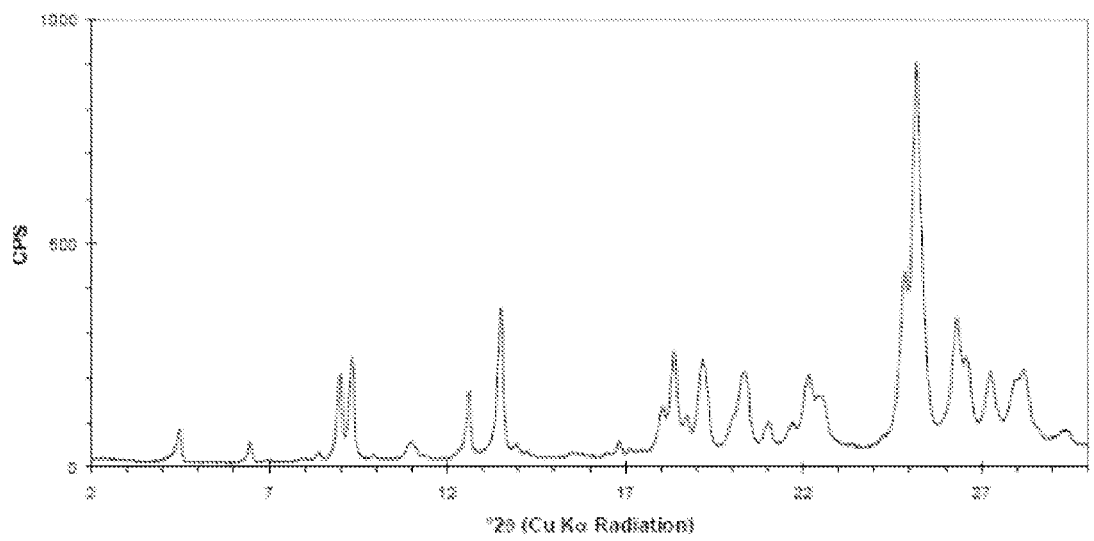
FIG. 12 depicts a PXRD pattern of a Compound 1 L-lysine salt 1.

In certain embodiments, a solid form provided herein, e.g., an L-lysine salt, is substantially crystalline, as indicated by, e.g., X-ray powder diffraction measurements. In one embodiment, the L-lysine salt has an X-ray powder diffraction pattern substantially as shown in FIG. 12.

Figure 11:
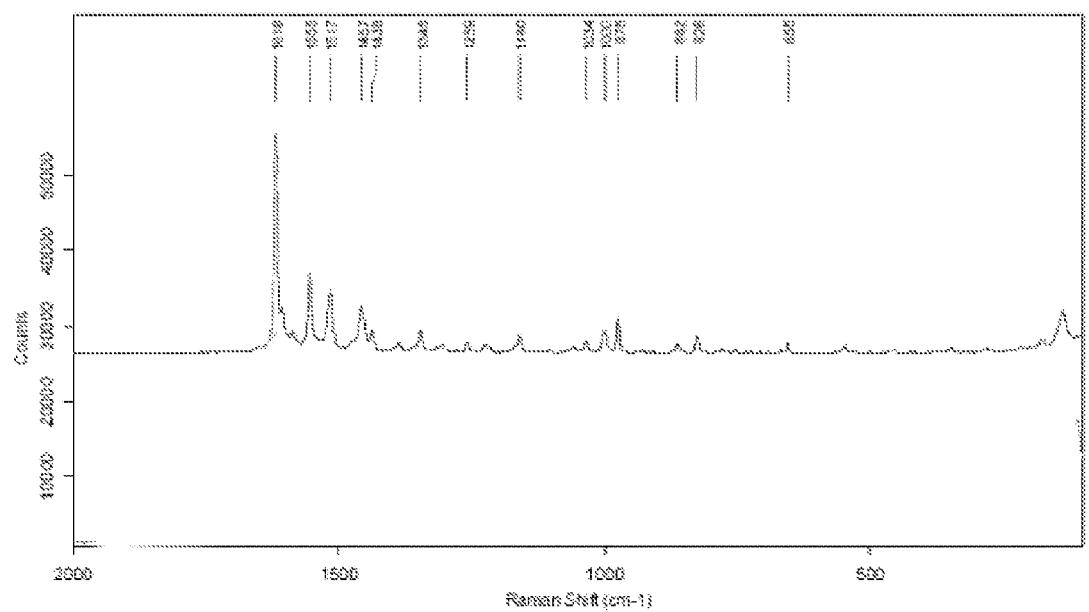
FIG. 11 depicts Raman spectra of a Compound 1 L-lysine salt 1.

In one embodiment, provided herein is an L-lysine salt having Raman spectra substantially as depicted in FIG. 11.

5.3.6. Compound 1 L-Arginine Salt

In one embodiment, provided herein is an L-arginine salt of Compound 1.

In one embodiment, the L-arginine salt of Compound 1 is a solid form of Compound 1. In another embodiment, the L-arginine salt is crystalline.

In certain embodiments, the L-arginine salt provided herein is obtained by evaporation methods. In certain embodiments, the L-arginine salt is obtained from certain solvent systems including a mixture of ethanol and water (such as about 10:1 v/v).

Figure 14:
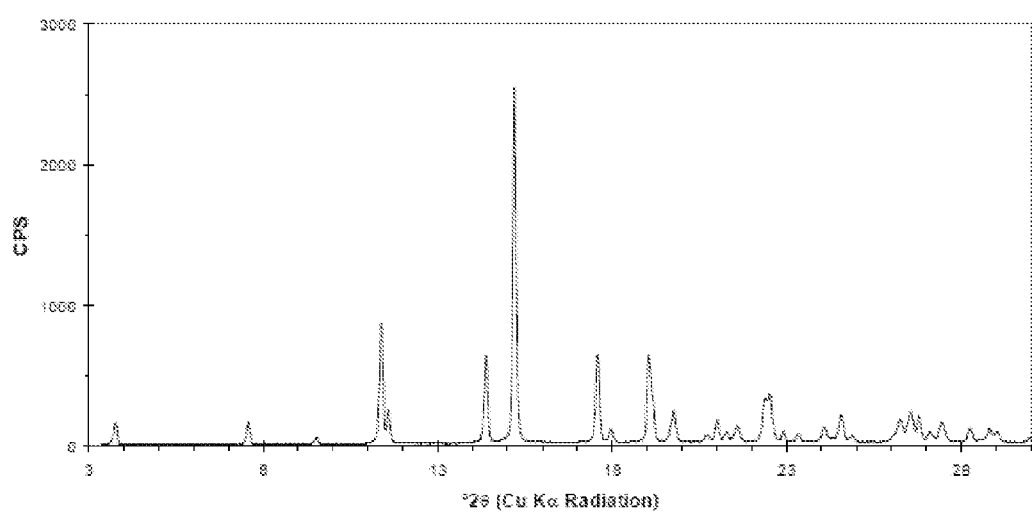
FIG. 14 depicts a PXRD pattern of a Compound 1 L-arginine salt.

In certain embodiments, a solid form provided herein, e.g., an L-arginine salt, is substantially crystalline, as indicated by, e.g., X-ray powder diffraction measurements. In one embodiment, the L-arginine salt has an X-ray powder diffraction pattern substantially as shown in FIG. 14.

Figure 13:
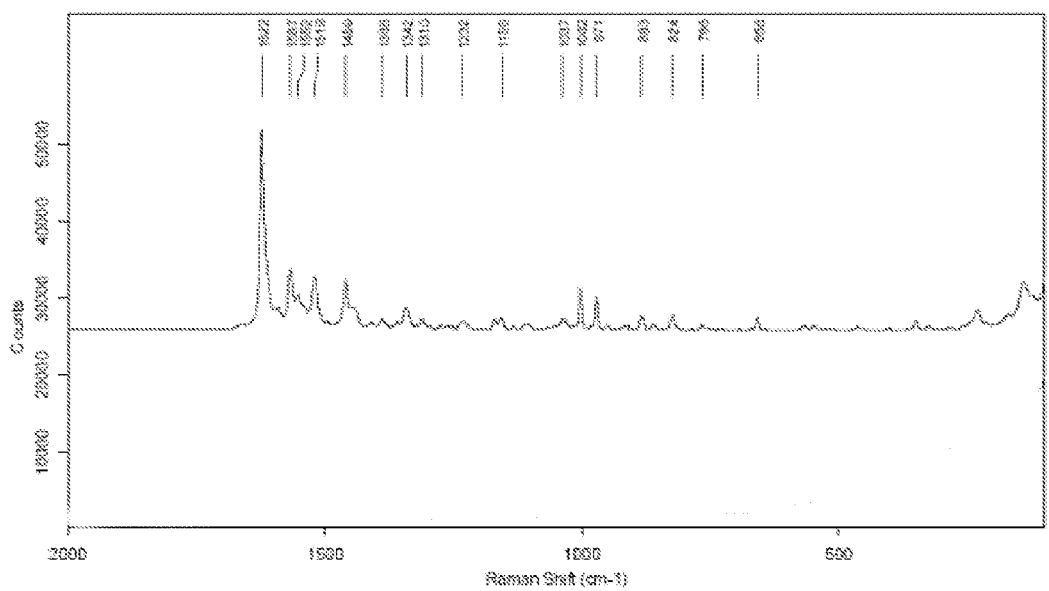
FIG. 13 depicts Raman spectra of a Compound 1 L-arginine salt.

In one embodiment, provided herein is an L-arginine salt having Raman spectra substantially as depicted in FIG. 13.

5.3.7. Compound 1 L-Histidine Salt

In one embodiment, provided herein is an L-histidine salt of Compound 1.

In one embodiment, the L-histidine salt of Compound 1 is a solid form of Compound 1. In another embodiment, the L-histidine salt is crystalline.

In certain embodiments, the L-histidine salt provided herein is obtained by evaporation methods. In certain embodiments, the L-histidine salt is obtained from certain solvent systems including a mixture of THF and water (such as about 5:1 v/v).

Figure 16:
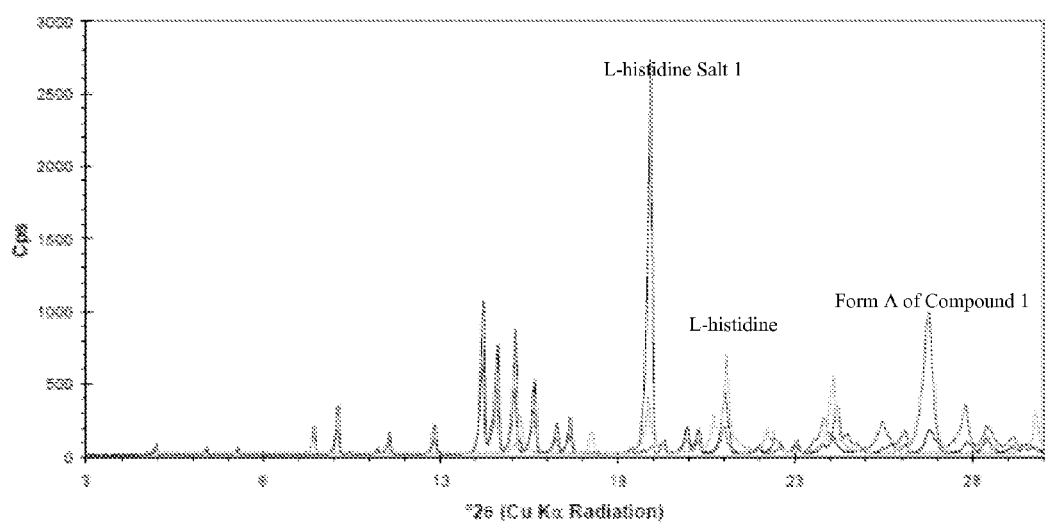
FIG. 16 depicts a PXRD pattern of a Compound 1 L-histidine salt 1 superposed on Form A of Compound 1 and L-histidine, showing Compound 1 peaks and overlapping peaks of L-histidine salt 1 with L-histidine.

In certain embodiments, a solid form provided herein, e.g., an L-histidine salt, is substantially crystalline, as indicated by, e.g., X-ray powder diffraction measurements. In one embodiment, the L-histidine salt has an X-ray powder diffraction pattern substantially as shown in FIG. 16.

Figure 15:
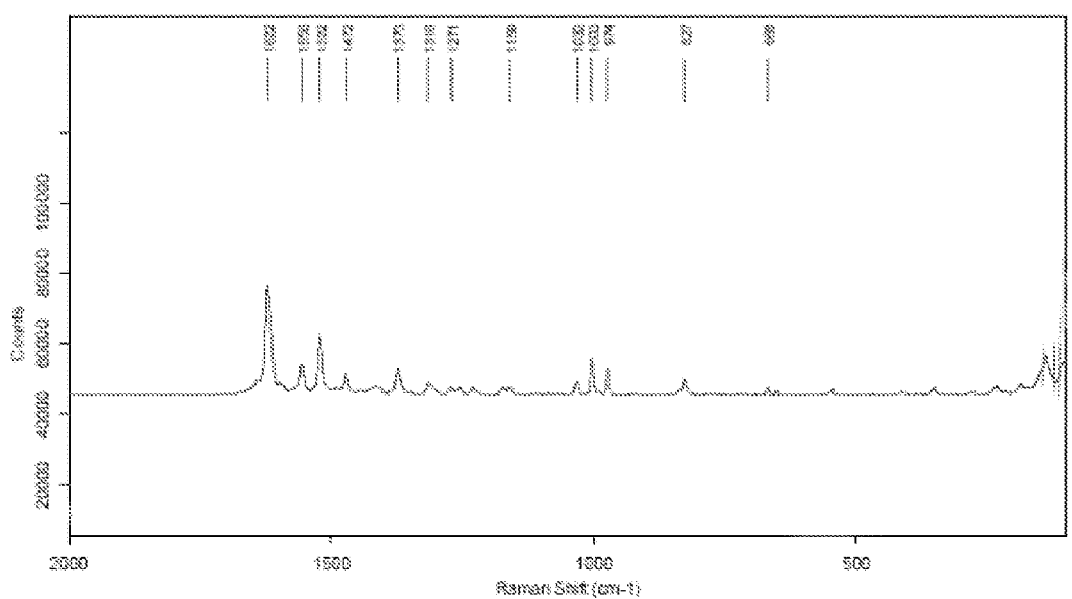
FIG. 15 depicts Raman spectra of a Compound 1 L-histidine salt 1.

In one embodiment, provided herein is an L-histidine salt having Raman spectra substantially as depicted in FIG. 15.

5.4. Pharmaceutical Compositions

Pharmaceutical compositions and single unit dosage forms comprising an effective amount of Compound 1 can be used in the methods provided herein. Individual dosage forms may be suitable for oral, dermal, mucosal (including, without limitation, ophthalmic, sublingual, buccal, rectal, nasal, or vaginal) or parenteral administration (including, without limitation, subcutaneous, intramuscular, intraarterial, intraperitoneal, intrathecal, intraventricular, intraurethral, intrasternal, intracranial, intrasynovial, intravesical, intravitreous, intraocular, intracorneal or intravenous and any another similar injection or infusion technique). Preferred pharmaceutical compositions and single unit dosage forms are suitable for oral administration. In certain embodiments, prenatal administration of Compound 1 may be via a oral or parenteral route. In certain embodiments, Compound 1 may be prenatally administered orally, such as in a tablet or capsule dosage form. In certain other embodiments, Compound 1 may be prenatally administered parenterally, such as via an intravenous dosage form. In certain embodiments, Compound 1 may be postnatally administered topically, orally, or parenterally. In certain embodiments, Compound 1 may be postnatally administered topically. using a dosage form such as a topical ophthalmic dosage form (e.g., a topical gel or eye drop solution).

In certain embodiments, the pharmaceutical composition comprises from about 0.1% to about 99%, from about 5% to about 90%, from about 5% to about 50%, from about 10% to about 40%, from about 20% to about 30%, from about 0.1% to about 5%, from about 0.1% to about 2.5%, from about 0.1% to about 1% or from about 0.25% to about 0.5% by weight/volume (w/v) of Compound 1. In certain embodiments, the pharmaceutical composition comprises about 0.01%, about 0.02%, about 0.025%, about 0.05%, about 0.1%, about 0.15%, about 0.2%, about 0.25%, about 0.5%, about 1%, about 2%, about 5%, about 10%, about 15%, about 20%, about 25%, about 30%, about 35%, about 40%, about 50%, about 60%, about 70%, about 80%, or about 90% by weight of Compound 1. In certain embodiments, the pharmaceutical composition comprises about 0.05%, about 0.1%, about 0.2%, about 0.25%, about 0.5% or about 1% by weight of Compound 1. In other embodiments, the pharmaceutical composition comprises about 0.05%, about 0.1%, about 0.2% or about 0.5% by weight of Compound 1.

In certain embodiments, the pharmaceutical composition provided herein comprises from about 1 to 5,000 mg, from about 10 to about 2,000 mg, from about 50 to about 1,000 mg, from about 100 to about 1,000 mg, or from about 100 to about 500 mg of Compound 1. In certain embodiments, the pharmaceutical composition provided herein comprises about 125 mg, about 200 mg, about 250 mg, about 325 mg, about 400 mg, about 500 mg, or about 1000 mg of Compound 1. In certain embodiments, the pharmaceutical composition provided herein comprises about 120 mg, about 130 mg, about 195 mg, about 205 mg, about 245 mg, about 255 mg, about 320 mg, about 330 mg, about 395 mg, about 405 mg, about 495 mg, about 505 mg, about mg 995, or about 1005 mg of Compound 1.

In certain embodiments, Compound 1 in the pharmaceutical compositions provided here is the free acid of 3-[5-(2-fluoro-phenyl)-[1,2,4]oxadiazol-3-yl]-benzoic acid or a salt of 3-[5-(2-fluoro-phenyl)-[1,2,4]oxadiazol-3-yl]-benzoic acid provided herein.

The pharmaceutical compositions provided herein can be provided in a unit-dosage form or multiple-dosage form. A unit-dosage form, as used herein, refers to a physically discrete unit suitable for administration to a human and animal subject using packaging known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged packet, sachet, tablet, capsule or eyedrop. For example, a 125 mg unit dose contains about 125 mg of an active ingredient in a packaged packet, sachet, tablet, capsule or eyedrop. A unit-dosage form may be administered in fractions or multiples thereof. A multiple-dosage form is a plurality of identical unit-dosage forms packaged in a single container to be administered as segregated unit-dosage forms. Examples of a multiple-dosage form include a packet or sachet of granules or powder, a vial or bottle of tablets or capsules, or a bottle of liquid solution in fluid ounces, pints or gallons for administration via an eye-dropper.

The pharmaceutical compositions provided herein can be administered as a single or divided dose over a period of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, a pharmaceutical composition provided herein is administered directly to the eye of a patient once, twice or thrice per day.

5.4.1. Topical Formulations and Postnatal Administration

In certain embodiments, the pharmaceutical compositions provided herein comprising Compound 1 are formulated for postnatal topical administration. In specific embodiments, the pharmaceutical compositions provided herein are formulated topical ophthalmic solutions (eye drops), which are normally available as a sterile, isotonic solution (i.e., at a pH of between about 3 and about 8, between about 4 to about 8, or about 4.5, between about 7 to about 8, or about 7.4), optionally further comprising a preservative.

In certain embodiments, the pharmaceutical compositions provided herein comprise a micronized form of Compound 1 having enhanced permeability and solubility and reduced irritation. In certain embodiments, the pharmaceutical compositions provided herein comprise a nanoparticle form of Compound 1 having enhanced permeability and solubility and reduced irritation.

In specific embodiments, the pharmaceutical compositions provided herein comprise a micronized form of Compound 1 wherein >90% of the particles of Compound 1 have a diameter (the $D_{90}$ value) of about 25 microns, about 20 microns, about 15 microns, about 10 microns, about 9 microns, about 8 microns, about 7 microns, about 6 microns, about 5 microns, about 4 microns, about 3 microns, about 2 microns or about 1 micron. In certain embodiments, the pharmaceutical compositions provided herein comprise a nanoparticle form of Compound 1 having enhanced solubility. In specific embodiments, the pharmaceutical compositions provided herein comprise a nanoparticle form of Compound 1 wherein >90% of the particles of Compound 1 have a diameter (the $D_{90}$ value) of about 0.3 microns, about 0.25 microns, about 0.2 microns, about 0.15 microns, about 0.1 microns, about 0.09 microns, about 0.08 microns, about 0.07 microns, about 0.06 microns, about 0.05 microns, about 0.04 microns, about 0.03 microns, about 0.02 microns or about 0.01 microns.

The term "eye drops" as used herein refers to a pharmaceutical liquid formulation which is administered in the form of drops on the external surface of the eye and which has a local effect on the interior and posterior segment of the eye, including the cornea, iris, choroid, retinal pigment epithelium, retina, macula, fovea, optic nerve and vitreous humor.

For ophthalmic applications, Compound 1 is formulated into solutions, suspensions or ointments appropriate for use in the eye. For ophthalmic formulations generally, see Mitra (ed.), Ophthalmic Drug Delivery Systems, Marcel Dekker, Inc., New York, N.Y. (1993) and also Havener, W. H., Ocular Pharmacology, C.V. Mosby Co., St. Louis (1983). Ophthalmic pharmaceutical compositions may be adapted for topical administration to the eye in the form of solutions, suspensions, ointments, creams or as a solid insert. For a single dose, from between 0.1 ng to 5000 µg, 1 ng to 500 µg, or 10 ng to 100 µg of Compound 1 can be applied to an eye surface.

A topical formulation may be in any form suitable for topical administration, including, without being limited thereto, an ophthalmic solution (e.g. eye drops), an ophthalmic suspension, an ophthalmic nanosuspension, an ophthalmic emulsion, an ophthalmic nanoemulsion, an ophthalmic gel or an ophthalmic ointment or oily lotion. Topical administration of Compound 1 or a pharmaceutically acceptable salt thereof also comprises the use of ophthalmic patches carrying an Compound 1 or a pharmaceutically acceptable salt thereof in a suitable drug containing layer and to be placed on top of the eye as well as to ocular inserts which are devices containing Compound 1 or a pharmaceutically acceptable salt thereof and placed into the inferior or superior conjunctival sacs.

Eye drops may be prepared by dissolving Compound 1 or a pharmaceutically acceptable salt thereof and a cationic modifier in a sterile aqueous solution such as saline, buffering solution and the like, or by combining powder compositions to be dissolved before use. Other additives may be included in the eye drops such as isotonizing agents (e.g., sodium chloride, boric acid, mannitol, sorbitol, trehalose, glycerin and the like), buffer agents (e.g., boric acid, sodium monohydrogen phosphate, sodium dihydrogen phosphate and the like), preservatives (e.g., benzalkonium chloride, benzethonium chloride, disodium ethylenediametetraacetic acid (EDTA), Polyquarternium-1 (PolyQuad), Polyhexamethylene Biguanide (PHMB), chlorobutanol and the like), saccharide thickeners (e.g., lactose, mannitol, maltose and the like), hyaluronic acid or salts thereof (e.g., sodium hyaluronate, potassium hyaluronate and the like), mucopolysaccharides (e.g., chondroitin sulfate and the like), wetting polymers (e.g., sodium polyacrylate, carboxyvinyl polymer, crosslinked polyacrylate and the like).

Embodiments of ophthalmic formulations described herein contain an isotonic ophthalmic solution having a tonicity equal to that of a 0.9% sodium chloride solution (290 mOsm). The tonicity of an ophthalmic solution can be adjusted using methods described in Remington: The Science and Practice of Pharmacy (D B Troy, et al, 2006), known to those versed in the art.

Eye ointments may be prepared by mixing Compound 1 or a pharmaceutically acceptable salt thereof into a base. Nonlimiting examples of a base for an eye ointment include petrolatum, selen 50, Plastibase, macrogol and the like.

Certain embodiments of ophthalmic formulations described herein may optionally contain viscosity enhancers such as carboxymethyl cellulose, carboxymethyl cellulose sodium, methylcellulose, hydroxypropyl cellulose, hydroxypropylmethyl cellulose, hydroxyethyl cellulose, polyethylene glycol 300, polyethylene glycol 400, polyvinyl alcohol, providone and the like.

Other embodiments of ophthalmic formulations described herein may optionally contain viscosity enhancers derived from natural products such as veegum, alginates, xanthan gum, gelatin, acacia, tragacanth and the like.

In one embodiment, the ophthalmic delivery systems described herein comprise an isotonic solution for multiple dose ophthalmic application using Compound 1 for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

In one embodiment, an ophthalmic delivery system comprising an isotonic solution for daily multiple or single dose use ophthalmic application with extended life is used for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

In one embodiment, an ophthalmic delivery system utilizing viscous solutions or thermosetting gel is used for unit or multiple dose ophthalmic application for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

In one embodiment, an ophthalmic delivery system utilizing a liposomal emulsion to protect Compound 1 from proteolysis is used for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

In one embodiment, an ophthalmic delivery system comprising Compound 1 entrapped in albumin microspheres is used for slow release of Compound 1 for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

In one embodiment, an ophthalmic delivery system comprising Compound 1 entrapped in injectable PLA/PGA microspheres is used for depot release of Compound 1 in the ophthalmic tissues for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

In one embodiment, an ophthalmic delivery system comprising Compound 1 in a slowly eroding, biodegradable film to deliver slow release of Compound 1 topically or via implant is used for postnatally treating, preventing, or managing an ocular disease ameliorated by modulation of premature translation termination or nonsense-mediated mRNA decay, comprising administering to a patient having an ocular disease ameliorated by modulation of premature translation termination or nonsense-mediated mRNA decay an effective amount of a pharmaceutical composition of 3-[5-(2-fluoro-phenyl)-[1,2,4]oxadiazol-3-yl]benzoic acid provided herein or an effective amount of a pharmaceutical composition of a salt of 3-[5-(2-fluoro-phenyl)-[1,2,4]oxadiazol-3-yl]benzoic acid provided herein.

The ophthalmic solution, suspension or ointment described herein for postnatally treating, preventing, or managing an ocular disease ameliorated by modulation of premature translation termination or nonsense-mediated mRNA decay may contain non-toxic auxiliary substances such as preservative components which are non-injurious in use, for example, benzalkonium chloride, disodium EDTA, polyquarternium-1, polyhexamethylene biguanide, methyl and propyl paraben, benzyldodecinium bromide, benzyl alcohol, or phenylethanol; buffering ingredients such as sodium chloride, sodium borate, sodium acetate, sodium citrate, boric acid, sodium monohydrogen phosphate, sodium dihydrogen phosphate or gluconate buffers; and other conventional ingredients such as sorbitan monolaurate, triethanolamine, polyoxyethylene sorbitan monopalmitylate, ethylenediamine tetraacetic acid, and the like.

The ophthalmic solution, suspension or ointment described herein for postnatally treating, preventing, or managing an ocular disease ameliorated by modulation of premature translation termination or nonsense-mediated mRNA decay may be administered as often as necessary to maintain an acceptable level of Compound 1 in the eye. Administration to the mammalian eye may be about once, twice or thrice daily.

In certain embodiments, Compound 1 may be combined with purified water and adjusted for solubility, physiological pH and isotonicity using a buffering agent. Examples of buffering agents to maintain or adjust pH include, but are not limited to, acetate buffers, citrate buffers, phosphate buffers and borate buffers. Examples of agents to maintain or adjust tonicity include, but are not limited to, sodium chloride, boric acid, mannitol, sorbitol, trehalose, glycerin and the like. In one or more embodiments, the concentration of the tonicity agent may be in a range of from about 0.01% to about 10.0% w/v, about 0.01% to about 5.0% w/v, about 0.01% to about 2.0% w/v or about 0.01% to about 1.0% w/v. In certain embodiments, the concentration of the tonicity agent may be in a range of from about 0.1% to about 5.0% w/v, about 0.1% to about 2.0% w/v or about 0.1% to about 1.0% w/v.

Certain formulations for ophthalmic use may be optionally aliquoted into either a plurality of discrete, sterile disposable cartridges each of which is suitable for unit dosing, or a single cartridge for unit dosing. Such a single disposable cartridge may be, for example, a conical or cylindrical specific volume dispenser, with a container having side-walls squeezable in a radial direction to a longitudinal axis in order to dispense the container contents therefrom at one end of the container. Such disposable containers are currently used to dispense eye drops at 0.3 to 0.4 mL per unit dosing, and are ideally adaptable for the delivery of eye drops.

Ophthalmic solutions may also be packaged in multidose form, for example, as a plastic bottle with an eye-dropper. In such formulations, preservatives are optionally added to prevent microbial contamination after opening of the container. Suitable preservatives include, but are not limited to: benzalkonium chloride, disodium EDTA, polyquarternium-1, polyhexamethylene biguanide, chlorobutanol, methylparaben, propylparaben, phenylethyl alcohol, sorbic acid, or other agents known to those skilled in the art, and all of which are contemplated for use in the present invention. In certain embodiments, the preservative is selected from benzalkonium chloride, disodium EDTA, polyquarternium-1 or polyhexamethylene biguanide. Preservative-containing formulations may comprise from about 0.001 to about 1.0%, about 0.05 to about 0.75%, about 0.05 to about 0.5%, about 0.05 to about 0.25% or about 0.01 to about 0.25% weight/volume of the preservative.

In certain embodiments, polymers may be added to an ophthalmic formulation in order to increase the viscosity of the vehicle, thereby prolonging contact of the solution with the cornea and enhancing bioavailability. In certain embodiments, such polymers are selected from cellulose derivatives (e.g., methylcellulose, hydroxyethylcellulose, hydroxypropylcellulose or carboxymethylcellulose), dextran 70, gelatin, polyols, glycerin, polyethylene glycol 300, polyethylene glycol 400, polysorbate 80, propylene glycol, polyvinyl alcohol and povidone, or a combination thereof In certain embodiments ophthalmic formulations as disclosed herein may further comprise stabilizer/solubilizer such as a cyclodextrin. In certain embodiments, the cyclodextrin is selected from α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin.

In certain embodiments, a compound as disclosed herein, such as Compound 1 may be administered in a sustained release ophthalmic solution formulation. In a specific embodiment, the sustained release ophthalmic solution formulation further comprises an "insert," wherein the insert has bioadhesion properties for stable fixation to the therapeutic target area of the body; or, has ion exchange or permeability properties for loading a therapeutic agent for release over a period of time; or, has biodegradation properties for non-invasive removal after the effective dose of the therapeutic agent is delivered.

Any method known to those in the art for contacting a cell, organ or tissue with a compound may be employed. Suitable methods include in vitro, ex vivo, or in vivo methods. In vivo methods typically include the administration of Compound 1 to a mammal, preferably a human. When used in vivo for therapy, Compound 1 is administered to the subject in effective amounts {i.e., amounts that have desired therapeutic effect). The dose and dosage regimen will depend upon the degree of the ophthalmic condition in the subject and the characteristics of Compound 1, e.g., therapeutic index for the subject and the subject's clinical history.

The effective amount of Compound 1 may be determined during pre-clinical trials and clinical trials by methods familiar to physicians and clinicians. An effective amount of Compound 1 useful in the methods of the present invention, preferably in a pharmaceutical composition, may be administered to a mammal in need thereof by any of a number of well-known methods for administering pharmaceutical compounds. In some embodiments, Compound 1 is administered systemically. In some embodiments, Compound 1 is administered locally. In some embodiments, Compound 1 is administered epicutaneously, orally, nasally, parenterally (intravenously, intramuscularly, intraperitoneally, or subcutaneously), topically, rectally, intracavernously, intradermally, transdermally, by inhalation, intraarterially, intracerebrally, interosseusly, intrathecally, intravesically, iontophoretically, ocularly, etc. Administration includes self-administration and administration by another.

For ophthalmic applications, Compound 1 is delivered in a therapeutically effective amount to select parts of the eye, including posterior chamber, ora serrata, ciliary muscle, ciliary zonules, canal of Schlemm, pupil, anterior chamber, cornea, iris, lens cortex, lens nucleus, ciliary process, conjunctiva, inferior oblique muscle, inferior rectus muscle, medial rectus muscle, retinal arteries and veins, optic disc, dura mater, central retinal artery, central retinal vein, optic nerve, vorticose vein, bulbar sheath, macula, fovea, sclera, choroid, superior rectus muscle, and retina.

In certain embodiments, the frequency of administration can vary greatly, depending on the needs of each subject and the severity of the disease to be treated, such administration may be from about once a week to about ten times a day, such as from about three times a week to about three times a day, or once or twice a day.

5.4.2. Oral Formulations and Prenatal Administration

In certain embodiments, the pharmaceutical compositions provided herein are formulated for prenatal delivery via oral administration to a natural mother or surrogate. In certain embodiments, the pharmaceutical compositions provided herein for oral administration are provided in solid, semi-solid, or liquid dosage forms for oral administration. As used herein, oral administration also includes buccal, lingual, and sublingual administration. Suitable oral dosage forms include, but are not limited to, tablets, sublingual or buccal films (i.e., fastmelts), chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient, the pharmaceutical compositions can contain one or more pharmaceutically acceptable carriers or excipients, including, but not limited to, binders, fillers, diluents, disintegrants, wetting agents, surfactants, lubricants, glidants, pH-modifiers, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose (CMC), carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methyl cellulose and carboxymethyl cellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate.

Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

In certain embodiments, the pharmaceutical composition is formulated as a solid oral dosage form. In certain embodiments, the pharmaceutical composition is formulated as a liquid oral dosage form. In certain embodiments, the unit dosage form is provided as a suspension in a pharmaceutically acceptable solvent, which includes, but is not limited to, water, milk, a carbonated beverage, juice, apple sauce, baby food, or baby formula.

In certain embodiments, provided herein are pharmaceutical compositions, which comprise a pharmaceutically acceptable salt of 3-[5-(2-fluoro-phenyl)-[1,2,4]oxadiazol-3-yl]benzoic acid and one or more additional pharmaceutically acceptable excipients. In one embodiment, the pharmaceutical composition is formulated as granules. In another embodiment, the one or more excipients are selected from the group consisting of polydextrose, mannitol, poloxamer, polyethylene glycol, hydroxyethyl cellulose, crospovidone, artificial vanilla flavor, and magnesium stearate.

Additionally provided herein are pharmaceutical composition comprising about 25% by weight of a pharmaceutically acceptable salt of 3-[5-(2-fluoro-phenyl)-[1,2,4]oxadiazol-3-yl]-benzoic acid; about 1% by weight of colloidal silicon dioxide; and one or more additional pharmaceutically acceptable excipients. In one embodiment, the pharmaceutical composition is formulated as granules. In another embodiment, the one or more excipients are selected from the group consisting of polydextose, mannitol, poloxamer, polyethylene glycol, hydroxyethyl cellulose, crospovidone, artificial vanilla flavor, and magnesium stearate.

Further provided herein are pharmaceutical compositions comprising about 25% by weight of a pharmaceutically acceptable salt of 3-[5-(2-fluoro-phenyl)-[1,2,4]oxadiazol-3-yl]-benzoic acid, about 25.65% by weight of polydextose, about 26.4% by weight of mannitol, about 3.7% by weight of poloxamer, about 10% by weight of polyethylene glycol, about 1.5% by weight of hydroxyethyl cellulose, about 5% by weight of crospovidone, about 0.75% by weight of artificial vanilla flavor, about 1% by weight of colloidal silicon dioxide, and about 1% by weight of magnesium stearate. In one embodiment, the pharmaceutical composition is formulated as granules.

Further provided herein are pharmaceutical compositions, comprising about 130 mg of a pharmaceutically acceptable salt of 3-[5-(2-fluoro-phenyl)-[1,2,4]oxadiazol-3-yl]-benzoic acid, about 133.38 mg of polydextose, about 137.28 mg of mannitol, about 19.24 mg of poloxamer, about 52 mg of polyethylene glycol, about 7.8 mg of hydroxyethyl cellulose, about 26 mg of crospovidone, about 3.9 mg of artificial vanilla flavor, about 5.2 mg of colloidal silicon dioxide, and about 5.2 mg of magnesium stearate. In one embodiment, the pharmaceutical composition is formulated as granules.

Further provided herein are pharmaceutical compositions, comprising about 205 mg of a pharmaceutically acceptable salt of 3-[5-(2-fluoro-phenyl)-[1,2,4]oxadiazol-3-yl]-benzoic acid, about 210.33 mg of polydextose, about 216.48 mg of mannitol, about 30.34 mg of poloxamer, about 82 mg of polyethylene glycol, about 12.3 mg of hydroxyethyl cellulose, about 41 mg of crospovidone, about 6.15 mg of artificial vanilla flavor, about 8.2 mg of colloidal silicon dioxide, and about 8.2 mg of magnesium stearate. In one embodiment, the pharmaceutical composition is formulated as granules.

Further provided herein are pharmaceutical compositions, comprising about 330 mg of a pharmaceutically acceptable salt of 3-[5-(2-fluoro-phenyl)-[1,2,4]oxadiazol-3-yl]-benzoic acid, about 338.58 mg of polydextose, about 348.48 mg of mannitol, about 48.84 mg of poloxamer, about 132 mg of polyethylene glycol, about 19.8 mg of hydroxyethyl cellulose, about 66 mg of crospovidone, about 9.9 mg of artificial vanilla flavor, about 13.2 mg of colloidal silicon dioxide, and about 13.2 mg of magnesium stearate. In one embodiment, the pharmaceutical composition is formulated as granules.

Further provided herein are pharmaceutical compositions, comprising about 405 mg of a pharmaceutically acceptable salt of 3-[5-(2-fluoro-phenyl)-[1,2,4]oxadiazol-3-yl]-benzoic acid, about 415.53 mg of polydextose, about 427.68 mg of mannitol, about 59.94 mg of poloxamer, about 162 mg of polyethylene glycol, about 24.3 mg of hydroxyethyl cellulose, about 81 mg of crospovidone, about 12.15 mg of artificial vanilla flavor, about 16.2 mg of colloidal silicon dioxide, and about 16.2 mg of magnesium stearate. In one embodiment, the pharmaceutical composition is formulated as granules.

Further provided herein are pharmaceutical compositions, comprising about 505 mg of a pharmaceutically acceptable salt of 3-[5-(2-fluoro-phenyl)-[1,2,4]oxadiazol-3-yl]-benzoic acid, about 518.13 mg of polydextose, about 4533.28 mg of mannitol, about 74.74 mg of poloxamer, about 202 mg of polyethylene glycol, about 30.3 mg of hydroxyethyl cellulose, about 101 mg of crospovidone, about 15.15 mg of artificial vanilla flavor, about 20.2 mg of colloidal silicon dioxide, and about 20.2 mg of magnesium stearate. In one embodiment, the pharmaceutical composition is formulated as granules.

In certain embodiments, the unit dosage form comprises from about 35 to about 1,400, from about 125 to about 1,000, from about 250 to about 1,000, or from about 500 to about 1,000 mg of Compound 1.

In certain embodiments, the unit dosage form comprises about 35, about 50, about 70, about 100, about 125, about 140, about 175, about 200, about 250, about 280, about 350, about 500, about 560, about 700, about 750, about 1,000, or about 1,400 mg of Compound 1.

In certain embodiments, the pharmaceutical composition provided herein is formulated as granules. In certain embodiments, the pharmaceutical composition provided herein is packaged in a packet. In certain embodiments, the pharmaceutical composition provided herein is packaged in a heat-sealed laminated aluminum packet. In certain embodiments, the pharmaceutical composition provided herein is packaged in a child-resistant packet. In certain embodiments, the pharmaceutical composition provided herein is packaged in a packet, which comprises layers of polyethylene terephthalate, polyethelyene, aluminum foil, adhesive, and sealing film. In certain embodiments, the pharmaceutical composition provided herein is packaged in a bottle, including, but not limited to, high density polyethylene (HDPE) bottles.

In certain embodiments, the pharmaceutical composition provided herein is formulated as granules for reconstitution. In certain embodiments, the pharmaceutical composition provided herein is formulated as granules for reconstitution as oral suspension.

In certain embodiments, the pharmaceutical composition provided herein is reconstituted before administration with a pharmaceutically acceptable solvent, which includes, but is not limited to, water, milk, a carbonated beverage, juice, fruit juice, fruit punch, apple sauce, baby food, or baby formula; or a semi-solid fluid, including, but not limited to semi-solid dairy, yogurt, pudding, apple sauce, soy, fruit, and grain based products.

In certain embodiments, the pharmaceutical composition provided herein is reconstituted before administration with water. In one embodiment, reconstitution of a 250 mg unit dosage formulation Compound 1 is carried out by the addition of about 10 mL of water directly in a bottle containing Compound 1 to achieve a concentration of about 25 mg/mL in the total volume of suspension.

In certain embodiments, the pharmaceutically acceptable salt is a magnesium salt, a potassium salt, a sodium salt, a tromethamine salt, an L-lysine salt, an L-arginine salt, an N-methyl glucamine salt or an L-histidine salt.

5.4.3. Parenteral Formulations and Administration

The pharmaceutical compositions provided herein comprising Compound 1 can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, benzyl alcohol, chlorobutanol, methyl and propyl p-hydroxybenzoates, benzalkonium chloride (e.g., benzethonium chloride), disodium EDTA, polyquarternium-1, polyhexamethylene biguanide, methyl- and propyl-parabens, and sorbic acid. Suitable isotonic agents include, but are not limited to, sodium chloride, boric acid, mannitol, sorbitol, trehalose, glycerin, and dextrose. Suitable buffering agents include, but are not limited to, borate, phosphate and citrate. Suitable antioxidants are those as described herein, including bisulfite and sodium metabisulfite. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, DEAE-C, DEAE-D or cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained-, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

5.4.4. Particle Size

Provided herein are forms of Compound 1 having a volume weighted mean diameter D(4,3) of from about 2 μm to about 12 μm. Also provided herein are forms of Compound 1 having a surface weighted mean diameter D(3,2) of from about 1 μm to about 3 μm. Further provided herein are forms of Compound 1 having a $D_{90}$ particle size in the range of from about 5 μm to about 26 μm, having a $D_{50}$ particle size in the range of from about 1 μm to about 6 μm, having a $D_{10}$ particle size in the range of from about 0.1 μm to about 1.5 μm.

5.4.5. Kits

The pharmaceutical compositions provided herein can be provided as an article of manufacture using packaging materials well known to those of skill in the art. Examples of pharmaceutical packaging materials include, but are not limited to, blister packs, bottles, tubes, inhalers, pumps, bags, vials, containers, syringes, eye droppers, and any packaging material suitable for a selected formulation and intended mode of administration and treatment.

Provided herein are kits which, when used by the medical practitioner, can simplify the administration of appropriate amounts of the active ingredient to a subject. In certain embodiments, the kit provided herein includes a container and a dosage form of a pharmaceutical formulation provided herein.

In certain embodiments, the kit includes a container comprising a dosage form of the pharmaceutical formulation provided herein, in a container comprising one or more other therapeutic agent(s) described herein.

Kits provided herein can further include devices that are used to administer the active ingredient. Examples of such devices include, but are not limited to, syringes, needle-less injectors drip bags, patches, eye droppers and inhalers.

Kits provided herein can further include pharmaceutically acceptable vehicles that can be used to administer the active ingredient. For example, if the active ingredient is provided in a solid form that must be reconstituted for parenteral administration, the kit can comprise a sealed container of a suitable vehicle in which the active ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

5.5. Methods of Use

Provided herein are methods for treating, preventing, or managing a disease ameliorated by modulation of premature translation termination or nonsense-mediated mRNA decay, comprising administering to a patient having a disease ameliorated by modulation of premature translation termination or nonsense-mediated mRNA decay an effective amount of a pharmaceutical composition provided herein or an effective amount of a salt of 3-[5-(2-fluoro-phenyl)-[1,2,4]oxadiazol-3-yl]benzoic acid provided herein.

Further provided herein are methods for treating, preventing, or managing a disease associated with a nonsense mutation, comprising administering to a patient having a disease associated with a nonsense mutation an effective amount of a pharmaceutical composition provided herein or an effective amount of a salt of 3-[5-(2-fluoro-phenyl)-[1,2,4]oxadiazol-3-yl]benzoic acid provided herein.

Further provided herein are methods for treating, preventing, or managing a disease associated with a premature stop codon, comprising administering to a patient having a disease associated with a premature stop codon an effective amount of a pharmaceutical composition provided herein or an effective amount of a salt of 3-[5-(2-fluoro-phenyl)-[1,2,4]oxadiazol-3-yl]benzoic acid provided herein.

In certain embodiments, provided herein are methods for the treatment, prevention or management of any disease that is associated with a gene exhibiting premature translation termination and/or nonsense-mediated mRNA decay. In one embodiment, the disease is due, in part, to the lack of expression of the gene resulting from a premature stop codon. Examples of genes which may exhibit premature translation termination and/or nonsense-mediated mRNA decay and diseases associated with premature translation termination and/or nonsense-mediated mRNA decay are found in U.S. Patent Application No. 60/390,747, the disclosure of which is incorporated herein by reference in its entirety.

In certain embodiments, provided herein are methods for the prenatal treatment, prevention or management of a disease associated with a nonsense mutation in a gene in an embryo or fetus who has or is predisposed or susceptible to a disease associated with a nonsense mutation in a gene, such as those described herein. In one embodiment, a pregnant female is administered a pharmaceutical composition provided herein, via whom the active ingredient passes through the placenta of the pregnant female to the embryo or fetus. In certain embodiments, a pharmaceutical compositions provided herein is administered orally or parenterally to the pregnant female.

Ocular diseases or disorders associated with premature translation termination and/or nonsense-mediated mRNA decay or ameliorated by the suppression thereof include, but are not limited to: aniridia, choroideremia, renal-coloboma syndrome, Lebers congenital amaurosis, retinitis pigmentosa, Bardet-Biedl syndrome, or Usher syndrome.

Further provided herein are methods for producing in a subject (such as a human) in need thereof an effective amount of a functional read-through protein(s) encoded by a nucleic acid sequence comprising a nonsense mutation, the methods comprising administering to the subject an effective amount of a pharmaceutical composition provided herein or an effective amount of a salt of 3-[5-(2-fluoro-phenyl)-[1,2,4]oxadiazol-3-yl]benzoic acid provided herein. In a specific embodiment, the nucleic acid sequence is a gene associated with an ocular condition. In certain embodiments, the ocular condition is aniridia, choroideremia, renal-coloboma syndrome, Lebers congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus or tunica vasculosa lentis. In another specific embodiment, the ocular condition is Usher syndrome type 2A. In some embodiments, the nucleic acid sequence is the PAX6 gene, REP1 gene, CHD7 gene, PAX2 gene, or BBS2 gene. The production of a functional read-through protein(s) may be assessed by an in vitro assay and/or in an animal model. For example, compounds that suppress premature translation termination and/or nonsense-mediated mRNA decay can be identified using techniques known to those of skill in the art. See, e.g., U.S. Publication No. 2005/0233327, published Oct. 20, 2005, entitled "Methods for Identifying Small Molecules that Modulate Premature Translation Termination and Nonsense Mediated mRNA Decay"; U.S. Pat. No. 6,458,538 entitled "Methods of Assaying for Compounds that Inhibit Premature Translation Termination and Nonsense Mediated RNA Decay"; U.S. Publication No. 2003/0008317, published Jan. 9, 2003, entitled "Methods of Assaying for Compounds that Inhibit Premature Translation Termination and Nonsense Mediated RNA Decay"; and International Application Publication No. WO 2004/010106 entitled "Methods of Assaying for Compounds that Inhibit Premature Translation Termination and Nonsense Mediated RNA Decay," each of which is incorporated herein by reference in its entirety. In particular, cell-based and cell-free assays can be used for the identification of a compound that suppresses premature translation termination and/or nonsense-mediated mRNA decay.

In certain embodiments, diseases to be treated, prevented or managed by the methods provided herein include ocular conditions associated with a nonsense mutation in a gene(s), the methods comprising administering to a subject in need thereof an effective amount of a pharmaceutical composition provided herein or an effective amount of a salt of 3-[5-(2-fluoro-phenyl)-[1,2,4]oxadiazol-3-yl]benzoic acid provided herein. In a specific embodiment, the ocular condition associated with a nonsense mutation in a gene(s) is aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus or tunica vasculosa lentis. In another specific embodiment, the ocular condition associated with a nonsense mutation in a gene(s) is Usher syndrome type 2A.

In a specific embodiment, the ocular condition prevented and/or treated in accordance with the methods is an ocular condition associated with a nonsense mutation(s). Examples of ocular conditions that may be prevented and/or treated in accordance with the methods include aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis. In a specific embodiment, the Usher syndrome is Usher syndrome type 2A.

In certain embodiments, the disease to be treated, prevented or managed by the methods provided herein is aniridia. In certain embodiments, a pharmaceutical composition or active agent described herein is used in combination with another therapy to treat aniridia. In a specific embodiment, the therapy used in addition to a pharmaceutical composition or active agent described herein is a miotic, a beta-blocker, a sympathomimetic, a carbonic anhydrase inhibitor, or a prostaglandin analogue. In specific embodiment, treating aniridia with a pharmaceutical composition or active agent described herein results in one, two or more of the following effects: (i) reduces or ameliorates the severity of aniridia; (ii) delays onset of aniridia; (iii) inhibits the progression of aniridia; (iv) reduces hospitalization of a subject; (v) reduces hospitalization length for a subject; (vi) improves the quality of life of a subject; (vii) reduces the number of symptoms associated with aniridia; (viii) reduces or ameliorates the severity of a symptom(s) associated with aniridia; (ix) reduces the duration of a symptom associated with aniridia; (x) prevents the recurrence of a symptom associated with aniridia; (xi) inhibits the development or onset of a symptom of aniridia; and/or (xii) inhibits of the progression of a symptom associated with aniridia. Symptoms of aniridia include albinism, ectopia lentis, spontaneous lens dislocation, arcus juvenilis, keratoconus; cataracts, glaucoma, nystagmus, strabismus, optic nerve hypoplasia, blindness, opaque corenea, vision impairment, and absence or partial absence of an iris. An animal model useful for determining the effectiveness of an agent for treatment of aniridia associated with a nonsense mutation is that described in Hill, R., et al., 1991, "Mouse Small eye results from mutations in a paired-like homeobox-containing gene," *Nature* 354(6354):522-525 and Gregory-Evans, C., et al., Postnata manipulation of Pax6 dosage reverses congenital tissue malformation defects," *J. Clin. Invest.* Doi:10.1172/JCI70462, both of which are incorporated by reference herein in their entirety.

In one embodiment, the aniridia is familial aniridia. In another embodiment, the aniridia is sporadic aniridia.

In one embodiment, the aniridia is a symptom associated with WAGR (Wilms tumor-aniridia-genital anomalies-retardation) syndrome or Gillespie syndrome.

In certain embodiments, the disease to be treated, prevented or managed by the methods provided herein is choroideremia. In certain embodiments, a pharmaceutical composition or active agent described herein is used in combination with another therapy to treat choroideremia. In specific embodiment, treating choroideremia with a pharmaceutical composition or active agent described herein results in one, two or more of the following effects: (i) reduces or ameliorates the severity of choroideremia; (ii) delays onset of choroideremia; (iii) inhibits the progression of choroideremia; (iv) reduces hospitalization of a subject; (v) reduces hospitalization length for a subject; (vi) improves the quality of life of a subject; (vii) reduces the number of symptoms associated with choroideremia; (viii) reduces or ameliorates the severity of a symptom(s) associated with choroideremia; (ix) reduces the duration of a symptom associated with choroideremia; (x) prevents the recurrence of a symptom associated with choroideremia; (xi) inhibits the development or onset of a symptom of choroideremia; and/or (xii) inhibits of the progression of a symptom associated with choroideremia. Symptoms of choroideremia include night blindness, loss of peripheral vision, and loss of central vision.

In certain embodiments, the disease to be treated, prevented or managed by the methods provided herein is renal-coloboma syndrome. In certain embodiments, a pharmaceutical composition or active agent described herein is used in combination with another therapy to treat renal-coloboma syndrome. In specific embodiment, treating renal-coloboma syndrome with a pharmaceutical composition or active agent described herein results in one, two or more of the following effects: (i) reduces or ameliorates the severity of renal-coloboma syndrome; (ii) delays onset of renal-coloboma syndrome; (iii) inhibits the progression of renal-coloboma syndrome; (iv) reduces hospitalization of a subject; (v) reduces hospitalization length for a subject; (vi) improves the quality of life of a subject; (vii) reduces the number of symptoms associated with renal-coloboma syndrome; (viii) reduces or ameliorates the severity of a symptom(s) associated with renal-coloboma syndrome; (ix) reduces the duration of a symptom associated with choroideremia; (x) prevents the recurrence of a symptom associated with renal-coloboma syndrome; (xi) inhibits the development or onset of a symptom of choroideremia; and/or (xii) inhibits of the progression of a symptom associated with renal-coloboma syndrome. Symptoms associated with renal-coloboma syndrome include dysplasia of the optic nerve, scleral staphyloma, retinal thinning, myopia, and optic nerve cysts.

In certain embodiments, the disease to be treated, prevented or managed by the methods provided herein is retinitis pigmentosa. In certain embodiments, a pharmaceutical composition or active agent described herein is used in combination with another therapy to treat retinitis pigmentosa. In specific embodiment, treating retinitis pigmentosa with a pharmaceutical composition or active agent described herein results in one, two or more of the following effects:

(i) reduces or ameliorates the severity of retinitis pigmentosa; (ii) delays onset of retinitis pigmentosa; (iii) inhibits the progression of retinitis pigmentosa; (iv) improves the quality of life of a subject; (v) reduces the number of symptoms associated with retinitis pigmentosa; (vi) reduces or ameliorates the severity of a symptom(s) associated with retinitis pigmentosa; (vii) reduces the duration of a symptom associated with retinitis pigmentosa; (viii) prevents the recurrence of a symptom associated with retinitis pigmentosa; (ix) inhibits the development or onset of a symptom of retinitis pigmentosa; and/or (x) inhibits of the progression of a symptom associated with retinitis pigmentosa. Symptoms associated with retinitis pigmentosa include rod degeneration, loss of night vision, tunnel vision, and blindness.

In certain embodiments, the disease to be treated, prevented or managed by the methods provided herein is Bardet-Biedl syndrome. In certain embodiments, a pharmaceutical composition or active agent described herein is used in combination with another therapy to treat Bardet-Biedl syndrome. In specific embodiment, treating Bardet-Biedl syndrome with a pharmaceutical composition or active agent described herein results in one, two or more of the following effects: (i) reduces or ameliorates the severity of Bardet-Biedl syndrome; (ii) delays onset of Bardet-Biedl syndrome; (iii) inhibits the progression of Bardet-Biedl syndrome; (iv) improves the quality of life of a subject; (v) reduces the number of symptoms associated with Bardet-Biedl syndrome; (vi) reduces or ameliorates the severity of a symptom(s) associated with retinitis pigmentosa; (vii) reduces the duration of a symptom associated with Bardet-Biedl syndrome; (viii) prevents the recurrence of a symptom associated with Bardet-Biedl syndrome; (ix) inhibits the development or onset of a symptom of Bardet-Biedl syndrome; and/or (x) inhibits of the progression of a symptom associated with Bardet-Biedl syndrome. Symptoms associated with Bardet-Biedl syndrome include rod-cone dystrophy, visual loss, and night blindness.

In certain embodiments, the disease to be treated, prevented or managed by the methods provided herein is Usher syndrome. In certain embodiments, a pharmaceutical composition or active agent described herein is used in combination with another therapy to treat Usher syndrome. In specific embodiment, treating Usher syndrome with a pharmaceutical composition or active agent described herein results in one, two or more of the following effects: (i) reduces or ameliorates the severity of Usher syndrome; (ii) delays onset of Usher syndrome; (iii) inhibits the progression of Usher syndrome; (iv) improves the quality of life of a subject; (v) reduces the number of symptoms associated with Usher syndrome; (vi) reduces or ameliorates the severity of a symptom(s) associated with Usher; (vii) reduces the duration of a symptom associated with Usher syndrome; (viii) prevents the recurrence of a symptom associated with Usher syndrome; (ix) inhibits the development or onset of a symptom of Usher syndrome; and/or (x) inhibits of the progression of a symptom associated with Usher syndrome. Symptoms associated with Usher syndrome include decreased night vision. In a specific embodiment, the Usher syndrome is Usher syndrome type 2A.

In certain embodiments, the methods provided herein comprise the prenatal systemic administration of a pharmaceutical composition provided herein or a salt of 3-[5-(2-fluoro-phenyl)-[1,2,4]oxadiazol-3-yl]benzoic acid provided herein in three doses in a 24 hour period according to the formula: 1X, 1X, 2X, where X is a particular initial dose (e.g., 4 mg/kg, 7 mg/kg, 10 mg/kg or 20 mg/kg) of the active agent. In a specific embodiment, a pharmaceutical composition provided herein or a salt of 3-[5-(2-fluoro-phenyl)-[1,2,4]oxadiazol-3-yl]benzoic acid provided herein is continuously administered three times per 24 hour period at doses of about 2 mg/kg to about 6 mg/kg (e.g., 4 mg/kg), about about 2 mg/kg to about 6 mg/kg (e.g., 4 mg/kg) and about 6 mg/kg to about 10 mg/kg (e.g., 8 mg/kg) of the active agent for days, weeks, months or years. In another specific embodiment, a pharmaceutical composition provided herein or a salt of 3-[5-(2-fluoro-phenyl)-[1,2,4]oxadiazol-3-yl]benzoic acid provided herein is continuously administered three times per 24 hour period at doses of about 5 mg/kg to about 9 mg/kg (e.g., 7 mg/kg), about 5 mg/kg to about 9 mg/kg (e.g., 7 mg/kg) and 12 mg/kg to about 16 mg/kg (e.g., 14 mg/kg) of the active agent for weeks, months or years. In a specific embodiment, a pharmaceutical composition provided herein or a salt of 3-[5-(2-fluoro-phenyl)-[1,2,4]oxadiazol-3-yl]benzoic acid provided herein is continuously administered three times per 24 hour period at doses of about 8 mg/kg to about 12 mg/kg (e.g., 10 mg/kg), about 8 mg/kg to about 12 mg/kg (e.g., 10 mg/kg) and about 18 mg/kg to about 22 mg/kg (e.g., 20 mg/kg) of the active agent for days, weeks, months or years. In a specific embodiment, a pharmaceutical composition provided herein or a salt of 3-[5-(2-fluoro-phenyl)-[1,2,4]oxadiazol-3-yl]benzoic acid provided herein is continuously administered three times per 24 hour period at doses of about 18 mg/kg to about 22 mg/kg (e.g., 20 mg/kg), about 18 mg/kg to about 22 mg/kg (e.g., 20 mg/kg) and about 38 mg/kg to about 42 mg/kg (e.g., 40 mg/kg) of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). Continuous prenatal therapy is preferably used for the treatment, prevention or management of an ocular disease.

In certain embodiment, the methods provided herein comprise maintaining a plasma concentration of Compound 1 of greater than: about 0.1 µg/mL, about 0.5 µg/mL, about 2 µg/mL, about 5 µg/mL, about 10 µg/mL, about 20 µg/mL, about 25 µg/mL, about 40 µg/mL, about 50 µg/mL, about 100 µg/mL, about 150 µg/mL, about 200 µg/mL, about 250 µg/mL or about 500 µg/mL in a patient for at least about 2, 2.5, 3, 3.5, 4, 4.5, 5, 6, 8, 12 or 24 hours or longer. Levels of Compound 1 in plasma can be measured, for example, by high performance liquid chromatography (HPLC).

In another embodiment, the methods provided herein comprise maintaining a plasma concentration of Compound 1 of about 0.1 µg/mL to about 500 µg/mL, about 2 µg/mL to about 40 µg/mL, about 2 µg/mL to about 20 µg/mL, about 2 µg/mL to about 10 µg/mL or about 10 µg/mL to about 20 µg/mL in a patient for at least about 2, 2.5, 3, 3.5, 4, 4.5, 5, 6, 8, 12 or 24 hours or longer.

It will be understood that the amounts of a pharmaceutical composition or active agent administered to a patient in need thereof are or can be calculated based upon the actual weight of the patient in question or the average weight of the patient population in question (e.g., white males, white females, African American males, African American females, Asian males or Asian females, including adults and children).

6. EXAMPLES

The following examples are offered by way of illustration and not limitation. The following abbreviations are used in descriptions and examples:

| Abbreviation | Meaning |
| --- | --- |
| 2-PrOH | 2-propanol |
| ACN | acetonitrile |
| DCM | dichloromethane |
| DVS | Dynamic Vapor Sorption |
| EMA | elemental analysis |
| EtOAc | ethyl acetate |
| EtOH | ethanol |
| FaSSIF | Fasted-State Simulated Intestinal Fluid |
| FeSSIF | Fed-State Simulated Intestinal Fluid |
| FT-Raman | Fourier-Transform Raman spectroscopy |
| HCl | hydrochloride |
| HPLC | High Performance Liquid Chromatography |
| NaOH | sodium hydroxide |
| SIF | Simulated Intestinal Fluid |
| TBME | tert-butyl methyl ether |
| NMR | Nuclear Magnetic Resonance |
| RH/r.h. | Relative Humidity |
| THF | tetrahydrofuran |
| PXRD | Powder X-Ray Diffraction |

6.1. Salt/Co-Crystal Formers

Based on the solubility, pKa and chemical structure of Compound 1, the salt/co-crystal formers listed below Table 1 were jointly selected for salt preparation.

TABLE 1

Salt/Co-Crystal Formers

| Salt/Co-crystal Formers | Abbr | Source | Formula | Mw (g/mol) |
| --- | --- | --- | --- | --- |
| L-arginine | ARG | Fluka | $C_6H_{14}N_4O_2$ | 174.2 |
| histidine | HIS | Fluka | $C_6H_9N_3O_2$ | 155.16 |
| L-lysine | LYS | Fluka | $C_6H_{14}N_2O_2$ | 146.19 |
| magnesium methoxide | Mg | Fluka | $C_2H_6MgO_2$ | 86.38 |
| potassium hydroxide | K | Fluka | KOH | 56.11 |
| tromethamine | TRO | ABCR | NaOH | 40 |

6.2. Overview on Characterization of Selected Salts/Co-Crystals

Table 2: Characterization of Selected Salts/Co-Crystals (the term Salt # refers to the formation of a first or second salt of the type indicated)

TABLE 2

| Salt # | Aqueous solubility[1] | Hygroscopicity[2] | Crystallinity[3] | Hydrate formation | Remarks |
| --- | --- | --- | --- | --- | --- |
| Potassium 1 | 57 | +7.81 (hygroscopic) | + | likely (EMA, DVS) | mono-salt |
| Sodium 1 | 22 | +19.52 (very hygroscopic) | ++ | likely (EMA, DVS[4]) | mono-salt |
| Tromethane 1 | 18 | +3.59 (hygroscopic) | +++ | inconclusive | inconclusive |
| L-lysine 1 | 15 | +1.15 (slightly hygroscopic) | +++ | not found | mono-salt |
| Magnesium 2 | 0.44 | +13.10 (hygroscopic) | ++ | likely (EMA, DVS) | hemi-salt |

[1] values given in mg/mL
[2] mass change in wt % in the range 0→85% r.h.
[3] crystallinity estimated from PXRD: +++ = high, ++ = good, + low
[4] strong indication for several hydrates

6.3. Evaporation Experiments

Stock solutions of the free acid and of each salt/co-crystal former were prepared in the selected solvents (see Table 3, where concentration is shown in mol/L and the term "N/A" indicates that a particular stock solution was not prepared). In addition to those listed in Table 3, stock solutions of L-arginine, L-histidine, L-lysine, potassium hydroxide and sodium hydroxide solvated in water were each also prepared to a concentration of 0.050 mol/L.

Crystallization was performed by evaporation of the solvents under $N_2$ flow (~0.4 L/min) at room temperature. The resulting solids were examined by visual inspection and Raman microscopy.

TABLE 3

| Form | Acetone | EtOH | THF | MeOH | MeOH/$CH_2Cl_2$ |
| --- | --- | --- | --- | --- | --- |
| Cpd 1 free acid | 0.050 | 0.004 | 0.050 | N/A | 0.011 |
| magnesium methoxide | 0.050 | 0.050 | 0.050 | 0.050 | N/A |
| tromethamine | 0.050 | 0.050 | 0.050 | 0.050 | N/A |

6.4. Slurry Experiment

A second set of solvents was selected for phase equilibration (slurry) experiments. 0.05 mL solvent was added to the residues of the evaporation experiments. The MTP's were shaken at r.t. on an Eppendorf Thermo-Mixer for three days. The solvents were removed under $N_2$ flow (~0.4 L/min; 2 days) at room temperature. The resulting solids were examined by visual inspection and Raman microscopy.

6.5. Crystallization Experiments

Unless otherwise specified, all experiments shown in Table 4 were carried out under ambient laboratory conditions. Fluka, Aldrich or ABCR analytical grade solvents were used. All solvents (except water) were dried over molecular sieve with pore size 3 or 4 Å prior to use.

Test Methods:

| Method | Analytical Tests Conducted |
|---|---|
| 1 | Raman; FT-Raman; PXRD; $^1$H-NMR (DMSO-$d_6$) |
| 2 | FT-Raman; PXRD; $^1$H-NMR (DMSO-$d_6$) |
| 3 | FT-Raman; PXRD; $^1$H-NMR (DMSO-$d_6$); DVS; Aqueous solubility |
| 4 | FT-Raman; PXRD; $^1$H-NMR ($D_2O/CD_3CN$) |
| 5 | FT-Raman; PXRD; $^1$H-NMR ($D_2O$); DVS; Aqueous solubility |
| 6 | FT-Raman; PXRD |
| 7 | FT-Raman |

Table 4: Crystallization Experiment Details

TABLE 4

| Form | Method | Description and Test Results |
|---|---|---|
| Compound 1 (Form A) | 1 | Compound 1 (2 g) Results: Raman: corresponds to free acid; FT-Raman: corresponds to free acid; PXRD: corresponds to Compound 1 (Form A); $^1$H-NMR: corresponds to free acid |
| Compound 1 (Form A) Magnesium Salt 1 | 6 | Compound 1 (154.6 mg) was dissolved in 1:3 (v/v) MeOH/DCM (16 mL); magnesium-methoxide (MgMo) (754 µL, 0.7 mol/L) was added; then, solvent was evaporated under nitrogen flow (80 mL/min) Results: FT-Raman: corresponds to Magnesium Salt 1; PXRD: corresponds to amorphous form |
| Compound 1 (Form A) Potassium Salt 1 | 3 | Compound 1 (152.1 mg) was dissolved in THF (5 mL); aqueous potassium hydroxide (1.06 mL, 0.5 mol/L) was added; then, solvent was evaporated under nitrogen flow (80 mL/min) Results: FT-Raman: corresponds to Potassium Salt 1; PXRD: partly crystalline form; $^1$H-NMR: corresponds to Form A, acidic H not detected; DVS: hygroscopic sample, hydrate formation; Aqueous solubility: 57.00 mg/mL, pH 9.2 |
| Compound 1 (Form A) Potassium Salt 2 | 6 | Potassium Salt 1 (28.5 mg) was suspended in water (0.2 mL) and sonicated for 5 min; then shaken at 25° C. and centrifuged at 500 rpm for 20 hours; to the obtained thick suspension was added water (0.05 mL); the mixture was shaken at 25° C. and centrifuged at 500 rpm for 4 hours; then filtered through a 0.1 µm PVDF centrifugal filter device (25° C., 15000 rpm, 5 min) Results: FT-Raman: corresponds to Potassium Salt 1; PXRD: corresponds to pattern of Potassium Salt 1 |
| Compound 1 (Form A) Sodium Salt 1 | 3 | Compound 1 (153.1 mg) was dissolved in EtOH (40 mL); a solution of aqueous sodium hydroxide (5.3 mL, 0.1 mol/L) was added; then solvent was evaporated under nitrogen flow (80 mL/min) Results: FT-Raman: corresponds to Sodium Salt 1; aqueous solubility determination shows spectrum corresponding to post-DVS Sodium Salt 1, corresponds to new form or mixture of both; PXRD: crystalline sample; $^1$H-NMR: corresponds to Form A, acidic H not detected; DVS: hygroscopic sample, hydrate formation; Aqueous solubility: 22.22 mg/mL, pH 8.3 |
| Compound 1 (Form A) Sodium Salt 2 | 6 | Sodium Salt 1 (20.2 mg) was suspended in water (0.2 mL); the mixture was sonicated for 5 min; then shaken at 25° C. and centrifuged at 500 rpm for 1 day; the product was filtered through a 0.1 µm PVDF centrifugal filter device (25° C., 15000 rpm, 5 min) Results: FT-Raman: shows either a new form or mixture of forms; PXRD: crystalline sample |
| Compound 1 (Form A) Tromethamine Salt 1 | 3 | Compound 1 (154.5 mg) was dissolved in acetone (40 mL); tromethamine (67.5 mg) was added and the mixture was dissolved in MeOH (4 mL); then, solvent was evaporated under nitrogen flow (80 mL/min) Results: FT-Raman: corresponds to Tromethamine Salt 4; aqueous solubility spectrum shows impurity; post-DVS spectrum shows additional impurity; PXRD: crystalline sample; $^1$H-NMR: corresponds to Form A and TRO with impurities; DVS: hygroscopic sample; Aqueous solubility |
| Compound 1 (Form A) Tromethamine Salt 2 | 6 | Tromethamine Salt 1 (20.3 mg) was suspended in water (0.2 mL); the mixture was sonicated for 5 min; then shaken at 25° C., and centrifuged at 500 rpm for 1 day; the product was filtered through a 0.1 µm PVDF centrifugal filter device (25° C., 15000 rpm, 5 min) Results: FT-Raman: corresponds to Tromethamine Salt 1 with less impurity; PXRD: corresponds to Tromethamine Salt 1 with different orientation |
| Compound 1 (Form A) L-lysine Salt 1 | 5 | Compound 1 (143.4 mg) was dissolved in THF (5 mL); L-lysine (LYS) (71.3 mg) dissolved in water (1 mL) was added; the solvent was evaporated under nitrogen flow (80 mL/min) |
| Compound 1 (Form A) L-lysine Salt 2 | 6 | L-lysine Salt 1 (8.8 mg) was suspended in water (0.1 mL); the mixture was sonicated for 5 min; then shaken at 25° C., and centrifuged at 500 rpm for 1 day; the product was filtered through a 0.1 µm PVDF centrifugal filter device (25° C., 15000 rpm, 5 min) |
| Compound 1 (Form A) Magnesium | 3 | Compound 1 (150.7 mg) was dissolved in THF (5 mL); a solution of aqueousmagnesium hydroxide (32.1 mg, 0.7 mol/L) was added; solvent was partially evaporated under nitrogen flow(80 mL/min); |

TABLE 4-continued

| Form | Method | Description and Test Results |
|---|---|---|
| Salt 2 | | the resulting precipitate was dried under vacuum<br>Results: FT-Raman: spectra corresponds to Magnesium Salt 1; PXRD: crystalline form; $^1$H-NMR: corresponds to Compound 1 Form A, having a hygroscopic, hydrate form |
| Compound 1 (Form A) Magnesium Salt 3 | 6 | Magnesium Salt 2 (33.1 mg) was suspended in water (0.1 mL); the mixture was sonicated for 5 min; then shaken at 25° C., and centrifuged at 500 rpm for 20 hours; the resulting product was obtained as a thick suspension; water (0.05 mL) was added; and, the mixture was shaken at 25° C., centrifuged at 500 rpm for 4 hours; then filtered through a 0.1 μm PVDF centrifugal filter device (25° C., 15000 rpm, 5 min)<br>Results: FT-Raman: spectra corresponds to Magnesium Salt 2; PXRD: corresponds to Magnesium Salt 2 |
| Compound 1 (Form A) Tromethamine Salt 3 | 7 | Compound 1 (150.6 mg) was dissolved in acetone (30 mL); tromethamine (62.7 mg) dissolved in water (2 mL) was added; the solvent was evaporated under nitrogen flow (80 mL/min)<br>Results: FT-Raman: corresponds to a nonstoichiometric mixture of tromethamine, Compound 1 and the tromethamine salt of Compound 1 |
| Compound 1 (Form A) Magnesium Salt 4 | 6 | Compound 1 (148.1 mg) was dissolved in THF (5 mL); an aqueous solution of magnesium hydroxide (31.1 mg) dissolved in water (3 mL) was added, forming a white precipitate upon mixing; the solvent was evaporated under nitrogen flow (80 mL/min)<br>Results: PXRD: crystalline form; similar to Magnesium Salt 2 with additional reflections; FT-Raman: spectra similar to Magnesium Salt 2 with additional bands |
| Compound 1 (Form A) Tromethamine Salt 4 | 6 | Compound 1 (151.6 mg) was dissolved in THF (5 mL); tromethamine (63.0 mg) dissolved in MeOH (5 mL) was added; the solvent was evaporated under nitrogen flow (80 mL/min)<br>Results: PXRD: similar to the nonstoichiometric mixture of tromethamine, Compound 1 and the tromethamine salt of Compound 1 with some reflections missing; FT-Raman: corresponds to a nonstoichiometric mixture of tromethamine, Compound 1 and the tromethamine salt of Compound 1 |
| Compound 1 (Form A) Tromethamine Salt 5 | 6 | Compound 1 (155.2 mg) was dissolved in acetone (40 mL); tromethamine (63.1 mg) dissolved in MeOH (5 mL) was added; the solvent was evaporated under nitrogen flow (80 mL/min)<br>Results: PXRD: corresponds to a nonstoichiometric mixture of tromethamine, Compound 1 and the tromethamine salt of Compound 1; FT-Raman: corresponds to a nonstoichiometric mixture of tromethamine, Compound 1 and the tromethamine salt of Compound 1 |
| Compound 1 (Form A) L-arginine Salt | 4 | Compound 1 (149.1 mg) was suspended in EtOH (20 mL); the mixture was sonicated for 5 min; then L-arginine (ARG) (93.5 mg) dissolved in water (2 mL) was added to provide a clear solution; the solvent was evaporated to half volume under nitrogen flow (80 mL/min); the resulting solid residue was separated from the remaining solvent<br>Results: FT-Raman: corresponds to L-arginine Salt 1; PXRD: crystalline form; $^1$H-NMR: corresponds to Compound 1 and L-arginine Salt |
| Compound 1 (Form A) L-histidine Salt 1 | 6 | Compound 1 (150.0 mg) wassuspended in EtOH (20 mL); the mixture was sonicated for 5 min; then L-histidine (HIS) (82.0 mg) dissolved in water (4 mL) was added to provide a suspension; the solvent volume was reduced under nitrogen flow (80 mL/min); the resulting product was filtered through a 0.45 μm PVDF centrifugal filter device<br>Results: FT-Raman: the sample was suspended in 2-PrOH (1 mL), the mixture was sonicated for 5 min; then stirred for 5 days; heated to 70° C. for 1 hour and slowly cooled to room temperature, resulting spectrum corresponds to L-histidine Salt 1; PXRD: crystalline form having spectra corresponding to a mixture of Compound 1 and L-histidine |
| Compound 1 (Form A) L-histidine Salt 2 | 7 | Compound 1 (156.3 mg) was dissolved in THF (5 mL); L-histidine (HIS) (86.7 mg) was dissolved in water (4 mL) was added to provide a turbid solution; the mixture was sonicated for 5 min; stirred for 5 days; then filtered through a 0.2 μm PTFE centrifugal filter device<br>Results: FT-Raman: spectra corresponds to L-histidine with traces of Compound 1 |
| Compound 1 (Form A) L-histidine Salt 3 | 7 | Compound 1 (155.4 mg) was suspended in MeOH (1 mL); L-histidine (86.7 mg) suspended in water (2 mL) was added to provide a turbid solution; the solution was sonicated for 5 min; stirred for 5 days; then filtered through a 0.2 μm PTFE centrifugal filter device; the suspension was heated to 70° C. for 1 hour, then slowly cooled to room temperature;<br>Results: FT-Raman: spectra corresponds to Compound 1 and L-histidine |

TABLE 4-continued

| Form | Method | Description and Test Results |
|---|---|---|
| Compound 1 (Form A) L-histidine Salt 4 | 7 | Compound 1 (151.6 mg) was suspended in EtOH (4 mL); L-histidine (81.3 mg) suspended in water (2 mL) was added to provide a turbid solution; the solution was sonicated for 5 min; stirred for 5 days; then filtered through a 0.2 µm PTFE centrifugal filter device; the suspension was heated to 70° C. for 1 hour, then slowly cooled to room temperature; Results: FT-Raman: spectra corresponds to Compound 1 and L-histidine |
| Compound 1 (Form A) L-histidine Salt 5 | 7 | Compound 1 (151.8 mg) was suspended in MeCN (3 mL); L-histidine (84.5 mg) suspended in water (2 mL) was added to provide a turbid solution; the solution was sonicated for 5 min; stirred for 5 days; then filtered through a 0.2 µm PTFE centrifugal filter device; the suspension was heated to 70° C. for 1 hour, then slowly cooled to room temperature; Results: FT-Raman: corresponds to Compound 1 and L-histidine |

6.6. Scale-Up Experiment 6.6.1. Magnesium Salt 1 and 2 (Mg)

In the upscaled experiments, a crystalline and an amorphous form were found.

Magnesium Salt 1 was prepared by evaporation from MeOH/CH$_2$Cl$_2$. The Raman spectrum is shown in FIG. 1; PXRD shows an amorphous form, see FIG. 2.

Magnesium Salt 2 was prepared by precipitation from THF/H$_2$O. The Raman spectrum shows a similar band pattern to that of the amorphous form Magnesium Salt 1, see FIG. 1. The PXRD pattern in FIG. 2 indicated a crystalline form. $^1$H-NMR analysis confirmed the chemical integrity of the sample.

6.6.2. Potassium Salt 1 (K)

Potassium Salt 1 was prepared by evaporation from THF/H$_2$O. The Raman spectrum is shown in FIG. 3. The PXRD pattern in FIG. 4 indicates a partly crystalline sample. $^1$H-NMR analysis confirmed the chemical integrity of the sample.

6.6.3. Sodium Salt 1 (Na)

Sodium Salt 1 was prepared by evaporation from EtOH/H$_2$O. The Raman spectrum of Sodium Salt 1 was reproduced, see FIG. 5. The PXRD pattern in FIG. 6 indicates a crystalline salt. $^1$H-NMR analysis confirmed the chemical integrity of the sample.

6.6.4. Tromethamine Salt 1 (TRO)

Tromethamine Salt 1 was prepared by evaporation from acetone/MeOH. The Raman spectrum is shown in FIG. 7. The PXRD pattern shown in FIG. 8 indicates a crystalline form. $^1$H-NMR analysis confirmed the chemical integrity of the Compound 1 free acid in the presence of tromethamine, methanol and traces of unknown impurities, e.g., degradation products (FIG. 9). While the sample contains Compound 1 ($^1$H-NMR), tromethamine was not present in a stoichiometric 1:1 ratio in the presence of additional components (Compound 1/0.5 TRO/0.5 MeOH/0.5 H$_2$O). The DVS results showed an 3% overall weight loss in the sample tested (FIG. 19), indicating the loss of methanol or hydrate formation at high relative humidity, thus leading to an overall weight loss of 4% (with loss of methanol) or 2% (with loss of methanol and replacement by water), respectively.

The correlation of peaks for the tromethamine salt by Raman spectroscopy and $^1$H-NMR was ambiguous, potential interaction with Compound 1 showed small band/peak shifts compared to the pure reference. The reference Raman and $^1$H-NMR spectra of tromethamine and methanol show bands/peaks in the same range. Thus the observed band/peak positions may indicate salt/co-crystal formation with tromethamine or solvate formation with methanol. Assignment of shifted bands/peaks to one or the other species was not possible.

Band shifts were observed in the Raman spectra. Some characteristic bands of tromethamine appear in the same wave range; however, in a salt or solvate these bands are shifted.

Likewise, in the $^1$H-NMR spectrum, peak shifts were observed with characteristic peaks of tromethamine located in the same range as methanol.

Figure 10:
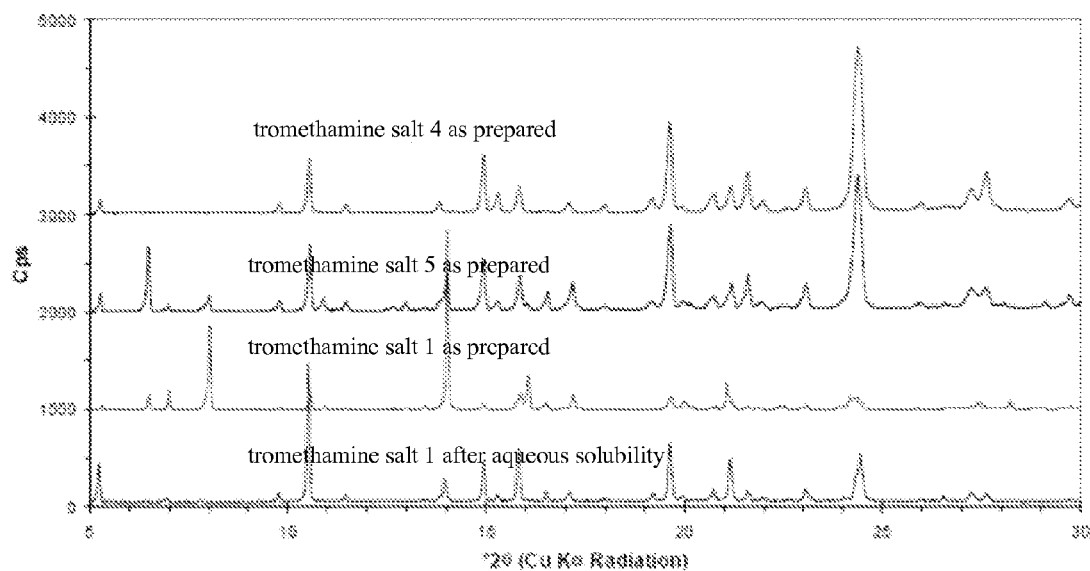
FIG. 10 depicts a superposition of PXRD patterns of a Compound 1 tromethamine salts 1, 4 and 5 as prepared, including the excess solid phase remaining from aqueous solubility testing.

FIG. 10 shows PXRD patterns of all samples prepared from the free acid and tromethamine. All patterns have many reflections in common, one or the other is missing in one or more patterns. Strong intensity variations of reflections in the same 2θ position are observed between different patterns. In case that all samples are the same phase-pure material this would indicate strong preferred orientation effects. More likely it is due to two or more forms in different mixing ratio. Still, preferred orientation effects may complicate the situation.

6.6.5. L-Lysine Salt 1 (LYS)

L-lysine Salt 1 was successfully prepared by evaporation from THF/H$_2$O. The Raman spectrum is shown in FIG. 11. The PXRD pattern in FIG. 12 indicates a crystalline salt. $^1$H-NMR analysis confirmed the chemical integrity of the sample.

6.6.6. L-Arginine Salt (ARG)

The L-arginine Salt 1 was successfully prepared by evaporation from EtOH/H$_2$O. The Raman spectrum is shown in FIG. 13. The PXRD pattern in FIG. 14 indicates a crystalline salt. $^1$H-NMR analysis confirmed the chemical integrity of the sample.

6.6.7. L-Histidine Salt 1 (HIS)

The L-histidine Salt 1 was prepared by evaporation from THF/H$_2$O. The Raman spectrum is similar to the reference spectrum obtained in the Quick-Screen, see FIG. 15. The PXRD pattern presented in FIG. 16 constitutes a mixture of Form A of Compound 1 and L-histidine.

6.7. Characterization of Potassium, Sodium, Magnesium, L-Lysine and Tromethamine Salts 6.7.1. FT-Raman, PXRD and $^1$H-NMR The potassium, sodium, magnesium, L-lysine and tromethamine salts were characterized by FT-Raman, PXRD and $^1$H-NMR, see Section 6.10. Salt formation, crystallinity and chemical integrity were confirmed. FT-Raman spectra of the salts were compared to those measured after DVS and aqueous solubility determination in Section 6.9. PXRD patterns of "as prepared" samples and the residues after equilibration in water were also compared.

6.7.2. Elemental Analysis

Generally the elemental analysis of selected samples complies with the molecular formula of the samples. For the L-lysine salt 1, EMA confirmed the presence of a monosalt (stoichiometry 1:1, salt/co-crystal former:free acid). In case of the potassium salt, a dehydrate of a mono-salt was observed by EMA. This is in agreement with the DVS measurement. For the sodium salt 1, EMA showed a hydrate formation of 1.5 water per mono-salt. This is higher than suggested by the DVS measurement which indicated no water in the starting material. For the magnesium salt 2, EMA revealed that the tetrahydrate of a hemi-salt (0.5:1, salt former:free acid) was prepared instead of a mono-salt.

For the tromethamine salt 1 the exact stoichiometry could not be determined. Clearly the sample contains Compound 1 ($^1$H-NMR), the tromethamine is not present in stoichiometry 1:1 and further components are likely present: Compound 1/0.5 TRO/0.5 MeOH/0.5 $H_2O$. DVS results with the observed overall weight loss of 3% is in agreement with the calculated sample.

TABLE 5

Elemental Analysis of Potassium Salt 1.

| | C | H | N | O | F | K |
|---|---|---|---|---|---|---|
| found | 50.20 | 3.40 | 7.81 | 22.41 | 5.17 | 11.0 |
| calculated | 50.42 | 3.10 | 7.84 | 22.39 | 5.32 | 10.94 |

Formula: $C_{15}H_9FN_2O_2$ K 2 $H_2O$

TABLE 6

Elemental analysis of sodium salt 1.

| | C | H | N | O | F | K |
|---|---|---|---|---|---|---|
| found | 54.69 | 3.26 | 8.48 | 20.83 | 5.69 | 6.60 |
| calculated | 54.14 | 3.18 | 8.42 | 21.64 | 5.71 | 6.91 |

Formula: $C_{15}H_9FN_2O_2$ Na 1.5 $H_2O$

TABLE 7

Elemental analysis of tromethamine salt 1.

| | C | H | N | O | F |
|---|---|---|---|---|---|
| found | 58.15 | 4.82 | 9.46 | 21.40 | 5.16 |
| calculated $C_{15}H_9FN_2O_2$ MeOH $H_2O$ | 57.66 | 4.23 | 8.41 | 24.00 | 5.70 |
| calculated $C_{15}H_9FN_2O_2$ $C_4H_{11}NO_3$ | 56.29 | 4.97 | 10.37 | 23.68 | 4.69 |
| calculated $C_{15}H_9FN_2O_2$ 0.5 TRO 0.5 MeOH 0.5 $H_2O$ | 56.91 | 4.64 | 9.48 | 23.82 | 5.14 |

Compound 1: $C_{15}H_9FN_2O_2$
Tromethamine: $C_4H_{11}NO_3$

TABLE 8

Elemental analysis of L-lysine salt 1.

| | C | H | N | O | F |
|---|---|---|---|---|---|
| found | 57.28 | 4.95 | 11.9 | 19.75 | 4.62 |
| calculated | 58.60 | 5.39 | 13.02 | 18.58 | 4.41 |

Formula: Compound 1: $C_{15}H_9FN_2O_2$
L-lysine: $C_6H_{14}N_2O_2$

TABLE 9

Elemental analysis of magnesium salt 2.

| | C | H | N | O | F | Mg |
|---|---|---|---|---|---|---|
| found | 48.18 | 4.03 | 7.25 | 29.13 | 5.04 | 3.85 |
| calculated salt | 49.44 | 3.60 | 7.69 | 30.73 | 5.21 | 3.33 |

Formula: $C_{15}H_9FN_2O_2$ 0.5 Mg 4 $H_2O$

6.8. DVS

DVS measurements (50%→0%→95%→50% r.h.) were performed on the samples of potassium salt 1, sodium salt 1, tromethamine salt 1, L-lysine salt and magnesium salt 2.

Figure 17:
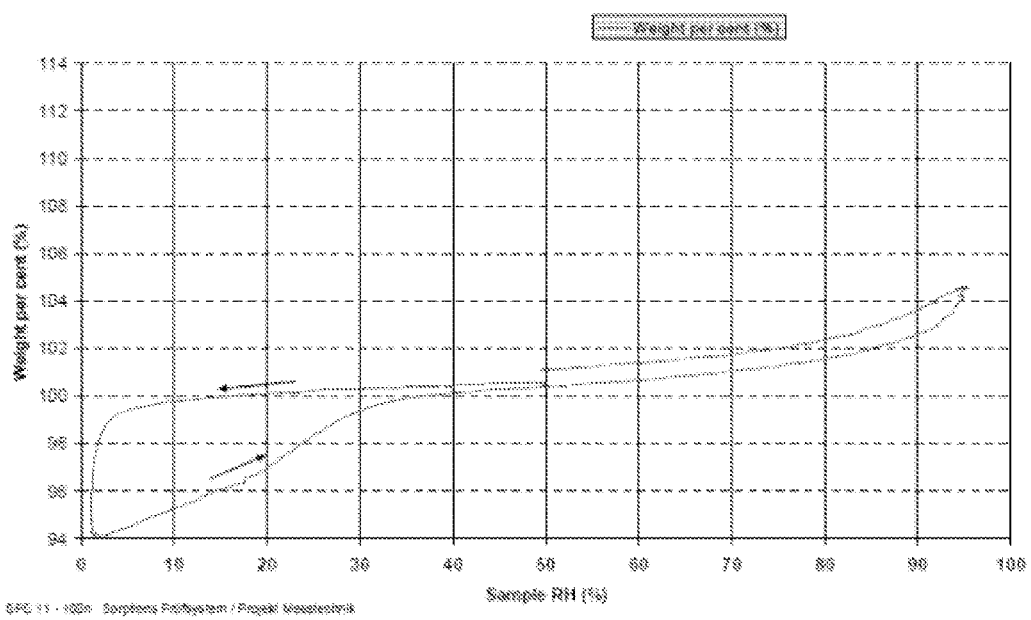
FIG. 17 depicts a Dynamic Vapor Sorption (DVS) of a Compound 1 potassium salt 1 that shows a reversible water release (left arrow) and a small irreversible water uptake (right arrow) with hysteresis.

In FIG. 17 the DVS of the potassium salt shows a mass loss of ~6 wt. % as the humidity is decreased to 0% r.h. (equilibrium not reached) followed by a continuous water uptake from 0% to 35% r.h. recovering the original mass. Water release of ~5 wt. % would correspond to loss of one stoichiometric water. As the humidity was further increased to 80% r.h. more water was taken up slowly (~1.5 wt. % mass change), and from 80% to 95% r.h. a rapid water uptake of roughly 3 wt. % was observed (equilibrium reached). Upon lowering the relative humidity again, the water content decreased and remained at a slightly higher value (~1 wt. %) than the original mass. The behavior around 0% r.h. strongly suggests the presence of an ansolvate or desolvated hydrate form.

Figure 18:
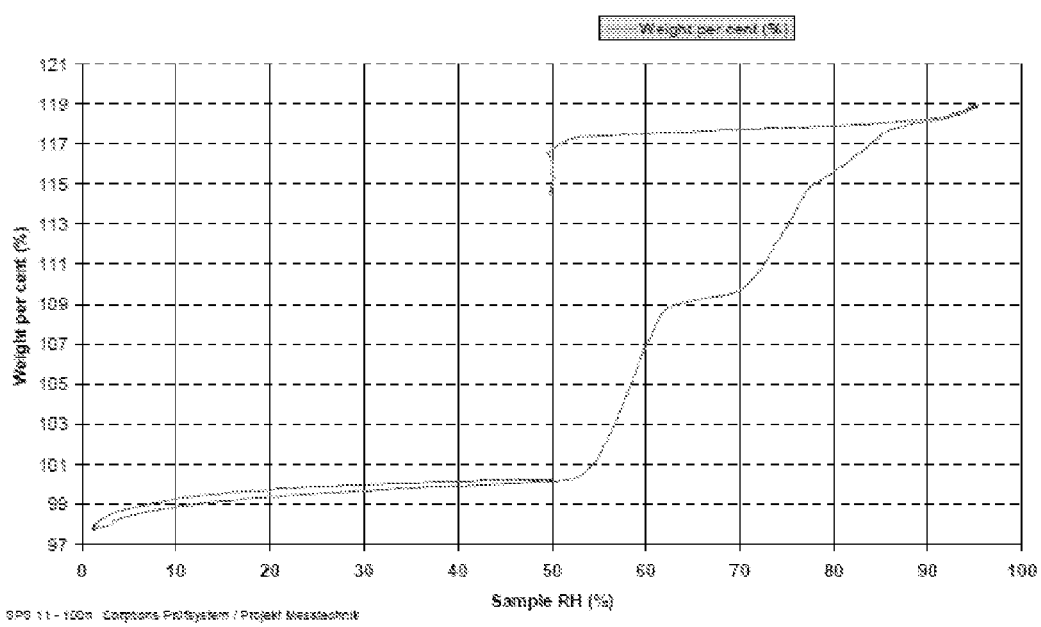
FIG. 18 depicts a DVS of a Compound 1 sodium salt 1 that shows a stepwise irreversible water uptake.

In FIG. 18 the DVS of the sodium salt shows water uptake in approximately steplike fashion, suggesting the formation of various hydrates Upon decreasing the humidity from 50% to 0% r.h. and again increasing to 50% r.h. the sample shows reversible weight loss and weight gain of 2 wt. %. Approximately 10 wt. % water uptake in one step (dehydrate formation) were observed from 50% to 62% r.h. In a second step further water (~6 wt. % corresponding to trihydrate formation) was taken up as the humidity was increased to 80% r.h. (equilibrium not reached). Further water was taken up to a total of 20 wt. % (corresponding to tetrahydrate formation) at 95% r.h. Upon lowering the relative humidity to 50% r.h., the water content decreased and remained at ~16 wt. % higher than the original mass (14 wt. % would correspond to a trihydrate), but equilibrium was not reached during this experiment. FT-Raman spectra were recorded before and after DVS measurement. The spectra clearly show that the sodium salt sample was converted into a new form.

FT-Raman investigation of the salt after DVS measurement confirmed that the sample was converted into a new form.

In FIG. 19 the DVS of the tromethamine salt shows no significant mass change as the humidity was decreased to 0% r.h. and then raised to 80% r.h. From 80% to 95% r.h. the sample takes up ~25 wt. % (equilibrium reached) reversibly. Below 70% r.h. further weight loss to a value 3 wt. % lower than the original mass was observed.

Figure 20:
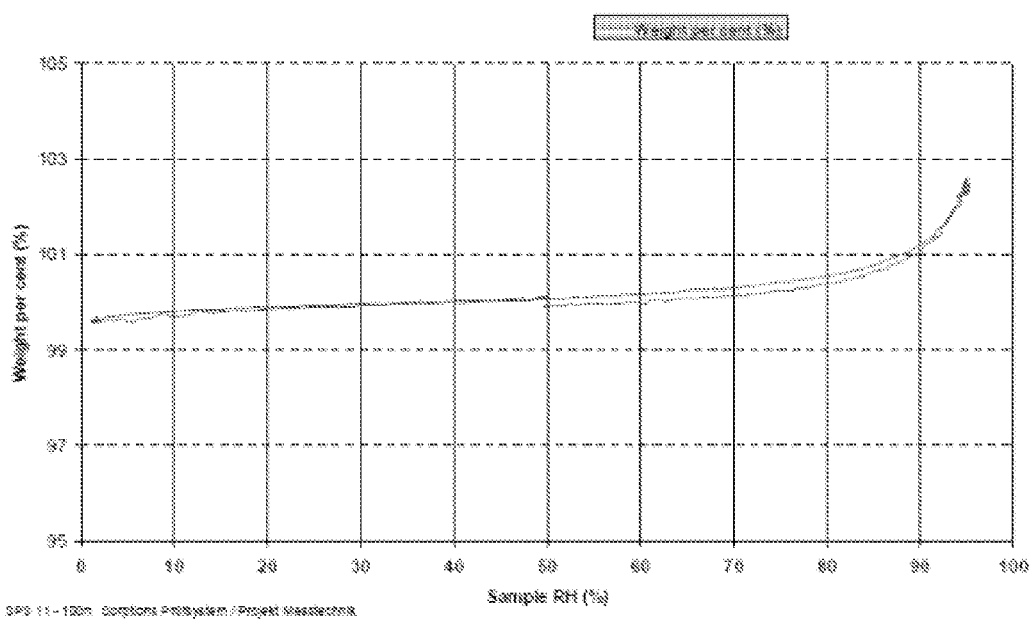
FIG. 20 depicts a DVS of a Compound 1 L-lysine salt 1 that shows a small reversible water uptake.

In FIG. 20 the DVS of the L-lysine salt shows a nearly reversible water uptake and release. Water was taken up as the humidity was increased to 95% r.h. (~2 wt. % mass change, equilibrium reached). Upon lowering the relative humidity again, the water content decreased and reverted nearly to the original mass.

Figure 21:
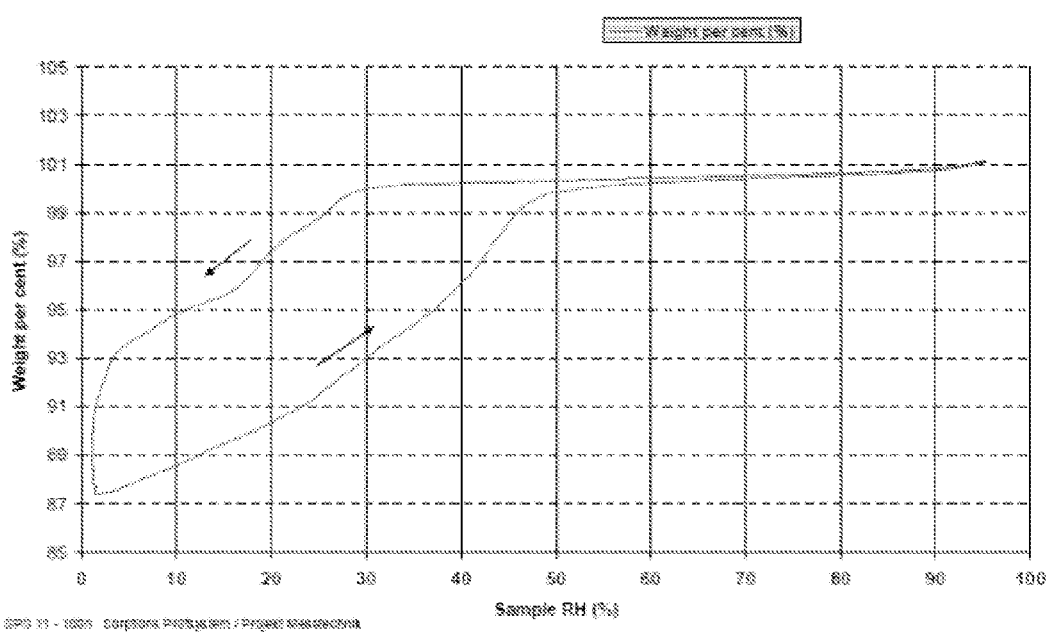
FIG. 21 depicts a DVS of a Compound 1 magnesium salt 2 that shows a large water release (left arrow) with hysteresis (right arrow).
Figure 22:
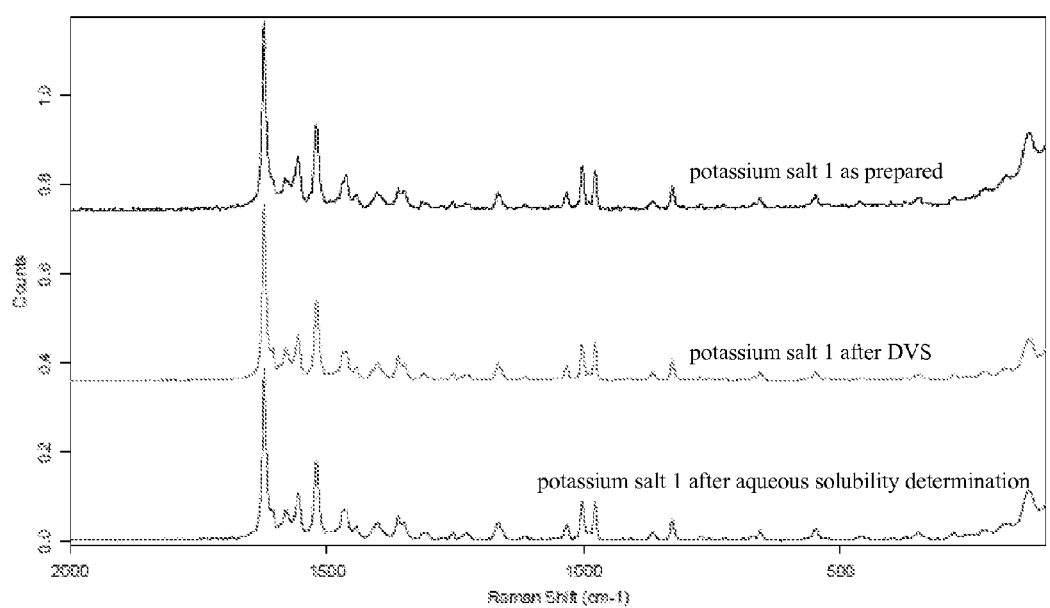
FIG. 22 depicts superposed FT-Raman spectra of a Compound 1 potassium salt 1 as prepared (bottom), after DVS (middle) and residue from aqueous solubility determination (top).
Figure 23:
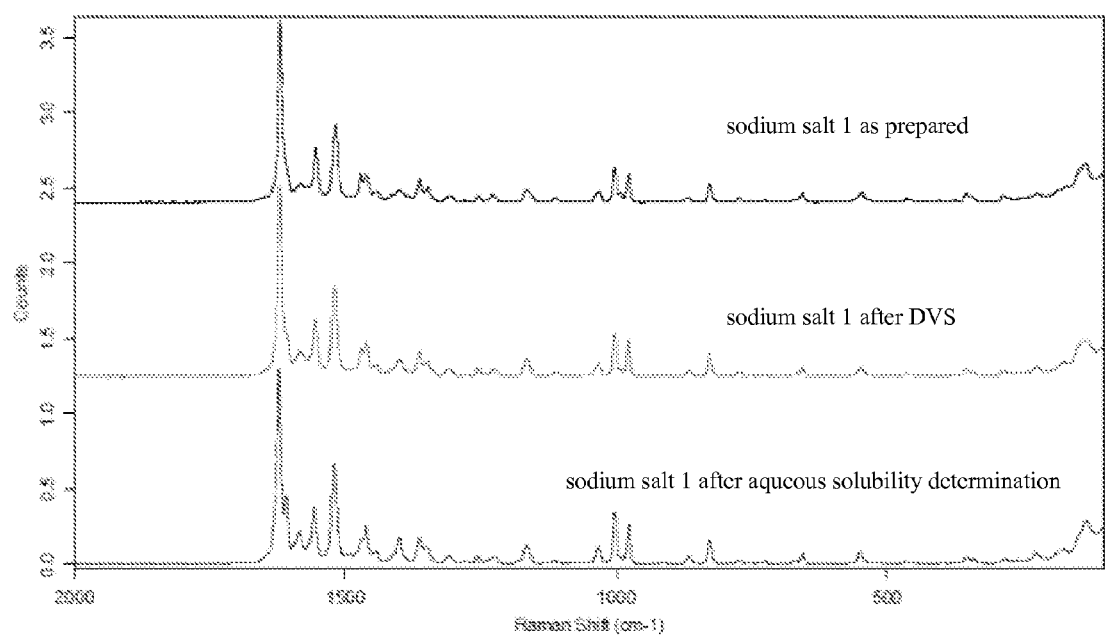
FIG. 23 depicts superposed FT-Raman spectra of a Compound 1 sodium salt 1 as prepared (bottom), after DVS (middle) and residue from aqueous solubility determination (top).
Figure 24:
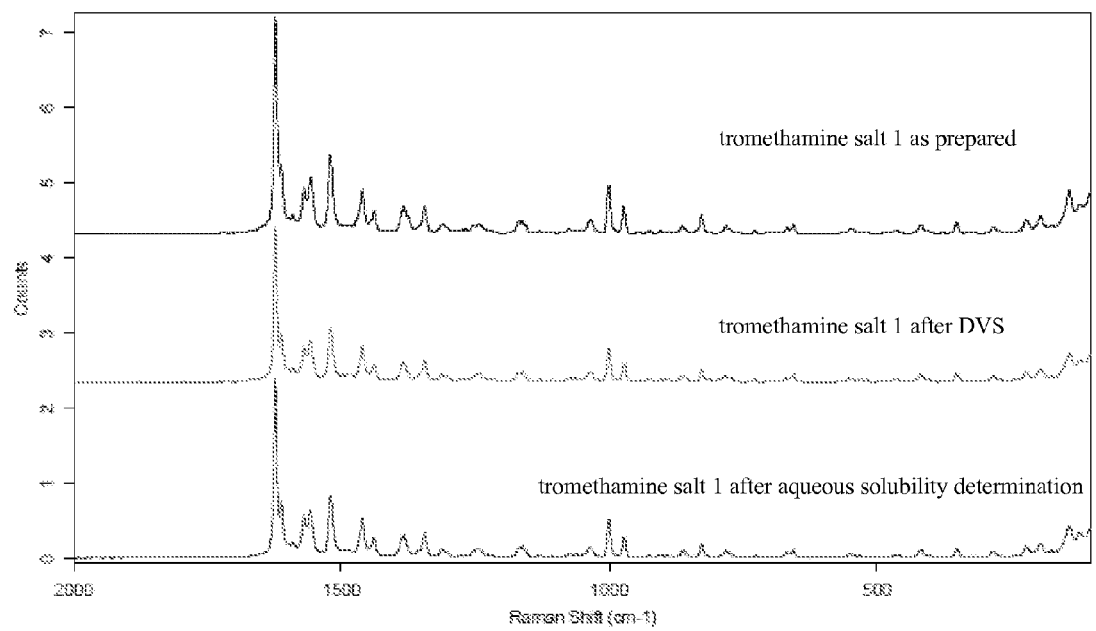
FIG. 24 depicts superposed FT-Raman spectra of a Compound 1 tromethane salt 1 as prepared (bottom), after DVS (middle) and residue from aqueous solubility determination (top). No differences are observed in the spectra.
Figure 25:
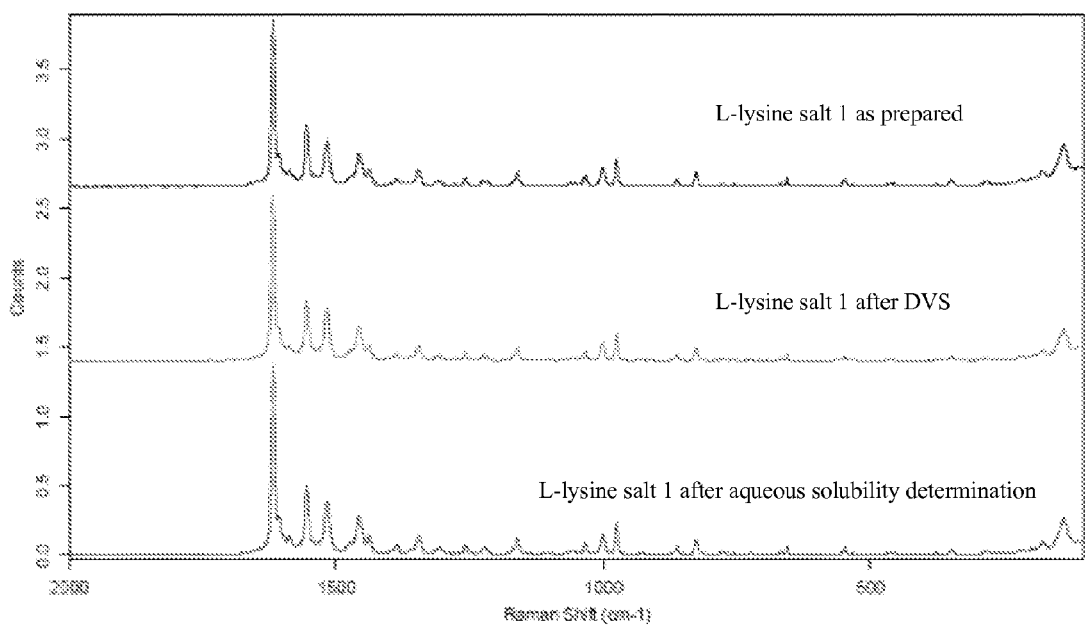
FIG. 25 depicts superposed FT-Raman spectra of a Compound 1 L-lysine salt 1 as prepared (bottom), after DVS (middle) and residue from aqueous solubility determination (top).
Figure 26:
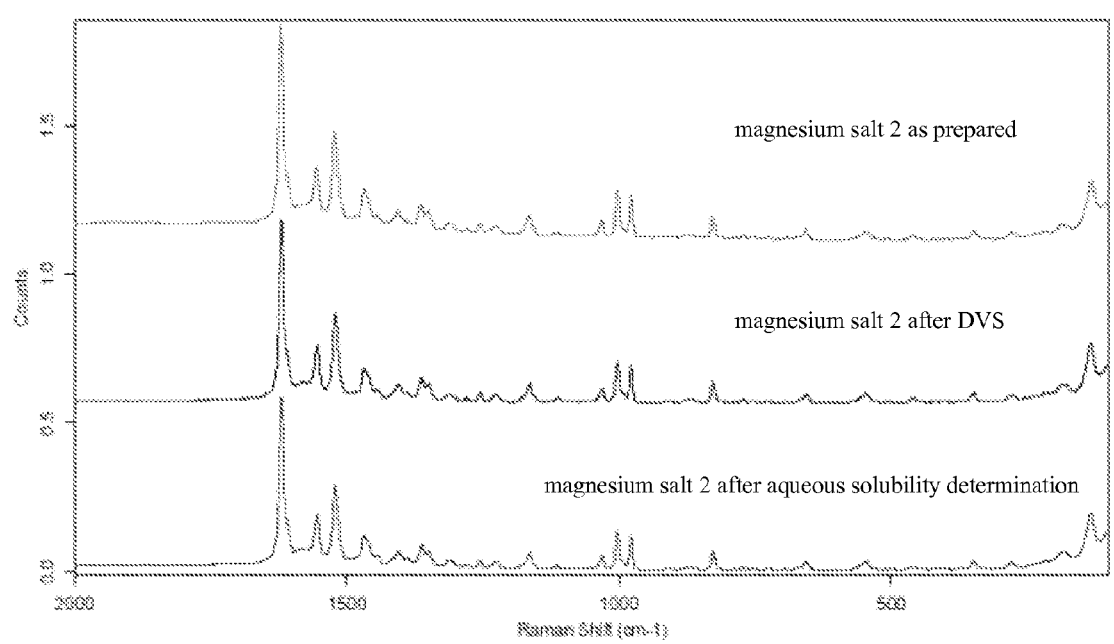
FIG. 26 depicts superposed FT-Raman spectra of a Compound 1 magnesium salt 2 as prepared (bottom), after DVS (top) and residue from aqueous solubility determination (middle).
Figure 27:
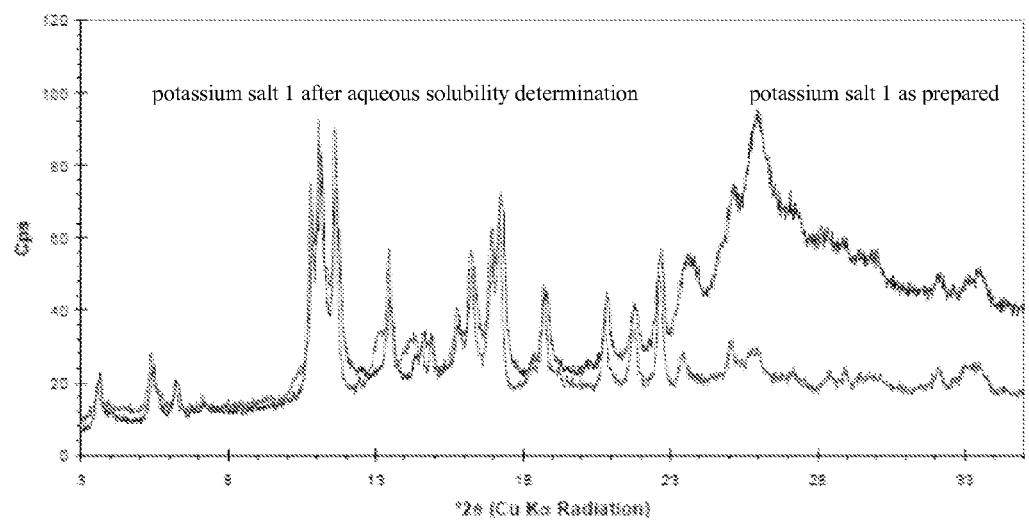
FIG. 27 depicts superposed PXRD patterns of a Compound 1 potassium salt 1 as prepared (high peaks on right) and after aqueous solubility (lower peaks on right).
Figure 28:
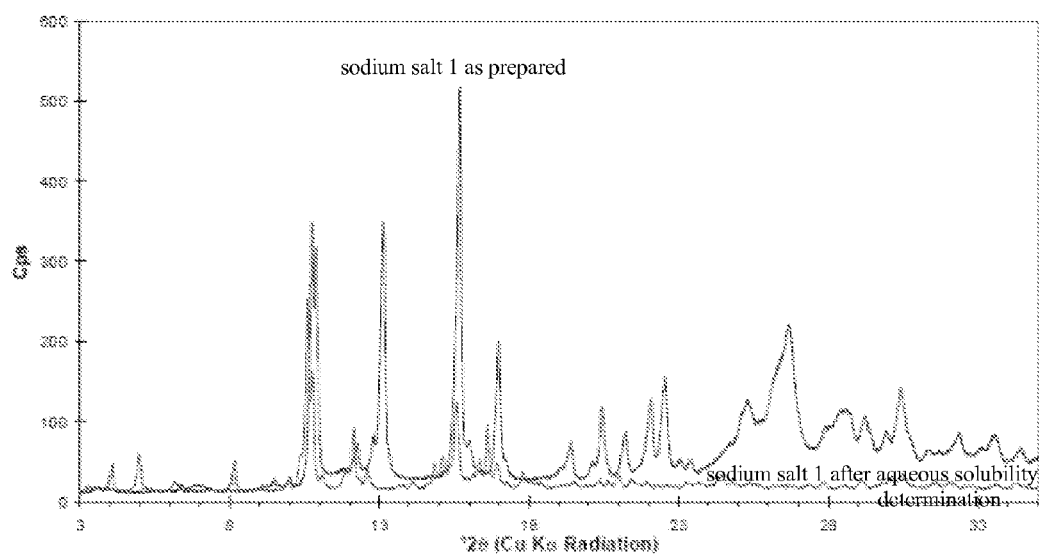
FIG. 28 depicts superposed PXRD patterns of a Compound 1 sodium salt 1 as prepared and after aqueous solubility.
Figure 29:
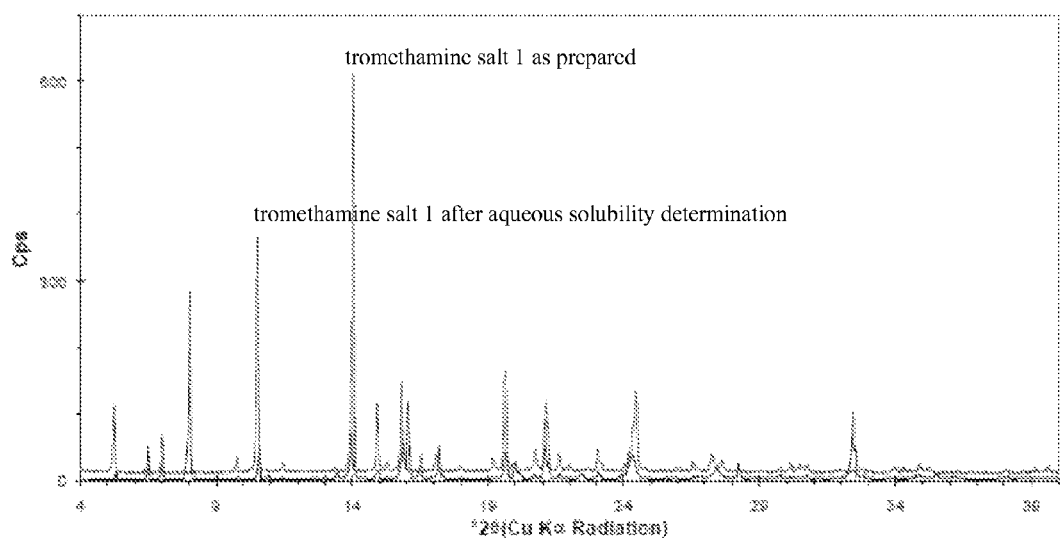
FIG. 29 depicts superposed PXRD patterns of a Compound 1 tromethane salt 1 as prepared and after aqueous solubility.
Figure 30:
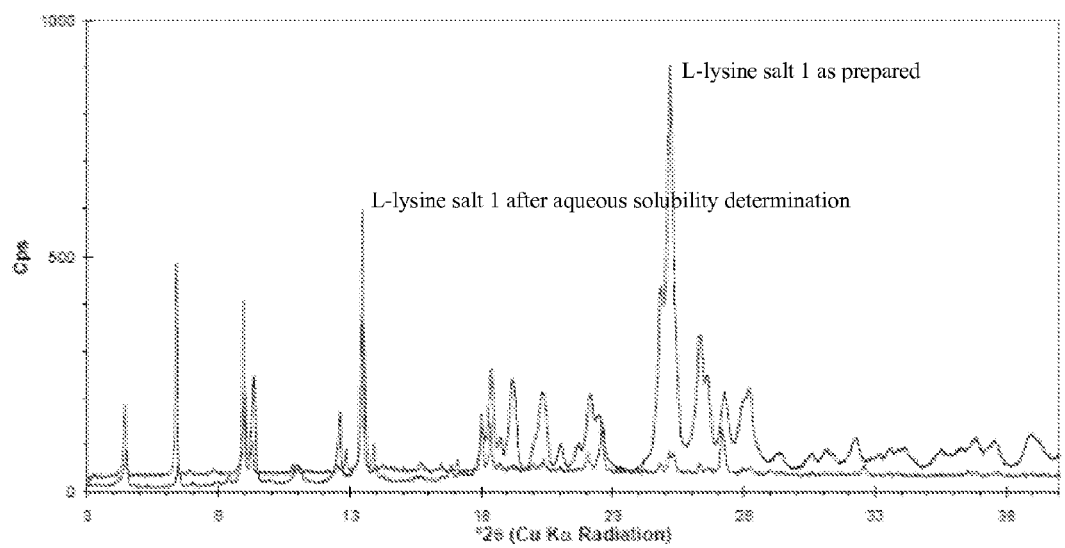
FIG. 30 depicts a superposed PXRD patterns of a Compound 1 L-lysine salt 1 as prepared and after aqueous solubility.
Figure 31:
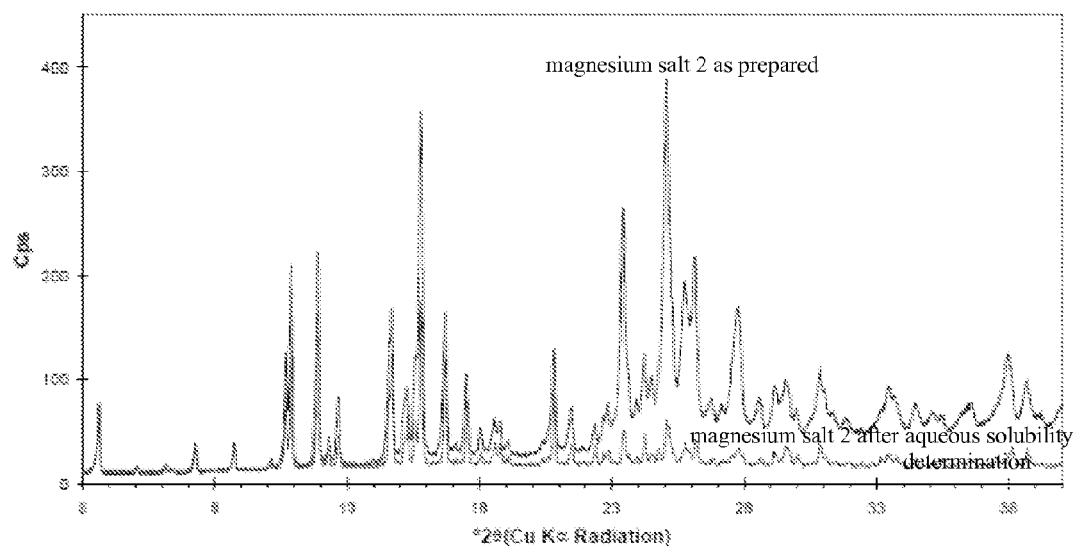
FIG. 31 depicts a superposed PXRD patterns of a Compound 1 magnesium salt 2 as prepared (higher peaks) and after aqueous solubility (lower peaks).

In FIG. 21 the DVS of the magnesium salt shows a nearly reversible water uptake and release. Upon decreasing the humidity from 50% to 0% r.h. and again increasing to 50% r.h. the sample shows reversible mass change of ~13 wt. % (equilibrium not reached). At higher humidity no significant mass change was detected. The observed mass change is in agreement with the EMA results corresponding to a tetrahydrate of a hemi-salt $Mg_{0.5}$/Compound $1/4H_2O$.

6.9. Aqueous Solubility Determination

Each salt was suspended in water and shaken for 24 h at 25° C. and 500 rpm. The resulting suspensions were filtered (0.1 µm filter). The obtained solid residues were analyzed by FT-Raman. The pH of the filtrate was measured, and the concentration of the free acid was determined by HPLC. The values are given in Table 10. The solubility of magnesium salt 2 is remarkably low. The salt was precipitated from solutions in a stoichiometry 1:1 of magnesium:free acid. The EMA result corresponds to a hemi-salt with a stoichiometry of 0.5:1, magnesium:free acid.

The FT-Raman spectra measured on samples as prepared and after aqueous solubility determination are shown from FIG. 22 to FIG. 26. In FT-Raman spectra measured on salts of L-lysine and tromethamine no new forms are observed. The FT-Raman spectra measured on the potassium salt show slight band shifts, suggesting the uptake of water. Slight band shifts and traces of magnesium hydroxide are observed in spectra of the magnesium salt. The spectra measured on the sodium salt show different forms.

The PXRD patterns measured on samples as prepared and after aqueous solubility determination are shown from FIG. 27 to FIG. 31. PXRD patterns measured on the potassium and magnesium salt show no new forms. The PXRD pattern of the L-lysine salt shows the same form, but after treatment in water the reflections are stronger and sharper and the pattern shows different sample orientation. The PXRD patterns of the sodium salt show different forms in agreement with the Raman spectra.

TABLE 10

Aqueous solubility of the potassium, sodium, tromethamine, L-lysine and magnesium salts.

| Sample | Solubility (mg/mL) | pH | FT-Raman | PXRD |
|---|---|---|---|---|
| Potassium salt 1 | 57 | 9.2 | same form | slight band shifts |
| Sodium salt 1 | 22 | 8.3 | different forms | different forms |
| Tromethamine salt 1 | 18 | 8.1 | unclear situation | unclear situation |
| L-lysine salt 1 | 15 | 7.7 | same form | same form |
| Magnesium salt 2 | 0.44 | 9.1 | same form | same form |

6.10. Instrumental and Typical Measurement Conditions

| | | |
|---|---|---|
| Raman Microscopy | Renishaw RM 1000. Stabilized diode laser 785 nm excitation, NIR-enhanced Peltier-cooled CCD camera as detector. Measurements were carried out with a long working distance 20x objective. Measurement range 2000-100 $cm^{-1}$. | |
| FT-Raman Spectroscopy | Bruker RFS100. Nd: YAG 1064 nm excitation, 300 mW laser power, Ge detector, 64 scans, range 25-3500 $cm^{-1}$, 2 $cm^{-1}$ resolution. | |
| PXRD | Bruker D8; Copper Kα radiation, 40 kV/40 mA; LynxEye detector, 0.025 2θ, step size, 37 s step time. Sample preparation: The samples were generally measured without any special treatment other than the application of slight pressure to get a flat surface. Silicon single crystal sample holder types: a) standard holder for polymorphism screening, 0.1 mm deep, less than 20 mg sample required; b) 0.5 mm deep, 12 mm cavity diameter for c. 40 mg; c) 1.0 mm deep, 12 mm cavity diameter for c. 80 mg. All samples measured on the Bruker D8 are rotated during the measurement. | |
| DVS | Projekt Messtechnik SPS 11-100n multi-sample water vapor sorption analyzer. The sample was allowed to equilibrate at 50% r.h. before starting a predefined humidity program. Program: 50% r.h. → 0% r.h. → 96% r.h. – 50% r.h., Δr.h. = 5%/h Hygroscopicity was classified according to the European Pharmacopoeia: | |
| | very hygroscopic: | increase of the mass ≥15% |
| | hygroscopic: | increase of the mass is less than 15% and equal or greater than 2% |
| | slightly hygroscopic: | increase of the mass is less than 2% and equal or greater than 0.2% |
| | not hygroscopic: | increase of the mass is less than 0.2% |
| | deliquescent: | sufficient water is absorbed to form a liquid |
| NMR | The $^1$H-NMR spectra were recorded at 300.13 MHz on Bruker DPX300 instrument. | |
| EMA | Elemental analysis of F was performed by an fluoride-sensitive electrode after preceding Wurzschmitt digestion and adsorption in aqueous solution. Elemental analysis was performed for C, H and N by dry combustion using either a Leco CHN 800 or Leco CHNS 932 instrument. Elemental analysis of O was performed by pyrolysis using a Leco RO-478 instrument. Elemental analysis of K, Na and Mg was performed by atomic absorption spectrometry. | |
| Solubility determination | Suspension agitated with a temperature controlled "Thermomixer comfort" from Eppendorf with 500 rpm (24 hours, 25° C.). Filtered with Millipore Centrifugal Filter Device UFC30VVNB (0.1 µm) and Centrifuge Hettich EBA 12 R (10,000 g). | |
| HPLC | Equipment | TSP HPLC (UV3000, AS3000, P4000, SCM1000 Soft. Version 4.1) |
| | Column | Waters, Xterra MS C18 4.6 × 100 mm, 5 µm (CC01) |
| | Mobile phase A | distilled $H_2O$ + 0.1% TFA |
| | Mobile phase B | ACN + 0.1% TFA |
| | Reference Concentration | ca. 0.04 mg/mL |
| | Retention time | 5.8 min |

| | | |
|---|---|---|
| Gradient | 0.0 min | 55% A/45% B |
| | 10.0 min | 55% A/45% B |
| Flow | 1.0 mL/min | |
| Injection volume | 10 μL | |
| Wavelength | 241 nm | |

6.11. Comparative Equilibrium Solubility Study of Micronized and Non-Micronized Compound 1

Objective: The purpose of this study was to evaluate the solubility of micronized and non-micronized Compound 1. The solubility study was conducted in two representative media in pH 1 (0.1 N HCl with 0.5% sodium lauryl sulfate) and in pH 7.4 (0.1M phosphate buffered saline). The experiment further compared the initial rate of dissolution and equilibrium solubilities of micronized and non-micronized Compound 1 over a period of time.

Experimental:

Experimental materials included: 1) micronized Compound 1; 2) non-micronized Compound 1; 3) acetic acid, glacial; 4) triethyl amine; 5) acetonitrile, HPLC grade; 6) 10 mL syringe; and 7) 0.45 μm PTFE syringe filters.

Media used for solubility study included: 1) pH 1.0 comprising 0.1N Hydrocholric acid (HCl) with 0.5% sodium lauryl sulfate (SLS); and 2) pH 7.4 comprising 0.1M phosphate buffered saline (PBS).

Equipment for solubility study included: 1) Waters 2795 Separations Module; 2) Axiovert 200 Microscope; and 3) Analytical grade balance.

HPLC conditions used for solubility study are provided in Table 11 and Table 12.

TABLE 11

HPLC conditions used for solubility study

| | |
|---|---|
| Column | Sunfire C18 4.6 × 50 mm |
| Column Temperature | 40° C. |
| Mobile Phase A | 0.3% acetic acid with 0.1% triethyl amine; pH 4.5 adjusted by 10% (v/v) NH₄OH |
| Mobile Phase B | Acetonitrile |
| Flow rate | 1.5 mL/min |
| Injection volume | 10 μL |
| Detection | UV 254 nm |
| Run time | 15 minutes |
| Gradient | ~3.22 minutes |

TABLE 12

HPLC gradient used for solubility study

| Time (minutes) | % Mobile Phase A | % Mobile Phase B |
|---|---|---|
| 0 | 70 | 30 |
| 10 | 30 | 70 |
| 15 | 70 | 30 |

Solubility measurement procedure comprised the steps of: 1) weighing and mixing approximately 100 mg of micronized Compound 1 and 100 mL of 0.1N HCl with 0.5% SLS into amber jar 1; 2) weighing and mixing approximately 100 mg of micronized Compound 1 and 100 mL of PBS into amber jar 2; 3) weighing and mixing approximately 100 mg of non-micronized Compound 1 and 100 mL of 0.1N HCl with 0.5% SLS into amber jar 3; 4) weighing and mixing approximately 100 mg of non-micronized Compound 1 and 100 mL of PBS into amber jar 4; 5) mixing all samples in their respective amber jars using a multi purpose rotator for 2 hours; 4) sampling at 5 minutes, 10 minutes, 30 minutes, 60 minutes, 90 minutes, 120 minutes; 5) filtering the samples and 6) analyzing the filtrates using HPLC. For each time point, 10 mL of sample was drawn using a 10 mL syringe with a needle attached filter and using a syringe-top 0.45 μm PTFE syringe filter. The first 9 mL of the samples collected were put back into the original amber jar and then remaining 1 mL was transferred to HPLC vial for analysis.

Figure 32:
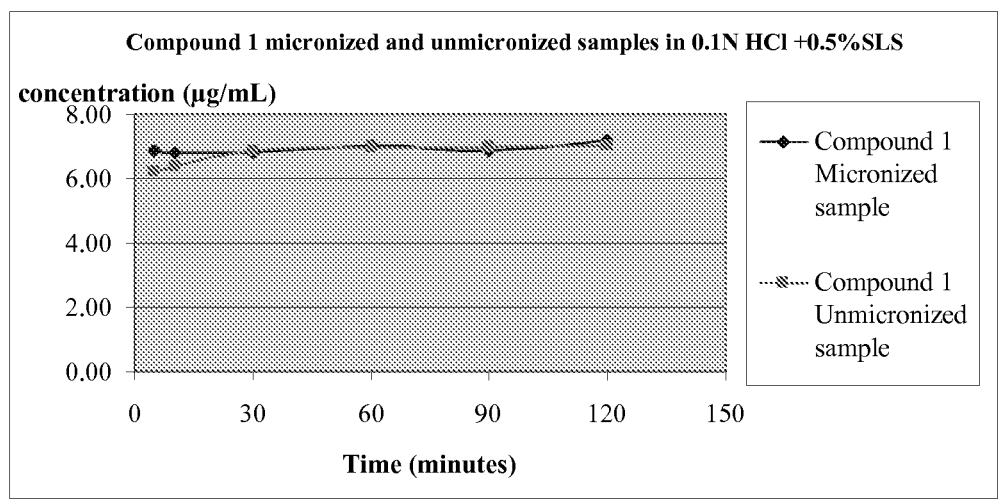
FIG. 32 depicts graphical representation of the solubility profiles of micronized and non-micronized Compound 1 in 0.1N HCl containing 0.5% sodium lauryl sulfate.
Figure 33:
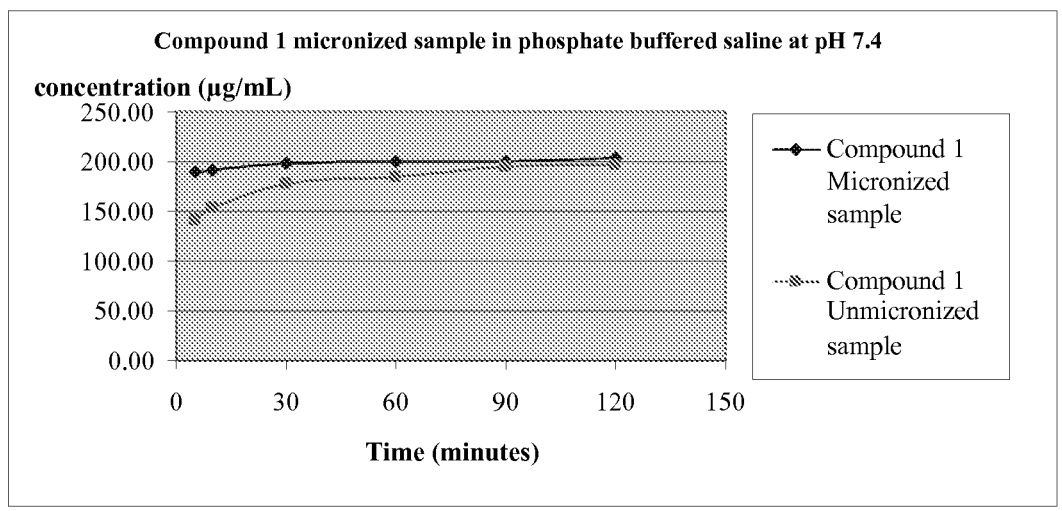
FIG. 33 depicts graphical representation of the solubility profiles of micronized Compound 1 in phosphate buffered saline at pH 7.4.

Solubility study results for micronized and non-micronized Compound 1 are provided in Table 13. FIG. 32 and FIG. 33 provide graphical representation of the solubility profiles of micronized and non-micronized Compound 1 in 0.1N HCl with 0.5% SLS and PBS, respectively.

TABLE 13

Time vs Concentration solubility data for micronized and non-micronized Compound 1

| | Concentration of Compound 1 in 0.1N HCl + 0.5% SLS (μg/mL) | | Concentration of Compound 1 in PBS (μg/mL) | |
|---|---|---|---|---|
| Time (Minutes) | Micronized | Non-Micronized | Micronized | Non-Micronized |
| 5 | 6.85 | 6.24 | 189.13 | 141.89 |
| 10 | 6.81 | 6.38 | 191.45 | 152.59 |
| 30 | 6.83 | 6.87 | 197.59 | 176.92 |
| 60 | 7.04 | 6.99 | 199.95 | 185.18 |
| 90 | 6.88 | 6.97 | 200.29 | 194.06 |
| 120 | 7.18 | 7.04 | 203.08 | 196.54 |

Figure 34:
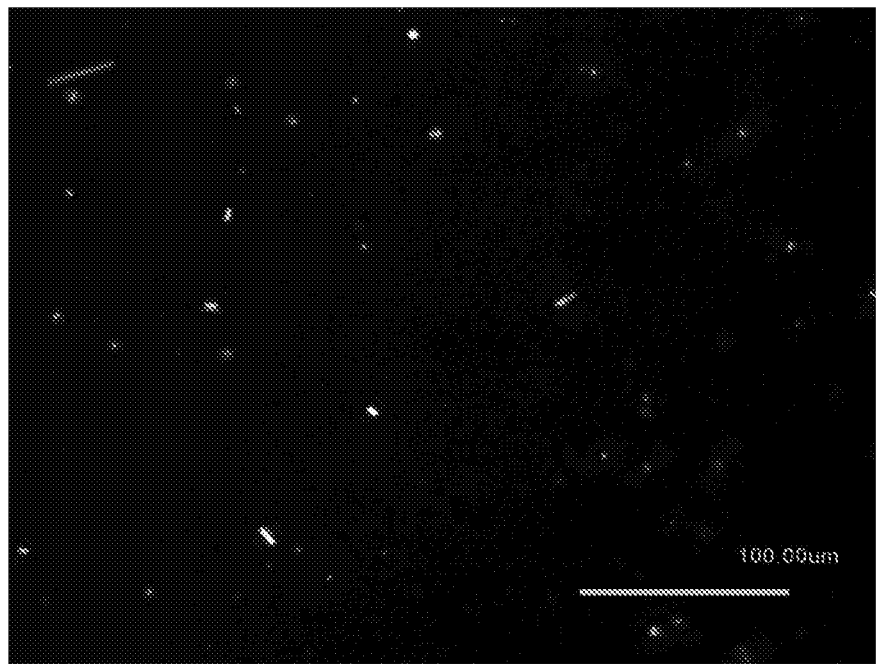
FIG. 34 depicts the images under polarized light of micronized samples of Compound 1.
Figure 35:
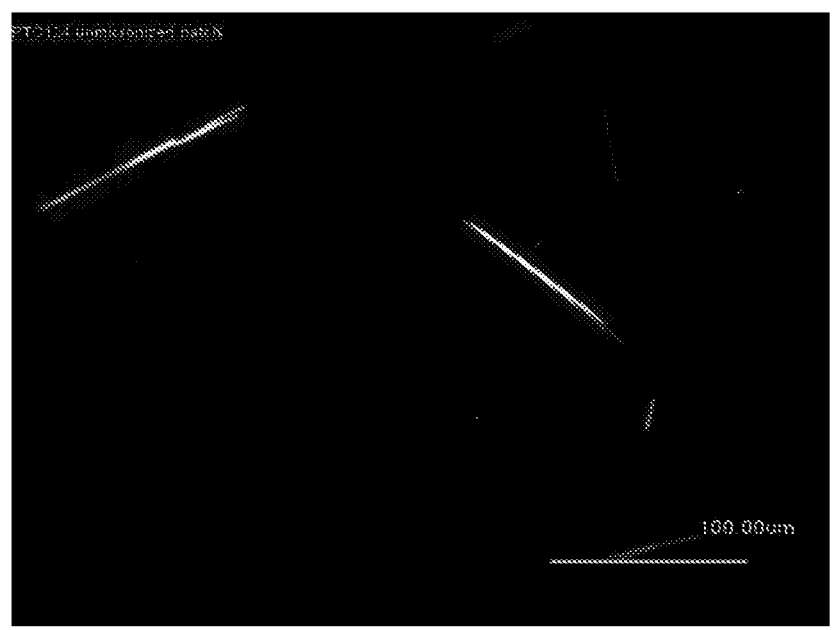
FIG. 35 depicts the images under polarized light of non-micronized samples of Compound 1.

Micronized and non-micronized batches of Compound 1 were observed and analyzed under microscope to obtain an estimate of the average length and average width of the particles. As a part of the process, 5 different samples from each type of Compound 1 were analyzed under Axiovert 200 microscope, using a program called IPLab 3.7 and the the particle size measurements were estimated. The analysis results are provided in Table 14. FIG. 34 and FIG. 35 provide the images under polarized light of non-micronized and micronized samples of Compound 1.

TABLE 14

Estimated average particle size data for micronized and non-micronized Compound 1

| | Micronized Compound 1 | | Non-Micronized Compound 1 | |
|---|---|---|---|---|
| Sample | Length (μM) | Width (μM) | Length (μM) | Width (μM) |
| 1 | 6.7 | 4.0 | 34.3 | 3.6 |
| 2 | 5.2 | 3.3 | 28.5 | 3.7 |
| 3 | 5.3 | 3.3 | 34.3 | 4.4 |
| 4 | 7.1 | 4.1 | 37.4 | 3.8 |
| 5 | 5.6 | 3.7 | 30.7 | 4.2 |
| Average | 5.9 | 3.6 | 33.0 | 4.4 |

Summary: A kinetic phenomenon was observed in both pH media at early time points. In pH 1 media, there was a small difference in kinetic solubility for micronized and non-micronized Compound 1; while in pH 7.4, the difference was significantly increased.

In both media, Compound 1 solubility appears to reach the same value. In pH 1 media, the equilibrium was reached at approximately 30 minutes. In pH 7.4 media, the equilibrium solubility was reached at approximately 2 hours.

In pH 7.4 media, the difference in kinetic solubility is significant, indicating that small particles do have a significant impact in enhancing Compound 1 drug substance solubilization.

6.12. Ophthalmic Formulations

Table 15 provides an ophthalmic formulation as a solution comprising Compound 1 in combination with tromethamine used as a cationic modifier.

| Ingredient | Concentration |
| --- | --- |
| Compound 1 | 0.2% |
| Tromethamine HCl | 1.0% |
| Mannitol | 2.0% |
| Boric Acid | 1.0% |
| Disodium Edetate | 0.025% |
| Benzalkonium Chloride | 0.01% |
| NaOH/HCl (adjust pH) | pH 7.2 |
| Water (dilute to volume) | p.r.n. |

Table 16 provides an ophthalmic formulation as a solution comprising Compound 1 in combination with histidine used as a cationic modifier.

| Ingredient | Concentration |
| --- | --- |
| Compound 1 | 0.1% |
| Histidine HCl | 0.5% |
| Sorbitol | 3.0% |
| Disodium Edetate | 0.025% |
| Benzalkonium Chloride | 0.01% |
| NaOH/HCl (adjust pH) | pH 6.5 |
| Water (dilute to volume) | p.r.n. |

Table 17 provides an ophthalmic formulation as a solution comprising Compound 1 in combination with Lysine used as a cationic modifier.

| Ingredient | Concentration |
| --- | --- |
| Compound 1 | 0.05% |
| Lysine HCl | 0.5% |
| Mannitol | 4.0% |
| Disodium Edetate | 0.025% |
| Benzalkonium Chloride | 0.01% |
| NaOH/HCl (adjust pH) | pH 7.5 |
| Water (dilute to volume) | p.r.n. |

Table 18 provides an ophthalmic formulation as a solution comprising Compound 1 in combination with DEAE-Dextran used as a cationic modifier.

| Ingredient | Concentration |
| --- | --- |
| Compound 1 | 0.5% |
| DEAE-Dextran | 0.5% |
| Trehalose | 2.0% |
| Boric Acid | 1.0% |
| Disodium Edetate | 0.025% |
| Benzalkonium Chloride | 0.01% |
| NaOH/HCl (adjust pH) | pH 7.2 |
| Water (dilute to volume) | p.r.n. |

Table 19 provides an ophthalmic formulation as a solution comprising Compound 1 in combination with hydroxypropyl β-cyclodextrin used as a cationic modifier.

| Ingredient | Concentration |
| --- | --- |
| Hydroxypropyl β-Cyclodextrin | 10% |
| Compound 1 | 0.5% |
| Tromethamine HCl | 0.5% |
| Mannitol | 2.0% |
| Dextran | 1.0% |
| Boric Acid | 1.0% |
| Disodium Edetate | 0.025% |
| Benzalkonium Chloride | 0.01% |
| NaOH/HCl (adjust pH) | pH 7.2 |
| Water (dilute to volume) | p.r.n. |

6.13. In Vivo Assays

Two studies were performed to evaluate the concentrations of Compound 1/metabolites in various tissues, including the eyes, following a single dose administration of radiolabeled Compound 1 ($^{14}$C-3-[5-(2-fluoro-phenyl)-[1,2,4]oxadiazol-3-yl]benzoic acid) to Sprague Dawley and Long Evans rats.

Sprague Dawley rats: As part of a quantitative whole body autoradiography (QWBA) study, 4 male and 4 female Sprague Dawley rats (albino) obtained from Charles River were administered a single oral gavage dose of 50 mg/kg $^{14}$C-3-[5-(2-fluoro-phenyl)-[1,2,4]oxadiazol-3-yl]benzoic acid.

Animals were individually housed and certified rodent diet and water were provided ad libitum. Animals were acclimated for 8 days prior to dose administration. Environmental controls for the animal room were set to maintain a temperature of 18 to 26° C., a relative humidity of 50±20%, and a 12-hour light/12-hour dark cycle. The 12-hour dark cycle may have been interrupted to accommodate study procedures. Animals were fasted overnight through 4 hours postdose on the day of dosing. At dosing, the animals weighed 204 to 260 g and were approximately 9 to 11 weeks of age. One animal/sex/timepoint was sacrificed with an overdose of halothane at 1, 4, 24, and 72 hours postdose and carcasses were collected for analysis by whole-body autoradiography (WBA). The concentrations of $^{14}$C-3-[5-(2-fluoro-phenyl)-[1,2,4]oxadiazol-3-yl]benzoic acid in the eye and related tissues are shown in the following table.

TABLE 20

Concentrations of radioactivity in eyes and related tissues determined by whole body autoradiography at specified times following a single oral administration of $^{14}$C-3-[5-(2-fluoro-phenyl)-[1,2,4]oxadiazol-3-yl]benzoic acid (50 mg/kg) to Sprague Dawley rats (in µg/g dosed).

| Sex | Matrix | 1 hr | 2 hr | 3 hr | 4 hr |
| --- | --- | --- | --- | --- | --- |
| Male | Eye | 3.39 | 2.59 | NS | NS |
| | Exorbital lacrimal gland | 21.1 | 27.5 | NS | NS |
| | Harderian gland | 21.6 | 22.3 | NS | NS |

TABLE 20-continued

Concentrations of radioactivity in eyes and related tissues determined by whole body autoradiography at specified times following a single oral administration of $^{14}$C-3-[5-(2-fluoro-phenyl)-[1,2,4]oxadiazol-3-yl]benzoic acid (50 mg/kg) to Sprague Dawley rats (in μg/g dosed).

| Sex | Matrix | 1 hr | 2 hr | 3 hr | 4 hr |
|---|---|---|---|---|---|
| | Intra-orbital lacrimal gland | 21.8 | 26.0 | NS | NS |
| Female | | 1.41 | BLQ | NS | NS |
| | Exorbital lacrimal gland | 10.3 | 3.89 | NS | NS |
| | Harderian gland | 18.7 | 8.26 | NS | NS |
| | Intra-orbital lacrimal gland | 10.2 | 4.72 | NS | NS |

BLQ = below the limit of quantitation (<0.768 μg equivalents $^{14}$C-3-[5-(2-fluoro-phenyl)-[1,2,4]oxadiazol-3-yl]benzoic acid).
NS = not sampled (sample not discernible from background).

Long Evans rats: In a quantitative whole body autoradiography (QWBA) study, 8 male Long Evans rats (partially pigmented) obtained from Harlan were administered a single oral gavage dose of 50 mg/kg $^{14}$C-Compound 1.

Animals were individually housed and certified rodent diet and water were provided ad libitum. Animals were acclimated for 3 days prior to dose administration. Environmental controls for the animal room were set to maintain a temperature of 18 to 26° C., a relative humidity of 50±20%, and a 12-hour light/12-hour dark cycle. As necessary, the 12-hour dark cycle was interrupted to accommodate study procedures. Animals were fasted overnight through 4 hours postdose on the day of dosing. At dosing, the animals weighed 160 to 178 g and were approximately 7 weeks of age. One animal/time point was sacrificed via exsanguination (cardiac puncture) under isoflurane anesthesia at 0.5, 1, 2, 4, 8, 24, 72, and 168 hours postdose. The concentrations of $^{14}$C-Compound 1 in the eye and related tissues are shown in Table 21.

TABLE 21

Concentrations of radioactivity in eyes and related tissues determined by whole body autoradiography at specified times following a single oral administration of $^{14}$C-3-[5-(2-fluoro-phenyl)-[1,2,4]oxadiazol-3-yl]benzoic acid (50 mg/kg) to Long Evans rats (in μg/g dosed).

| Matrix | 0.5 hr | 1 hr | 2 hr | 4 hr | 8 hr | 24 hr | 72 hr | 168 hr |
|---|---|---|---|---|---|---|---|---|
| Eye | 4.59 | 1.78 | 3.62 | 2.69 | 2.08 | BLQ | ND | ND |
| Eye (lens) | BLQ | BLQ | BLQ | BLQ | BLQ | BLQ | ND | ND |
| Exorbital lacrimal gland | 28.0 | 7.59 | 22.4 | 10.2 | 8.09 | BLQ | BLQ | ND |
| Harderian gland | 46.8 | 16.0 | 38.2 | 18.1 | 13.0 | 1.59 | ND | ND |
| Intra-orbital lacrimal gland | 28.8 | 10.3 | 25.2 | 11.7 | 10.3 | BLQ | ND | ND |
| Uveal tract | 20.6 | 10.4 | 18.1 | 6.09 | 11.6 | BLQ | ND | ND |

BLQ = below the limit of quantitation (<0.457 μg equivalents $^{14}$C-3-[5-(2-fluoro-phenyl)-[1,2,4]oxadiazol-3-yl]benzoic acid).
ND = not detected (sample not discernible from background).

6.14. Nonsense Mutation Mouse Model of Aniridia

Compound 1 inhibited disease progression and reversed malformation in the cornea, lens and retina in a mouse model of aniridia (semi-dominant small eye model (PAX6$^{sey+/-}$)) developed by Gregory-Evans and associates which contains a naturally occurring nonsense mutation in the mouse PAX6 gene.

Compound 1 was administered subcutaneously to PAX6 mutant and wild-type mice for 10 days (Postnatal Day 4-14) or administered topically as an ophthalmic suspension formulation (0.9% sodium chloride, 1% Tween 80, 1% powdered Compound 1, 1% carboxymethylcellulose), twice per day for 46 days (Postnatal Day 14-60). Prior to treatment, the mutant eyes showed thickening of the cornea, the appearance of a lenticular stalk in which the underdeveloped lens was attached to the cornea, and thickening of the retina with abnormal in-folding at the ciliary margin (FIG. 36A). In the untreated mutant mouse group, progressive in-folding of the retina and abnormally small lenses was observed. Treatment with subcutaneous Compound 1 corrected the retinal in-folding and increased the size of the lens by 70% (FIG. 36A and FIGS. 37A and B).

Additional successful results were achieved after topical administration of Compound 1 directly into the eye as an ophthalmic suspension formulation (0.9% sodium chloride, 1% Tween 80, 1% powdered Compound 1, 1% carboxymethylcellulose). The lens and retinal defects, observed in the untreated eyes, reversed in the Compound 1-treated mutant mice and closely resembled wild-type mice (FIG. 36B). Histological examination of the cornea showed decreased corneal thickening. The retina showed increased response to light stimulation. Treatment with Compound 1 caused an increase in the PAX6 protein by 90% in the corneal and retinal epithelium protein lysates compared to wild-type mice (FIG. 36C) as measured by enzyme-linked immunosorbent assay (ELISA). A mouse model containing a splice-site mutation in PAX6 (PAX6$^{Sey-1Neu}$) did not show a response to Compound 1 therapy, demonstrating that Compound 1 is specific to the nonsense mutations.

As a test for effects on visual acuity in the mice, the optokinetic tracking response was measured, which is a behavioural response mediated through the retina-brain circuitry. The untreated mutant mice showed limited tracking responses. Mice treated with Compound 1 showed significant improvement in the spatial frequency threshold that was similar to the wild-type mice (FIG. 36D).

Compound 1 was shown to suppress the nonsense codon in PAX6, allowing for the full-length PAX6 protein to be synthesized and resulting in the reversal of the congenital ocular malformation associated with the disease. This indicates that Compound 1 has the potential to be a promising treatment for aniridia.

6.15. Diagnosis of Aniridia

Aniridia is diagnosed via a clinical examination entailing slit lamp examination, fundoscopy, iris fluorescein angiography, optical coherence tomography, and high frequency ultrasound biomicroscopy. An overview of the diagnostic techniques are provided in Table 22.

TABLE 22

Diagnostic Techniques Used to Identify the Ocular Abnormalities of Aniridia

| Diagnostic Technique | Ocular Abnormalities Identified |
|---|---|
| Slit lamp examination | Partial or complete absence of the iris<br>Iris translucency or abnormal architecture<br>Pupillary abnormalities<br>Corneal opacification and vascularization<br>Cataracts and glaucoma |

TABLE 22-continued

Diagnostic Techniques Used to Identify
the Ocular Abnormalities of Aniridia

| Diagnostic Technique | Ocular Abnormalities Identified |
| --- | --- |
| Fundoscopy (slit lamp or binocular indirect ophthalmoscopy) | Absence of or reduction in the normal foveal architecture (frequent)<br>Optic nerve abnormalities (less common)<br>Other retinal problems (rare) |
| Iris fluorescein angiography | Subtle iris hypoplasia |
| Optical coherence tomography (OCT) | Foveal hypoplasia (difficult to perform in presence of nystagmus) |
| Anterior segment OCT | Delinate the detailed anatomy of the anterior segment structures |
| High frequency ultrasound biomicroscopy | Corneal opacity or severe corneal oedema in infants |
| High frequency anterior segment ultrasound | Iris hypoplasia and/or absence |

Sequencing analysis is performed to identify the disease-causing mutation. The PAX6 coding region is analysed to determine the deletion/duplication and to detect the PAX6 exonic or whole gene deletions. The performed genetic tests are provided in Table 23.

TABLE 23

Genetic Tests For Aniridia by Phenotype and Family History

| Phenotype | Gene | Test | Mutations Detected | Mutation Detection Frequency by Phenotype and Test Method Family History | |
| --- | --- | --- | --- | --- | --- |
| | | | | Positive | Negative |
| Isolated Aniridia | PAX6 | Sequence analysis of coding region | Sequence alterations | 55% | 62.5% |
| | | Deletion testing | Exonic deletions and deletions of control regions | 22% | 17% |
| WAGR Syndrome | PAX6 and contiguous genes | High-resolution cytogenetic testing | Cytogenetic deletion 11p13 | 57% | NA |
| | PAX6 and WT1 | FISH | Submicroscopic deletion | 14% | NA |
| | | Deletion testing | Whole-gene deletions | Unknown | NA |

It will be appreciated that, although specific embodiments of the invention have been described herein for purposes of illustration, the invention described herein is not to be limited in scope by the specific embodiments herein disclosed. These embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description, which modification also intended to be within the scope of this invention.

What is claimed is:

1. A crystalline salt form comprising 3-[5-(2-fluoro-phenyl)-[1,2,4]oxadiazol-3-yl]benzoic acid and magnesium, wherein said crystalline salt form has an X-ray powder diffraction substantially shown in FIG. 2.

2. A method for treating, preventing or managing an ocular disease associated with a nonsense mutation or a premature stop codon in a patient having an ocular disease associated with a nonsense mutation or premature stop codon, comprising administering a pharmaceutical composition comprising an effective amount of the crystalline salt form of claim 1 to said patient.

3. The method of claim 2, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

4. A crystalline salt form comprising 3-[5-(2-fluoro-phenyl)-[1,2,4]oxadiazol-3-yl]benzoic acid and potassium, wherein said crystalline salt form has an X-ray powder diffraction pattern substantially as shown in FIG. 4.

5. A method for treating, preventing or managing an ocular disease associated with a nonsense mutation or a premature stop codon in a patient having an ocular disease associated with a nonsense mutation or a premature stop codon, comprising administering a pharmaceutical composition comprising an effective amount of the crystalline salt form of claim 4 to said patient.

6. The method of claim 5, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

7. A crystalline salt form comprising 3-[5-(2-fluoro-phenyl)-[1,2,4]oxadiazol-3-yl]benzoic acid and sodium, wherein said crystalline salt form has an X-ray powder diffraction pattern substantially as shown in FIG. 6.

8. A method for treating, preventing or managing an ocular disease associated with a nonsense mutation or a premature stop codon in a patient having an ocular disease associated with a nonsense mutation or a premature stop codon, comprising administering a pharmaceutical composition comprising an effective amount of the crystalline salt form of claim 7 to said patient.

9. The method of claim 8, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

10. A crystalline salt form comprising 3-[5-(2-fluoro-phenyl)-[1,2,4]oxadiazol-3-yl]benzoic acid and tromethamine, wherein said crystalline salt form has an X-ray powder diffraction pattern substantially as shown in FIG. 8.

11. A method for treating, preventing or managing an ocular disease associated with a nonsense mutation or a premature stop codon in a patient having an ocular disease associated with a nonsense mutation or a premature stop codon, comprising administering a pharmaceutical composition comprising an effective amount of the crystalline salt form of claim 10 to said patient.

12. The method of claim 11, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

13. A crystalline salt form comprising 3-[5-(2-fluorophenyl)-[1,2,4]oxadiazol-3-yl]benzoic acid and L-lysine, wherein said crystalline salt form has an X-ray powder diffraction pattern substantially as shown in FIG. 12.

14. A method for treating, preventing or managing an ocular disease associated with a nonsense mutation or a premature stop codon in a patient having an ocular disease associated with a nonsense mutation or a premature stop codon, comprising administering a pharmaceutical composition comprising an effective amount of the crystalline salt form of claim 13 to said patient.

15. The method of claim 14, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

16. A crystalline salt form comprising 3-[5-(2-fluorophenyl)-[1,2,4]oxadiazol-3-yl]benzoic acid and L-arginine, wherein said crystalline salt form has an X-ray powder diffraction pattern substantially as shown in FIG. 14.

17. A method for treating, preventing or managing an ocular disease associated with a nonsense mutation or a premature stop codon in a patient having an ocular disease associated with a nonsense mutation or a premature stop codon, comprising administering a pharmaceutical composition comprising an effective amount of the crystalline salt form of claim 16 to said patient.

18. The method of claim 17, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

19. A crystalline salt form comprising 3-[5-(2-fluorophenyl)-[1,2,4]oxadiazol-3-yl]benzoic acid and L-histidine, wherein said crystalline salt form has an X-ray powder diffraction pattern substantially as shown in FIG. 16.

20. A method for treating, preventing or managing an ocular disease associated with a nonsense mutation or a premature stop codon in a patient having an ocular disease associated with a nonsense mutation or a premature stop codon, comprising administering a pharmaceutical composition comprising an effective amount of the crystalline salt form of claim 19 to said patient.

21. The method of claim 20, wherein the ocular disease is selected from the group consisting of aniridia, choroideremia, renal-coloboma syndrome, Leber congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus and tunica vasculosa lentis.

* * * * *